United States Patent
Guerin et al.

(10) Patent No.: US 10,889,592 B2
(45) Date of Patent: Jan. 12, 2021

(54) THIENOPYRAZINE CARBOXAMIDES AS UBIQUITIN-SPECIFIC PROTEASE INHIBITORS

(71) Applicant: VALO EARLY DISCOVERY, INC., Boston, MA (US)

(72) Inventors: David Joseph Guerin, Natick, MA (US); Kenneth W. Bair, Wellesley, MA (US); Justin A. Caravella, Cambridge, MA (US); Stephanos Ioannidis, Jr., Natick, MA (US); David R. Lancia, Jr., Boston, MA (US); Hongbin Li, Madison, CT (US); Steven Mischke, Waltham, MA (US); Pui Yee Ng, Waltham, MA (US); David Richard, Littleton, MA (US); Shawn E. R. Schiller, Haverhill, MA (US); Tatiana Shelekhin, Ridgefield, CT (US); Zhongguo Wang, Lexington, MA (US)

(73) Assignee: VALO EARLY DISCOVERY, INC., Boston, MA (US)

( * ) Notice: Subject to any disclaimer, the term of this patent is extended or adjusted under 35 U.S.C. 154(b) by 0 days.

(21) Appl. No.: 16/077,406

(22) PCT Filed: Feb. 13, 2017

(86) PCT No.: PCT/US2017/017691
§ 371 (c)(1),
(2) Date: Aug. 10, 2018

(87) PCT Pub. No.: WO2017/139779
PCT Pub. Date: Aug. 17, 2017

(65) Prior Publication Data
US 2019/0359628 A1    Nov. 28, 2019

Related U.S. Application Data

(60) Provisional application No. 62/294,583, filed on Feb. 12, 2016.

(51) Int. Cl.
C07D 495/04    (2006.01)

(52) U.S. Cl.
CPC .................. *C07D 495/04* (2013.01)

(58) Field of Classification Search
CPC .................................................. C07D 495/04
See application file for complete search history.

(56) References Cited

FOREIGN PATENT DOCUMENTS

| WO | 2000078934 A2 | 12/2000 |
|---|---|---|
| WO | 2005037845 A1 | 4/2005 |
| WO | 2006068618 A1 | 6/2006 |
| WO | 2010092153 | 8/2010 |
| WO | 2010099166 A1 | 9/2010 |
| WO | 2012040527 A2 | 3/2012 |
| WO | 2014105952 A2 | 7/2014 |
| WO | 2014116859 A1 | 7/2014 |

OTHER PUBLICATIONS

Beroukhim et al., "The landscape of somatic copy-number alteration across human cancers," Nature vol. 463, doi.10.1038/nature08822, pp. 899-905, (2010).
Bradley et al., "Tumor necrosis factor receptor-associated factors (TRAFs)," Oncogene Nature 20, pp. 6482-6491,(2001).
Brockman et al., "Small Molecule Inhibitors of Aurora—A Induce Proteasomal Degradation of N-Myc in Childhood Neuroblastoma" Cancer Cell., 24(1), Doi:10.1016/.ccr.2013.05.005, pp. 75-89, (2013).
Colland et al., "Small-molecule inhibitor of USP7/HAUSP ubiquitin protease stabilizes and activates p53 in cells," Molecular Cancer Therapeutics, DOI: 10.1158-1535-7163.MCT-09-0097, pp. 2286-2295, (2009).
Colombo et al., "Synthesis and biological evaluation of 9-oxo-9H-indeno[1,2-b]pyrazine-2,3-dicarbonitrile Analogues as Potential Inhibitors of Deubiquitinating Enzymes," ChemMedChem DOI: 10.1002/cmdc.200900409, pp. 552-558, (2010).
Conacci-Sorrell et al., "An Overview of MYC and Its Interactome," Cold Spring Harb Perspect Med 2014;4: a014357, pp. 1-24 (2014).
Cui et al., "Mechanisms and pathways of innate immune activation and regulation in health and cancer," Human Vaccines & Immunotherapeutics 10:11, pp. 3270-3285, (2014).
D'Arcy et al., "Deubiquitinase inhibition as a cancer therapeutic strategy," Pharmacology & Therapeutics 147, http://dx.doi.org/10.1016/j.pharmthera.2014.11.002, pp. 32-54, (2015).
Diefenbacher et al., "The deubiquitinase USP28 controls intestinal homeostasis and promotes colorectal cancer," The Journal of Clinical Investigation, vol. 124, No. 8 doi:10.1172/JCI73733, pp. 3407-3418 (2014).
Flugel et al., "GSK-3B regulates cell growth, migration, and angiogenesis via Fbw7 and USP28-dependent degradation of HIF-1a," Vascular Biology, Blood, vol. 119, No. 5, pp. 1292-1301, (2012).
Gabay et al., "MYC Activation is a Hallmark of Cancer Initiation and Maintenance," Cold Spring Harb Perspect Med 2014;4:a014241, pp. 1-13 (2014).

(Continued)

*Primary Examiner* — Bruck Kifle
(74) *Attorney, Agent, or Firm* — Barnes & Thornburg, LLP

(57) ABSTRACT

The disclosure relates to inhibitors of USP28 and/or USP25 useful in the treatment of cancers, inflammation, autoimmune diseases, and infectious diseases, having the Formula: (I), where $R_1$, $R_2$, $R_3$, $R_4$, $R_{4'}$, $R_5$, $R_6$, X, and n are described herein.

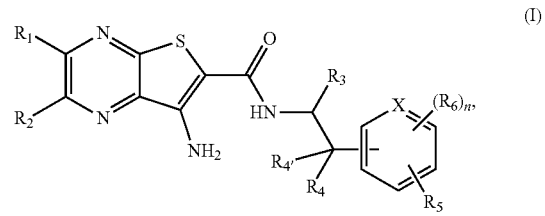

(I)

28 Claims, No Drawings

(56) References Cited

OTHER PUBLICATIONS

Guo et al., "USP28 is a potential prognostic marker for bladder cancer," Tumor Biology DOI 10.1007/ s13277-013-1525-1, pp. 4017-4022 (2013).
Huang et al., "Neuroblastoma and MYCN," Cold Spring Harb Perspect Med 2013;3:a014415; pp. 1-22, (2013).
International Search Report and Written Opinion for International Application No. PCT/US2017/017690, pp. 1-11, Apr. 19, 2017.
International Search Report and Written Opinion for International Application No. PCT/US2017/017691, pp. 1-6, Mar. 29, 2017.
Iwakura et al., "Functional Specialization of Interleukin-17 Family Members," Immunity 34, pp. 149-162 (2011).
Kapuria et al., "Deubiquitinase Inhibition by Small-Molecule WP1130 Triggers Aggresome Formation and Tumor Cell Apoptosis," Cancer Research Therapeutics, Targets, and Chemical Biology DOI: 10.1158/0008-5472.CAN-10-1530, pp. 9265-9276, (2010).
Knobel et al., "USP28 Is Recruited to Sites of DNA Damage by the Tandem BRCT Domains of 53BP1 but Plays a Minor Role in Double-Strand Break Metabolism," Molecular and Cellular Biology, vol. 34, No. 11, pp. 2062-2074 (2014).
Komander et al., "Breaking the chains: structure and function of the deubiquitinases," Nature, vol. 10, pp. 550-563 (2009).
Le et al., "Discovery of a selective M4 positive allosteric modulator based on the 3-amino-thieno[2,3-b]pyridine-2-carboxamide scaffold: development of ML253, a potent and brain penetrant compound that is active in a preclinical model of schizophrenia," Bioorg Med Chem Lett. doi:10.1016/j.bmcl.2012.10.073, pp. 346-350 (2013).
Lee et al., "Enhancement of proteasome activity by a small-molecule inhibitor of USP14," Nature 467 doi:10.1038/nature09299, pp. 179-184 (2010).
Li et al., "miRNA-200c inhibits invasion and metastasis of human non-small cell lung cancer by directly targeting ubiquitin specific peptidase 25," Molecular Cancer, vol. 13, pp. 1-14 (2014).
Liang et al., "A selective USP1-UAF1 inhibitor links deubiquitination to DNA damage responses," Nat. Chem. Biol. DOI: 10.1038/NCHEMBIO.1455, pp. 298-304 (2014).
Lorenzin et al., "Different promoter affinities account for specificity in MYC-dependent gene regulation," eLife 2016;5:e15161, pp. 1-35 (2016).
Meng et al., "γ-Secretase Inhibitors Abrogate Oxaliplatin-Induced Activation of the Notch-1 Signaling Pathway in Colon Cancer Cells Resulting in Enhanced Chemosensitivity," Cancer Research 69(2), pp. 573-582 (2009).
Metzger et al., "LSD1 demethylates repressive histone marks to promote androgen-receptor-dependent transcription," Nature doi:10.1038/nature04020, vol. 437, pp. 436-439 (2005).
Meyer et al. "Reflecting on 25 years with MYC," Nature Perspectives, vol. 8, pp. 976-990 (2008).
Nijman et al., "A Genomic and Functional Inventory of Deubiquitinating Enzymes," Cell 123, pp. 773-786 (2005).
Periz et al., "Regulation of Protein Quality Control by UBE4B and LSD1 through p53-Mediated Transcription," PLOS Biology DOI:10.1371/journal.pbio.1002114, pp. 1-29 (2015).
Popov et al., "The ubiquitin-specific protease USP28 is required for MYC stability," Nature Cell Biology, vol. 9, No. 7, pp. 765-774 (2007).
Reverdy et al., "Discovery of Specific Inhibitors of Human USP7/HAUSP Deubiquitinating Enzyme," Chemistry & Biology 19, pp. 467-477 + Supplemental Information, (2012).
Roussel et al., "Role of MYC in Medulloblastoma," Cold Spring Harb Perspect Med 2013;3:a014308; pp. 1-15, (2013).
Sankar et al., "Reversible LSD1 Inhibition Interferes with Global EWS/ETS Transcriptional Activity and Impedes Ewing Sarcoma Tumor Growth," Clinical Cancer Research, DOI: 10.1158/1078-0432.CCR-14/0072, pp. 4584-4597 (2014).
Schenk et al., "Inhibition of the LSD1 (KDM1A) demethylase reactivates the all-trans-retinoic acid differentiation pathway in acute myeloid leukemia," Nature Medicine, vol. 18, No. 4, pp. 605-611 (2012).
Schmitz et al., "Oncogenic Mechanisms in Burkitt Lymphoma," Cold Spring Harb Perspect Med 2014;4:a014282, pp. 1-13 (2014).
Sheridan, C., "Drug makers target ubiquitin proteasome pathway anew," Nature Biotechnology, vol. 33, No. 11, pp. 1115-1117 (2015); corrected version (2016).
Stoeck et al., "Discovery of Biomarkers Predictive of GSI Response in Triple-Negative Breast Cancer and Adenoid mystic Carcinoma," American Association for Cancer Research, Cancer Discovery DOI: 10.1158/2159-8290. CD-13-0830, pp. 1155-1167 (2014).
Toffolo et al,, "Phosphorylation of neuronal Lysine-Specific Demethylase 1LSD1/KDM1A impairs transcriptional repression by regulating interaction with CoREST and histone deacetylases HDAC1/2," Journal of Neurochemistry, vol. 128, doi: 10.1111/jnc.12457, pp. 603-616 (2014).
Walsh et al., "Tumor necrosis factor receptor-associated factor 6 (TRAF6) regulation of development, function, and homeostasis of the immune system," John Wiley & Sons Ltd, Immunological Reviews 0105-2896, vol. 266, pp. 72-92 (2015).
Walz et al., "Activation and repression by oncogenic MYC shape tumour-specific gene expression profiles," Nature, doi:10.1038/nature13473, pp. 1-17 (2014).
Wang et al., "Ubiquitin-specific protease 28 is overexpressed in human glioblastomas and contributes to glioma tumorigenicity by regulating MYC expression," Experimental Biology and Medicine, DOI: 10.1177/1535370215595468, pp. 255-264 (2015).
Weng et al., "Activating Mutations of NOTCH1 in Human T Cell Acute Lymphoblastic Leukemia," Science, vol. 306, pp. 269-271 (2004).
Wrigley et al., "Enzymatic characterisation of USP7 deubiquitinating activity and inhibition," Cell Biochem. Biophys., vol. 60, DOI 10.1007/s12013-011-9186-4, pp. 99-111 (2011).
Wrigley et al., "Identification and Characterization of Dual Inhibitors of the USP25/28 Deubiquitinating Enzyme Subfamily" ACS Chem. Biol. 12, pp. 3113-3125 (2017).
Wu et al., "The Deubiquitinase USP28 Stabilizes LSD1 and Confers Stem-Cell-like Traits to Breast Cancer Cells," Cell Press Reports, vol. 5, pp. 224-236 (2013).
Zhang et al., "A Role for the Deubiquitinating EnzymeUSP28 in Control of the DNA-Damage Response," Cell 126, pp. 529-542 (2006).
Zhang et al., "Overexpression of deubiquitinating enzyme USP28 promoted non-small cell lung cancer growth," J. Cell Mol. Med., pp. 1-7 , dol: 10.1111/jcmm.12426 (2015).
Zhong et al., "Negative regulation of IL-17-mediated signaling and inflammation by the ubiquitin-specific protease USP25," Nature Immunology, vol. 13, No. 11, pp. 1110-1117 (2012).
Zhong et al., "Ubiquitin-Specific Protease 25 Regulates TLR4-Dependent Innate Immune Responses Through Deubiquitination of the Adaptor Protein TRAF3," Science Signaling, vol. 6, Issue 275 ra35, pp. 1-10 (2013).
Zhong et al., "Ubiquitin-Specific Proteases 25 Negatively Regulates Virus-Induced Type I Interferon Signaling," PLOS One, vol. 8, Issue 11, pp. 1-14 (2013).
International Search Report issued in Application No. PCT/US2018/046061, dated Oct. 25, 2018.
International Search Report issued in Application No. PCT/US2019/045732, dated Oct. 23, 2019.
Examination Report issued in European Patent Application No. 17708031.4, dated Jun. 13, 2019.
Cremona et al., "Fbw7 and Its Counteracting Forces in Stem Cells and Cancer: Oncoproteins in the Balance," Semin Cancer Biol., 36:52-61, Feb. 2016.
Diefenbacher et al., "Usp28 Counteracts Fbw7 in Intestinal Homeostasis and Cancer," Cancer Res., 75(7):1181-6, Apr. 1, 2015. (Epub Feb. 25, 2015).
Farshi et al., "Deubiquitinases (DUBs) and DUB inhibitors: a patent review," Expert Opin Ther Pat., 25 (10):1191-1208, 2015.
Gersch et al., "Distinct USP25 and USP28 Oligomerization States Regulate Deubiquitinating Activity," Mol. Cell 74:436-451, May 2, 2019.
Popov et al., "Fbw7 and Usp28 Regulate Myc Protein Stability in Response to DNA Damage," Cell Cycle, 6:19, 2327-2331, Oct. 2, 2007.

(56) References Cited

OTHER PUBLICATIONS

Prieto-Garcia et al., "The USP28-ΔNp63 axis is a vulnerability of squamous tumours," bioRxiv preprint, Jun. 27, 2019.
Sacco et al., "Emerging Roles of Deubiquitinases in Cancer-Associated Pathways," Life 62(2):140-157, Feb. 2010.
Sauer et al., "Differential Oligomerization of the Deubiquitinases USP25 and USP28 Regulates Their Activities," Mol. Cell 74(3):421-435, May 2, 2019.
Schulein-Volk et al., "Dual Regulation of Fbw7 Function and Oncogenic Transformation b Usp28," Cell Reports 9, 1099-1109, Nov. 6, 2014.
Wrigley et al., "Identification and Characterization of Dual Inhibitors of the USP25/28 Deubiquitinating Enzyme Subfamily," Peer-reviewed (pre-print) version, published Nov. 13, 2017.

US 10,889,592 B2

THIENOPYRAZINE CARBOXAMIDES AS UBIQUITIN-SPECIFIC PROTEASE INHIBITORS

RELATED APPLICATIONS

This application is a national phase entry pursuant to 35 U.S.C. § 371 of International Application No. PCT/US2017/017691, filed Feb. 13, 2017, which claims the benefit of and priority to U.S. provisional application No. 62/294,583, filed Feb. 12, 2016, the entire contents of which are incorporated herein by reference in its entirety.

FIELD OF INVENTION

The present disclosure is directed to modulators of ubiquitin-specific protease 28 (USP28) and/or ubiquitin-specific protease 25 (USP25) useful in the treatment of diseases or disorders associated with USP28 and/or USP25 enzymes. Specifically, the disclosure is concerned with compounds and compositions inhibiting USP28 and/or USP25, methods of treating diseases or disorders associated with USP28 and/or USP25, and methods of synthesis of these compounds.

BACKGROUND OF THE INVENTION

USP28 and USP25 are cysteine isopeptidases of the USP sub-family of DUBs containing three distinct domains: an N-terminal UBA-like domain; a pair of ubiquitin-interacting motifs (UIM) and a USP domain that is predicted to have the conserved fold of the USP sub-family (Nijman et al., *Cell* 2005, 123, 773-786; Komander et al., *Mol. Cell Bio.* 2009, 10, 550-563). USP28 and USP25 exert their function through regulating the stability of a plethora of cellular proteins. USP28 has been characterized as a tumor-promoting factor and has been found to stabilize many oncoproteins. USP25 has been characterized as a tumor-promoting factor and as a regulator of cellular responses related to autoimmune disease, inflammation, and infectious diseases (such as viruses and bacteria).

Amplification, deletions and mutations of USP28 have been identified in multiple cancer types, including breast cancer, AML, ovarian cancer, and colorectal cancer. (cbioportal; http://www.cbioportal.org; Diefenbacher et al., *J. of Clin. Investi.* 2014, 124, 3407-3418; Popov et al., *Nat. Cell. Biol.* 2007, 9, 729-731). Furthermore, USP28 overexpression has been correlated with poor prognosis in patients with glioblastoma, non-small cell lung carcinoma and bladder cancers suggesting that USP28 plays an important role in tumorigenesis of these tumor types. (Wang et al. *Exp. Biol. Med.* 2016, 255-264; Zhang et al. *J. Cell. Mol. Med.* 2015, 19, 799-805; Guo et al., *Tumor Bio.* 2014, 35, 4017-4022).

A large-scale shRNA screen has also identified a role of USP28 in the control of the stability of MYC protein. (Popov, *Nat. Cell. Biol.*, 765-774). MYC is a master regulator of the transcription of genes involved in cell growth, proliferation and apoptosis and is essential for tumor initiation and maintenance in many tumor types. (Meyer et al., *Nat. Rev. Cancer* 2008, 8, 976-990; Conacci-Sorrell et al., *Cold Spring Harb. Perspect. Med.* 2014, 4, 1-24; Huang et al., *Cold Spring Harb. Perspect. Med.* 2013; Roussel et al., *Cold Spring Harb. Perspect. Med.* 2013; Gabay et al., *Cold Spring Harb. Perspect. Med.* 2014; Schmitz et al., *Cold Spring Harb. Perspect. Med.* 2014). In addition, MYC is the most frequently amplified oncogene in human cancer, with alterations in many tumor types including breast, lung and prostate. (Beroukhim et al., *Nature* 2010, 463, 899-905). Knockdown of the USP28 gene has been shown to lead to a decrease of MYC protein and an associated inhibition of growth in a panel of human cancer cell lines in vitro. (Popov, *Nat. Cell Biol.*, 765-774).

USP28 has also been reported to be required to impart stability on the LSD1 (lysine-specific demethylase 1) protein. (Wu et al., *Cell Rep.* 2013, 5, 224-236). LSD1 is a histone demethylase that complexes with many partner proteins to control cellular pluripotency and differentiation. (Metzger et al. *Nature* 2005, 437, 436-439; Toffolo et al, *J. Neurochem.* 2014 128, 603-616, 2014; Periz et al., *PloS Biology* 2015). Knockdown of USP28 in tumor cells has been shown to lead to the destabilization of LSD1 protein, the suppression of cancer stem cell (CSC)-like characteristics in vitro, and the inhibition of tumor growth in vivo. (Wu, *Cell Rep.*, 224-236). Small molecule inhibitors of LSD1 have shown antitumor activity in models of AML and Ewing sarcoma. (Sankar et al., "Reversible LSD1 inhibition interferes with global EWS/ETS transcriptional activity and impedes Ewing sarcoma tumor growth" *Clin Cancer Res.* 2014 4584-4597; Schenk et al., *Nat. Med.* 2012, 18, 605-611). Thus, USP28 inhibition represents an alternate approach to targeting LSD1 in these tumor types.

USP28 inhibition has also been shown to reduce NICD1-Levels and to lead to inhibition of the NOTCH pathway activity. (Diefenbacher et al). NOTCH signaling controls diverse cellular differentiation decisions and drives tumorigenesis in certain tumor types. NOTCH1 is a potent T-cell oncogene, with >50% of T-cell acute lymphoblastic leukemia (T-ALL) cases carrying activating mutations in NOTCH1. (Weng et al. *Science* 2004, 306, 269-271). Increased NOTCH1 protein levels have also been associated with disease progression in colon cancer. (Meng et al., *Cancer Res.* 2009, 69, 573-582). NOTCH1 rearrangements lead to constitutive pathway activation and drive tumorigenesis in many cancer types, including triple-negative breast cancer. (Stoeck et al., *Cancer Discov.* 2014, 4, 1154-1167).

Other reported substrates of USP28 include c-Jun, Cyclin E, HIF-1α, Claspin, 53BP1, and Mdc1, many of which play important roles in tumorigenesis in humans. (Diefenbacher et al.; Flugel et al. *Blood* 2012, 119, 1292-1301; Zhang et al., "A role for the deubiquitinating enzyme USP28 in control of the DNA-damage response" *Cell* 2006, 126, 529-542). Interestingly, many USP28 substrates are recognized by FBW7, the substrate recognition subunit of SCF (FBW7) E3 ubiquitin ligase. (Diefenbacher et al). FBW7 recognizes USP28 substrates in a phosphorylation-dependent manner and targets them for ubiquitination ultimately leading to their proteasomal degradation. The antagonizing roles of USP28 and FBW7 on their shared oncoprotein substrates indicate the intricate nature of protein stability control and may provide additional therapeutic opportunities for cancer treatment.

Mice with a germline knockout of USP28 have been shown to be viable and fertile, confirming that USP28 activity is not required for normal development and reproductive function. (Knobel et al., *Molecular and Cellular Biology* 2014, 34, 2062-2074). Conditional knockout of USP28 in mouse intestine led to the reduction of oncoproteins including c-Myc, active NOTCH (NICD1) and c-JUN which was associated with decreased intestinal cell proliferation and enhanced differentiation. More importantly, intestinal tumorigenesis induced by APC mutation was effectively blocked with acute USP28 depletion suggesting that USP28 could be an appealing target to reduce tumor burden and improve survival for intestinal cancers. (Diefenbacher et al).

In summary, USP28 and USP25 play important roles in promoting tumorigenesis in cells and modulating immune responses. Its major role being in the deubiquitination and stabilization of diverse oncoproteins and epigenetic drivers and immunomodulatory proteins among other cellular factors, which are necessary for immune responses and tumor initiation and growth in humans. Inhibition of USP28 with small molecule inhibitors therefore has the potential to be a treatment for cancers, autoimmune diseases, inflammatory diseases, infectious diseases, and other disorders. For this reason, there remains a considerable need for novel and potent small molecule inhibitors of USP28 and/or USP25.

SUMMARY OF THE DISCLOSURE

A first aspect of the disclosure relates to compounds of Formula (I):

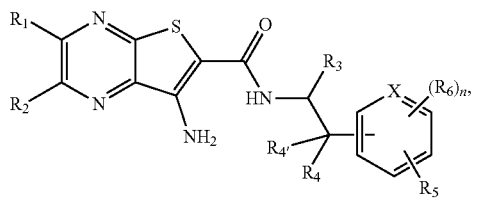

and pharmaceutically acceptable salts, hydrates, solvates, prodrugs, stereoisomers, and tautomers thereof,
wherein:

X is N or $CR_6$;

$R_1$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, —CN, or —$NR_8R_9$;

$R_2$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, or —$NR_{10}R_{11}$;

or $R_1$ and $R_2$ together form a $(C_4-C_8)$ cycloalkyl optionally substituted with one or more $R_{12}$;

$R_3$ is H, $(C_1-C_6)$ alkyl, or $(C_1-C_6)$ haloalkyl;

$R_4$ is H, $(C_1-C_6)$ alkyl, halogen, or $(C_1-C_6)$ haloalkyl;

$R_{4'}$ is H, $(C_1-C_6)$ alkyl, halogen, or $(C_1-C_6)$ haloalkyl;

$R_5$ is —$(C_0-C_3)$ alkylene-C(O)OH, —$(C_0-C_3)$ alkylene-heterocycloalkyl, —O-heterocycloalkyl, —$(C_0-C_3)$ alkylene-aryl, —$(C_0-C_3)$ alkylene-heteroaryl or —N($R_7$)—$(C_0-C_3)$ alkylene-heterocycloalkyl, wherein the heterocycloalkyl, aryl and heteroaryl are optionally substituted with one or more $R_{13}$;

each $R_6$ is independently at each occurrence H, $(C_1-C_6)$ alkyl, $(C_1-C_6)$ alkoxy, $(C_1-C_6)$ haloalkyl, $(C_1-C_6)$ haloalkoxy, halogen, —OH, —CN, $(C_3-C_8)$ cycloalkyl, heterocycloalkyl, aryl, or heteroaryl, wherein the alkyl is optionally substituted with one or more $(C_1-C_6)$ alkoxy or —OH, and wherein the cycloalkyl, heterocycloalkyl, aryl, and heteroaryl are optionally substituted with one or more $R_{14}$; or $R_5$ and $R_6$ together when on adjacent atoms form a $(C_4-C_8)$ cycloalkyl ring optionally substituted with one or more $R_{15}$; or $R_5$ and $R_6$ together when on adjacent atoms form a heterocycloalkyl ring optionally substituted with one or more $R_{15}$; $R_5$ and $R_6$ together when on adjacent atoms form an aryl ring optionally substituted with one or more $R_{15}$; or $R_5$ and $R_6$ together when on adjacent atoms form a heteroaryl ring optionally substituted with one or more $R_{15}$; or two $R_6$ together when on adjacent atoms form a $(C_4-C_8)$ cycloalkyl ring; or two $R_6$ together when on adjacent atoms form a heterocycloalkyl ring; two $R_6$ together when on adjacent atoms form an aryl ring; or two R together when on adjacent atoms form a heteroaryl ring;

$R_7$ is H or $(C_1-C_6)$ alkyl;

each $R_8$, $R_9$, $R_{10}$, and $R_1$ is independently H, $(C_1-C_6)$ alkyl, or —$C(O)(C_1-C_6)$ alkyl;

each $R_{12}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, or —OH;

each $R_{13}$ is independently at each occurrence $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, —$C(O)NR_{18}R_{19}$, —$S(O)_2(C_1-C_6)$ alkyl, —OH, or —$NR_{16}R_{17}$, wherein the alkyl is optionally substituted with one or more substituents independently selected from $(C_1-C_6)$ alkoxy, OH, and heterocycloalkyl; or two $R_{13}$ together when attached to the same carbon can form —C=(O) when $R_5$ is —$(C_0-C_3)$ alkylene-heterocycloalkyl, —O-heterocycloalkyl, or —N($R_7$)—$(C_0-C_3)$ alkylene-heterocycloalkyl; or two $R_{13}$ together when attached to the same atom form a $(C_3-C_8)$ spirocycloalkyl optionally substituted with one or more $R_{20}$ when $R_5$ is —$(C_0-C_3)$ alkylene-heterocycloalkyl, —O-heterocycloalkyl, or —N($R_7$)—$(C_0-C_3)$ alkylene-heterocycloalkyl; or two $R_{13}$ together when attached to the same atom form a $(C_3-C_8)$ spiroheterocycloalkyl optionally substituted with one or more $R_2$ when $R_5$ is —$(C_0-C_3)$ alkylene-heterocycloalkyl, —O-heterocycloalkyl, or —N($R_7$)—$(C_0-C_3)$ alkylene-heterocycloalkyl; or two $R_{13}$ together when on adjacent atoms form a heterocycloalkyl ring optionally substituted with one or more $R_{20}$; or two $R_{13}$ together when on adjacent atoms form a heteroaryl ring optionally substituted with one or more $R_{20}$; or two $R_{13}$ together with the atoms to which they are attached can form a bridged heterocycloalkyl ring optionally substituted with one or more $R_{20}$ when $R_5$ is —$(C_0-C_3)$ alkylene-heterocycloalkyl, —O-heterocycloalkyl, or —N($R_7$)—$(C_0-C_3)$ alkylene-heterocycloalkyl;

each $R_{14}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, cycloalkyl, heterocycloalkyl, or —C(O)-heterocycloalkyl, wherein the alkyl is optionally substituted with one or more substituents independently selected from $(C_1-C_6)$ alkoxy and —OH;

each $R_{15}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —OH, —CN, —C(O)OH, or —C(O)O$(C_1-C_6)$ alkyl;

each $R_{16}$ and $R_{17}$ is independently H, $(C_1-C_6)$ alkyl, $(C_3-C_8)$ cycloalkyl, —$CH_2C(O)NH_2$, —$S(O)_2(C_1-C_6)$ alkyl, —$S(O)_2(C_6-C_{10})$ aryl or —$C(O)(C_1-C_6)$ alkyl;

each $R_{15}$ and Rig is independently H or $(C_1-C_6)$ alkyl;

each $R_{20}$ is independently at each occurrence $(C_1-C_6)$ alkyl, $(C_1-C_6)$ alkoxy, $(C_1-C_6)$ haloalkyl, $(C_1-C_6)$ haloalkoxy, or halogen; or two $R_{20}$ together when attached to the same carbon form —C=(O); and n is 0, 1, 2, or 3.

Another aspect of the disclosure relates to a method of treating a disease or disorder associated with inhibition of USP28. The method comprises administering to a patient in need of a treatment for diseases or disorders associated with inhibition of USP28 an effective amount of a compound of Formula (I), or a pharmaceutically acceptable salt, hydrate, solvate, prodrug, stereoisomer, or tautomer thereof.

Another aspect of the disclosure relates to a method of treating a disease or disorder associated with inhibition of USP25. The method comprises administering to a patient in need of a treatment for diseases or disorders associated with inhibition of USP28 an effective amount of a compound of Formula (I), or a pharmaceutically acceptable salt, hydrate, solvate, prodrug, stereoisomer, or tautomer thereof.

Another aspect of the disclosure relates to a method of treating a disease or disorder associated with inhibition of USP28 and USP25. The method comprises administering to a patient in need of a treatment for diseases or disorders associated with inhibition of USP28 an effective amount of a compound of Formula (I), or a pharmaceutically acceptable salt, hydrate, solvate, prodrug, stereoisomer, or tautomer thereof.

Another aspect of the disclosure is directed to a method of inhibiting USP28. The method involves administering to a patient in need thereof an effective amount of a compound of Formula (I), or a pharmaceutically acceptable salt, hydrate, solvate, prodrug, stereoisomer, or tautomer thereof.

Another aspect of the disclosure is directed to a method of inhibiting USP25. The method involves administering to a patient in need thereof an effective amount of a compound of Formula (I), or a pharmaceutically acceptable salt, hydrate, solvate, prodrug, stereoisomer, or tautomer thereof.

Another aspect of the disclosure is directed to a method of inhibiting USP28 and USP25. The method involves administering to a patient in need thereof an effective amount of a compound of Formula (I), or a pharmaceutically acceptable salt, hydrate, solvate, prodrug, stereoisomer, or tautomer thereof.

Another aspect of the disclosure relates to a method of treating cancer. The method comprises administering to a patient in need thereof an effective amount of a compound of Formula (I), or a pharmaceutically acceptable salt, hydrate, solvate, prodrug, stereoisomer, or tautomer thereof.

Another aspect of the disclosure relates to a method of treating inflammation. The method comprises administering to a patient in need thereof an effective amount of a compound of Formula (I), or a pharmaceutically acceptable salt, hydrate, solvate, prodrug, stereoisomer, or tautomer thereof.

Another aspect of the disclosure relates to a method of treating an autoimmune disease. The method comprises administering to a patient in need thereof an effective amount of a compound of Formula (I), or a pharmaceutically acceptable salt, hydrate, solvate, prodrug, stereoisomer, or tautomer thereof.

Another aspect of the disclosure relates to a method of treating an infectious disease. The method comprises administering to a patient in need thereof an effective amount of a compound of Formula (I), or a pharmaceutically acceptable salt, hydrate, solvate, prodrug, stereoisomer, or tautomer thereof.

Another aspect of the disclosure relates to a method of treating a viral infection. The method comprises administering to a patient in need thereof an effective amount of a compound of Formula (I), or a pharmaceutically acceptable salt, hydrate, solvate, prodrug, stereoisomer, or tautomer thereof.

Another aspect of the disclosure relates to a method of treating a bacterial infection. The method comprises administering to a patient in need thereof an effective amount of a compound of Formula (I), or a pharmaceutically acceptable salt, hydrate, solvate, prodrug, stereoisomer, or tautomer thereof.

Another aspect of the disclosure is directed to pharmaceutical compositions comprising a compound of Formula (I), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the present disclosure relates to a compound of Formula (I), or a pharmaceutically acceptable salt, hydrate, solvate, prodrug, stereoisomer, or tautomer thereof, for use in the manufacture of a medicament for treating a disease associated with inhibiting USP28.

Another aspect of the present disclosure relates to the use of a compound of Formula (I), or a pharmaceutically acceptable salt, hydrate, solvate, prodrug, stereoisomer, or tautomer thereof, in the treatment of a disease associated with inhibiting USP28.

Another aspect of the present disclosure relates to the use of a compound of Formula (I), or a pharmaceutically acceptable salt, hydrate, solvate, prodrug, stereoisomer, or tautomer thereof, in the treatment of a disease associated with inhibiting USP25.

Another aspect of the present disclosure relates to the use of a compound of Formula (I), or a pharmaceutically acceptable salt, hydrate, solvate, prodrug, stereoisomer, or tautomer thereof, in the treatment of a disease associated with inhibiting USP28 and USP25.

The present disclosure further provides methods of treating a disease or disorder associated with modulation of USP28 and/or USP25 including, cancer, inflammation, an autoimmune disease, a viral infection, and a bacterial infection, comprising administering to a patient suffering from at least one of said diseases or disorder a compound of Formula (I), or a pharmaceutically acceptable salt, hydrate, solvate, prodrug, stereoisomer, or tautomer thereof.

The present disclosure provides inhibitors of USP28 and/or USP25 that are therapeutic agents in the treatment of diseases such as cancer, inflammation, autoimmune diseases, viral infections, and bacterial infections. Ultimately, the present disclosure provides the medical community with a novel pharmacological strategy for the treatment of diseases and disorders associated with USP28 and/or USP25 enzymes.

DETAILED DESCRIPTION OF THE DISCLOSURE

The present disclosure relates to compounds and compositions that are capable of inhibiting the activity USP28 and/or USP25. The disclosure features methods of treating, preventing or ameliorating a disease or disorder in which USP28 and/or USP25 plays a role by administering to a patient in need thereof a therapeutically effective amount of a compound of Formula (I), or a pharmaceutically acceptable salt, hydrate, solvate, prodrug, stereoisomer, or tautomer thereof. The methods of the present disclosure can be used in the treatment of a variety of USP28 and/or USP25 dependent diseases and disorders by inhibiting the activity of USP28 and/or USP25 enzymes. Inhibition of USP28 and/or USP25 provides a novel approach to the treatment, prevention, or amelioration of diseases including, but not limited to, cancer.

In a first aspect of the disclosure, the compounds of Formula (I) are described:

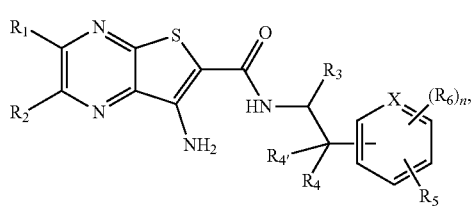

(I)

and pharmaceutically acceptable salts, hydrates, solvates, prodrugs, stereoisomers, and tautomers thereof, wherein $R_1$, $R_2$, $R_3$, $R_4$, $R_{4'}$, $R_5$, $R_6$, X, and n are as described herein above.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

DEFINITIONS

The articles "a" and "an" are used in this disclosure to refer to one or more than one (e.g., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, —NH(($C_1$-$C_6$) alkyl), —N(($C_1$-$C_6$) alkyl)$_2$, —NHC(O)($C_1$-$C_6$) alkyl, —C(O)NH($C_1$-$C_6$) alkyl, —S(O)$_2$($C_1$-$C_6$) alkyl, —S(O)NH($C_1$-$C_6$) alkyl, and S(O)N(($C_1$-$C_6$) alkyl)$_2$. The substituents can themselves be optionally substituted.

"Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, NH(($C_1$-$C_6$) alkyl), N(($C_1$-$C_6$) alkyl)$_2$, —S(O)$_2$—($C_1$-$C_6$) alkyl, —S(O)NH($C_1$-$C_6$) alkyl, and —S(O)N(($C_1$-$C_6$) alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, and S, the remaining ring atoms being C. Heteroaryl as herein defined also means a bicyclic heteroaromatic group wherein the heteroatom is selected from N, O, and S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1λ$^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d] imidazol-2-one, 3,4-dihydro-2H-pyrazolo[1,5-b][1,2] oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" refers to fluorine, chlorine, bromine, or iodine.

Alkyl refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, e.g., —O(alkyl). Examples of alkoxy groups include without limitation, methoxy, ethoxy, propoxy, butoxy, t-butoxy, or pentoxy groups.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a $C_0$-$C_6$ alkylene. An alkylene may further be a $C_0$-$C_4$ alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

"Cycloalkyl" or "carbocyclyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl and derivatives thereof. A $C_3$-$C_8$ cycloalkyl is a cycloalkyl group containing between 3 and 8 carbon atoms. A cycloalkyl group can be fused (e.g., decalin) or bridged (e.g., norbornane).

"Heterocyclyl" or "heterocycloalkyl" monocyclic or polycyclic rings containing carbon and heteroatoms taken from oxygen, nitrogen, or sulfur and wherein there is not delocalized π electrons (aromaticity) shared among the ring carbon or heteroatoms. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl.

The term "hydroxyalkyl" means an alkyl group as defined above, where the alkyl group is substituted with one or more OH groups. Examples of hydroxyalkyl groups include HO—CH$_2$—, HO—CH$_2$—CH$_2$— and CH$_3$—CH(OH)—.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, e.g., C≡N.

"Spirocycloalkyl" or "spirocyclyl" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A ($C_3$-$C_{12}$) spirocycloalkyl is a spirocycle containing between 3 and 12 carbon atoms. One or more of the carbon atoms can be substituted with a heteroatom.

The term "spiroheterocycloalkyl" or "spiroheterocyclyl" is understood to mean a spirocycle wherein at least one of the rings is a heterocycle (e.g., at least one of the rings is furanyl, morpholinyl, or piperadinyl).

The term "solvate" refers to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The term "cancer" includes, but is not limited to, the following cancers: bladder cancer, breast cancer (e.g., ductal carcinoma), cervical cancer (e.g.: squamous cell carcinoma), colorectal cancer (e.g., adenocarcinoma), esophageal cancer (e.g., squamous cell carcinoma), gastric cancer (e.g.: adenocarcinoma, medulloblastoma, colon cancer, choriocarcinoma, squamous cell carcinoma), head and neck cancer, hematologic cancer (e.g., acute lymphocytic anemia, acute myeloid leukemia, acute lymphoblastic B cell leukemia, anaplastic large cell lymphoma, B-cell lymphoma, Burkitt's lymphoma, chronic lymphocytic leukemia, chronic eosinophillic leukemia/hypereosinophillic syndrome, chronic myeloid leukemia, Hodgkin's lymphoma, mantle cell lymphoma, multiple myeloma, T-cell acute lymphoblastic leukemia), lung cancer (e.g., bronchioloalveolar adenocarcinoma, mesothelioma, mucoepidermoid carcinoma, small-cell lung cancer, non-small cell lung cancer, adenocarcinoma, squamous cell carcinoma), liver cancer (e.g., hepatocellular carcinoma), lymphoma, neurological cancer (e.g., glioblastoma, neuroblastoma, neuroglioma), ovarian (e.g., adenocarcinoma), pancreatic cancer (e.g., ductal carcinoma), prostate cancer (e.g., adenocarcinoma), renal cancer (e.g., renal cell carcinoma, clear cell renal carcinoma), sarcoma (e.g., chondrosarcoma, Ewings sarcoma, fibrosarcoma, multipotential sarcoma, osteosarcoma, rhabdomyosarcoma, synovial sarcoma), skin cancer (e.g., melanoma, epidermoid carcinoma, squamous cell carcinoma), thyroid cancer (e.g., medullary carcinoma), and uterine cancer.

As used herein, the terms "autoimmune disease" or "autoimmune disorder" refer to a condition that is immune-mediated due to an attack on self-tissues, such as when a subject's own antibodies react with host tissue, but can also involve an immune response to a microorganism. Examples of autoimmune diseases include, but are not limited to, multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, cutaneous lupus erythematosus including chilblain lupus erythematosus, lupus nephritis, discoid lupus, subacute cutaneous lupus erythematosus, dermatomyositis, polymyositis, idiopathic myxedema, Hashimoto's disease, Guillain-Barre' syndrome, Grave's disease, myasthenia gravis, Sjogren's syndrome, nodular panarteritis, autoimmune enteropathy, uveitis, autoimmune oophoritis, chronic immune thrombocytopenic purpura, colitis, diabetes, psoriasis, pemphigus vulgaris, proliferative glomerulonephritis, Wiskott-Aldrich syndrome, autoimmune lymphoproliferative syndrome, chronic arthritis, inflammatory chronic rhinosinusitis, colitis, celiac disease, inflammatory bowel disease, Barrett's esophagus, inflammatory gastritis, autoimmune nephritis, autoimmune vasculitis, autoimmune hepatitis, autoimmune carditis, autoimmune encephalitis, and autoimmune mediated hematological disease.

The present disclosure relates to compounds or pharmaceutically acceptable salts, hydrates, solvates, prodrugs, stereoisomers, or tautomers thereof, capable of inhibiting USP28 and/or USP25, which are useful for the treatment of diseases and disorders associated with modulation of a USP28 and/or USP25 enzyme. The disclosure further relates to compounds, or pharmaceutically acceptable salts, hydrates, solvates, prodrugs, stereoisomers, or tautomers thereof, which are useful for inhibiting USP28 and/or USP25.

In any of the embodiments of the invention, the cancer can be any cancer in any organ, for example, a cancer is selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof.

The present invention relates to compounds or pharmaceutically acceptable salts, hydrates, solvates, prodrugs, stereoisomers, or tautomers thereof, capable of inhibiting USP28 and/or USP25, which are useful for the treatment of diseases and disorders associated with modulation of a USP28 and/or USP25 enzyme. The invention further relates to compounds, or pharmaceutically acceptable salts, hydrates, solvates, prodrugs, stereoisomers, or tautomers thereof, which are useful for inhibiting USP28 and/or USP25.

In one embodiment, the compounds of Formula (I) have the structure of Formula (Ia):

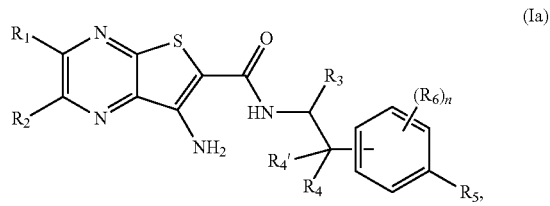

and pharmaceutically acceptable salts, hydrates, solvates, prodrugs, stereoisomers, and tautomers thereof.

In another embodiment, the compounds of Formula (I) have the structure of Formula (Ib):

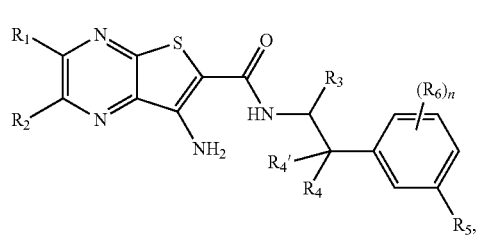

(Ib)

and pharmaceutically acceptable salts, hydrates, solvates, prodrugs, stereoisomers, and tautomers thereof.

In another embodiment, the compounds of Formula (I) have the structure of Formula (Ic):

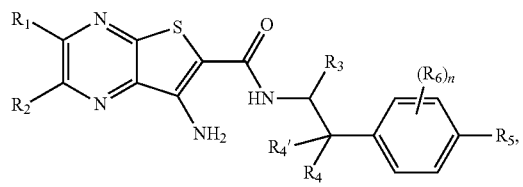

(Ic)

and pharmaceutically acceptable salts, hydrates, solvates, prodrugs, stereoisomers, and tautomers thereof.

In another embodiment, the compounds of Formula (I) have the structure of Formula (Id):

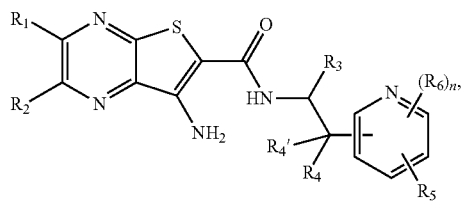

(Id)

and pharmaceutically acceptable salts, hydrates, solvates, prodrugs, stereoisomers, and tautomers thereof.

In another embodiment, the compounds of Formula (I) have the structure of Formula (Ie):

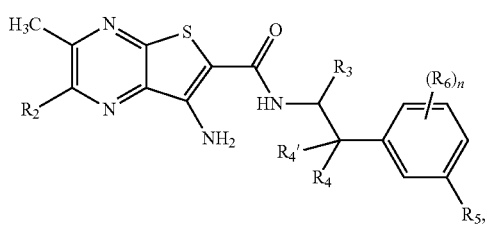

(Ie)

and pharmaceutically acceptable salts, hydrates, solvates, prodrugs, stereoisomers, and tautomers thereof.

In another embodiment, the compounds of Formula (I) have the structure of Formula (If):

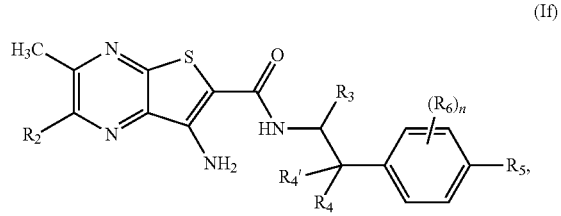

(If)

and pharmaceutically acceptable salts, hydrates, solvates, prodrugs, stereoisomers, and tautomers thereof.

In another embodiment, the compounds of Formula (I) have the structure of Formula (Ig):

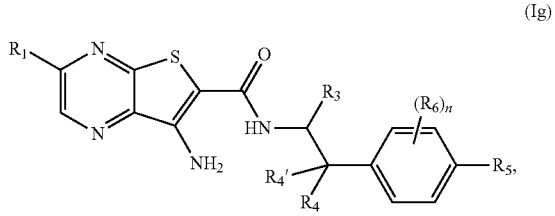

(Ig)

and pharmaceutically acceptable salts, hydrates, solvates, prodrugs, stereoisomers, and tautomers thereof.

In another embodiment, the compounds of Formula (I) have the structure of Formula

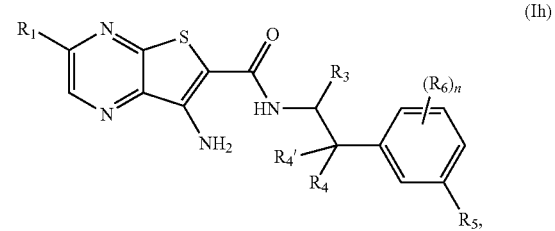

(Ih)

and pharmaceutically acceptable salts, hydrates, solvates, prodrugs, stereoisomers, and tautomers thereof.

In another embodiment, the compounds of Formula (I) have the structure of Formula (Ii):

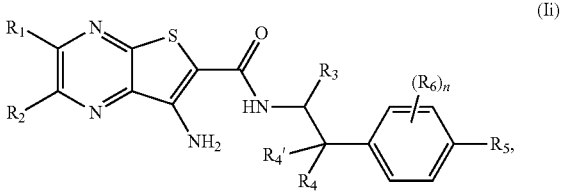

(Ii)

and pharmaceutically acceptable salts, hydrates, solvates, prodrugs, stereoisomers, and tautomers thereof.

In another embodiment, the compounds of Formula (I) have the structure of Formula (Ij):

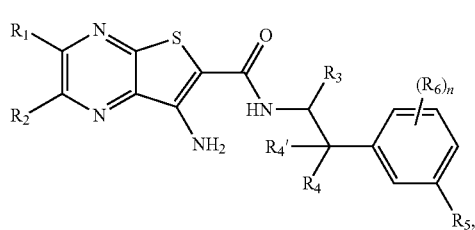

(Ij)

and pharmaceutically acceptable salts, hydrates, solvates, prodrugs, stereoisomers, and tautomers thereof.

In some embodiments of the Formulae above, X is $CR_6$. In another embodiment, X is N.

In some embodiments of the Formulae above, $R_1$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, or $-NR_9R_{10}$. In another embodiment, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_6)$ cycloalkyl, $-CN$, or $-NR_8R_9$. In yet another embodiment, $R_1$ is H, $(C_1-C_3)$ alkyl, $(C_1-C_3)$ alkoxy, $(C_1-C_3)$ haloalkyl, $(C_1-C_3)$ haloalkoxy, $(C_1-C_3)$ hydroxyalkyl, halogen, $(C_3-C_6)$ cycloalkyl, $-CN$, or $-NR_8R_9$. In yet another embodiment, $R_1$ is H, $(C_1-C_3)$ alkyl, $(C_1-C_3)$ alkoxy, $(C_1-C_3)$ haloalkyl, $(C_1-C_3)$ haloalkoxy, $(C_1-C_3)$ hydroxyalkyl, halogen, $(C_3-C_6)$ cycloalkyl, or $-NR_8R_9$. In yet another embodiment, $R_1$ is $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_6)$ cycloalkyl, $-CN$, or $-NR_8R_9$. In yet another embodiment, $R_1$ is $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_6)$ cycloalkyl, or $-NR_8R_9$. In yet another embodiment, $R_1$ is H or $(C_1-C_3)$ alkyl. In another embodiment, $R_1$ is $(C_1-C_3)$ alkyl. In yet another embodiment, $R_1$ is H, methyl, ethyl, n-propyl, or iso-propyl. In yet another embodiment, $R_1$ is H, methyl, or ethyl. In yet another embodiment, $R_1$ is methyl or ethyl.

In some embodiments of the Formulae above, $R_2$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_6)$ cycloalkyl, or $-NR_{10}R_{11}$. In another embodiment, $R_2$ is H, $(C_1-C_3)$ alkyl, $(C_1-C_3)$ alkoxy, $(C_1-C_3)$ haloalkyl, $(C_1-C_3)$ haloalkoxy, $(C_1-C_3)$ hydroxyalkyl, halogen, $(C_3-C_6)$ cycloalkyl, or $-NR_{10}R_{11}$. In yet another embodiment, $R_2$ is H, $(C_1-C_4)$ alkyl, $(C_1-C_4)$ haloalkyl, halogen, $(C_3-C_6)$ cycloalkyl, or $-NR_{10}R_{11}$. In another embodiment, $R_2$ is H, $(C_1-C_3)$ alkyl, $(C_1-C_3)$ haloalkyl, halogen, $(C_3-C_6)$ cycloalkyl, or $-NR_{10}R_{11}$. In yet another embodiment, $R_2$ is $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_6)$ cycloalkyl, or $-NR_{10}R_{11}$. In another embodiment, $R_2$ is H or halogen. In another embodiment, $R_2$ is H.

In another embodiment, $R_1$ and $R_2$ together form a $(C_4-C_8)$ cycloalkyl optionally substituted with one to three $R_{12}$. In yet another embodiment, $R_1$ and $R_2$ together form a $(C_4-C_6)$ cycloalkyl optionally substituted with one to three $R_{12}$.

In some embodiments of the Formulae above, at least one of $R_1$ or $R_2$ is not H.

In some embodiments of the Formulae above, $R_1$ is $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_6)$ cycloalkyl, or $-NR_8R_9$; and $R_2$ is H, $(C_1-C_3)$ alkyl, $(C_1-C_3)$ alkoxy, $(C_1-C_3)$ haloalkyl, $(C_1-C_3)$ haloalkoxy, $(C_1-C_3)$ hydroxyalkyl, halogen, $(C_3-C_6)$ cycloalkyl, or $-NR_{10}R_{11}$.

In some embodiments of the Formulae above, $R_3$ is H, $(C_1-C_3)$ alkyl, or $(C_1-C_3)$ haloalkyl. In another embodiment, $R_3$ is H or $(C_1-C_3)$ alkyl. In yet another embodiment, $R_3$ is H. In another embodiment, $R_3$ is H, methyl, ethyl, n-propyl, or iso-propyl. In yet another embodiment, $R_3$ is H or methyl.

In some embodiments of the Formulae above, $R_4$ is H, $(C_1-C_3)$ alkyl, halogen, or $(C_1-C_3)$ haloalkyl. In another embodiment, $R_4$ is H, halogen, or $(C_1-C_3)$ alkyl. In yet another embodiment, $R_4$ is H or $(C_1-C_3)$ alkyl. In yet another embodiment, $R_4$ is H. In another embodiment, $R_4$ is H, methyl, ethyl, n-propyl, or iso-propyl. In yet another embodiment, $R_4$ is H, F, $C_1$, methyl, ethyl, n-propyl, or iso-propyl. In another embodiment, $R_4$ is H, F, or methyl. In yet another embodiment, $R_4$ is H or methyl.

In some embodiments of the Formulae above, $R_4$ is H, $(C_1-C_3)$ alkyl, halogen, or $(C_1-C_3)$ haloalkyl. In another embodiment, $R_{4'}$ is H, halogen, or $(C_1-C_3)$ alkyl. In yet another embodiment, $R_{4'}$ is H or $(C_1-C_3)$ alkyl. In yet another embodiment, $R_{4'}$ is H. In another embodiment, $R_{4'}$ is H, methyl, ethyl, n-propyl, or iso-propyl. In yet another embodiment, $R_{4'}$ is H, fluoro, chloro, methyl, ethyl, n-propyl, or iso-propyl. In yet another embodiment, $R_{4'}$ is H, F, or methyl. In yet another embodiment, $R_4$ is H or methyl.

In some embodiments of the Formulae above, $R_5$ is $-(C_0-C_3)$ alkylene-C(O)OH, $-(C_0-C_3)$ alkylene-heterocycloalkyl, $-(C_0-C_3)$ alkylene-aryl, $-(C_0-C_3)$ alkylene-heteroaryl or $-N(R_7)-(C_0-C_3)$ alkylene-heterocycloalkyl, wherein the heterocycloalkyl, aryl and heteroaryl are optionally substituted with one to three $R_{13}$. In another embodiment, $R_5$ is $-(C_0-C_3)$ alkylene-C(O)OH, $-(C_0-C_3)$ alkylene-heterocycloalkyl, $-(C_0-C_3)$ alkylene-heteroaryl or $-N(R_7)-(C_0-C_3)$ alkylene-heterocycloalkyl, wherein the heterocycloalkyl and heteroaryl are optionally substituted with one to three $R_{13}$. In another embodiment, $R_5$ is $-(C_0-C_3)$ alkylene-heterocycloalkyl, $-(C_0-C_3)$ alkylene-heteroaryl or $-N(R_7)-(C_0-C_3)$ alkylene-heterocycloalkyl, wherein the heterocycloalkyl and heteroaryl are optionally substituted with one to three $R_{13}$. In another embodiment, $R_5$ is $-(C_0-C_3)$ alkylene-heterocycloalkyl, $-O$-heterocycloalkyl, $-(C_0-C_3)$ alkylene-heteroaryl or $-N(R_7)-(C_0-C_3)$ alkylene-heterocycloalkyl, wherein the heterocycloalkyl and heteroaryl are optionally substituted with one to three $R_{13}$. In another embodiment, $R_5$ is $-O$-heterocycloalkyl optionally substituted with one to three $R_3$.

In some embodiments of the Formulae above, $R_6$ is H, $(C_1-C_4)$ alkyl, $(C_1-C_4)$ alkoxy, $(C_1-C_4)$ haloalkyl, $(C_1-C_4)$ haloalkoxy, halogen, $-OH$, $-CN$, $(C_3-C_8)$ cycloalkyl, heterocycloalkyl, aryl, or heteroaryl, wherein the alkyl is optionally substituted with one or more $(C_1-C_4)$ alkoxy or $-OH$, and wherein the cycloalkyl, heterocycloalkyl, aryl, and heteroaryl are optionally substituted with one to three $R_{14}$. In another embodiment, $R_6$ is H, $(C_1-C_4)$ alkyl, $(C_1-C_4)$ alkoxy, $(C_1-C_4)$ haloalkyl, $(C_1-C_4)$ haloalkoxy, halogen, $-OH$, $-CN$, $(C_3-C_8)$ cycloalkyl, aryl, or heteroaryl, wherein the alkyl is optionally substituted with one or more $(C_1-C_4)$ alkoxy or $-OH$, and wherein the cycloalkyl, aryl, and heteroaryl are optionally substituted with one to three $R_{14}$.

In another embodiment, $R_5$ and $R_6$ together when on adjacent atoms form a $(C_3-C_8)$ cycloalkyl ring optionally substituted with one to three $R_{15}$. In yet another embodiment, $R_5$ and $R_6$ together when on adjacent atoms form a heterocycloalkyl ring optionally substituted with one to three $R_{15}$. In another embodiment, $R_5$ and $R_6$ together when on adjacent atoms form an aryl ring optionally substituted with one to three $R_{15}$. In yet another embodiment, $R_5$ and $R_6$ together when on adjacent atoms form a heteroaryl ring optionally substituted with one to three $R_{15}$.

In another embodiment, two $R_6$ together when on adjacent atoms form a $(C_3\text{-}C_8)$ cycloalkyl ring. In yet another embodiment, two $R_6$ together when on adjacent atoms form a heterocycloalkyl ring. In another embodiment, two $R_6$ together when on adjacent atoms form an aryl ring. In yet another embodiment, two $R_6$ together when on adjacent atoms form a heteroaryl ring.

In some embodiments of the Formulae above, $R_7$ is H or $(C_1\text{-}C_3)$ alkyl. In another embodiment, $R_7$ is H. In yet another embodiment, $R_7$ is $(C_1\text{-}C_3)$ alkyl. In another embodiment, $R_7$ is H, methyl, ethyl, n-propyl, or iso-propyl. In another embodiment, $R_7$ is H, methyl, or ethyl.

In some embodiments of the Formulae above, $R_8$ is H, $(C_1\text{-}C_3)$ alkyl, or —C(O)$(C_1\text{-}C_3)$ alkyl. In another embodiment, $R_8$ is H, $(C_1\text{-}C_3)$ alkyl, or —C(O)$(C_1\text{-}C_2)$ alkyl. In yet another embodiment, $R_8$ is H, methyl, ethyl, n-propyl, iso-propyl, —C(O)CH$_3$, or —C(O)CH$_2$CH$_3$.

In some embodiments of the Formulae above, $R_9$ is H, $(C_1\text{-}C_3)$ alkyl, or —C(O)$(C_1\text{-}C_3)$ alkyl. In another embodiment, $R_9$ is H, $(C_1\text{-}C_3)$ alkyl, or —C(O)$(C_1\text{-}C_2)$ alkyl. In yet another embodiment, $R_9$ is H, methyl, ethyl, n-propyl, iso-propyl, —C(O)CH$_3$, or —C(O)CH$_2$CH$_3$.

In some embodiments of the Formulae above, $R_{10}$ is H, $(C_1\text{-}C_3)$ alkyl, or —C(O)$(C_1\text{-}C_3)$ alkyl. In another embodiment, $R_{10}$ is H, $(C_1\text{-}C_3)$ alkyl, or —C(O)$(C_1\text{-}C_2)$ alkyl. In yet another embodiment, $R_{10}$ is H, methyl, ethyl, n-propyl, iso-propyl, —C(O)CH$_3$, or —C(O)CH$_2$CH$_3$. In another embodiment, $R_{10}$ is H.

In some embodiments of the Formulae above, $R_{11}$ is H, $(C_1\text{-}C_3)$ alkyl, or —C(O)$(C_1\text{-}C_3)$ alkyl. In another embodiment, $R_{11}$ is H, $(C_1\text{-}C_3)$ alkyl, or —C(O)$(C_1\text{-}C_2)$ alkyl. In yet another embodiment, $R_{11}$ is H, methyl, ethyl, n-propyl, iso-propyl, —C(O)CH$_3$, or —C(O)CH$_2$CH$_3$. In another embodiment, $R_{11}$ is H.

In some embodiments of the Formulae above, $R_{12}$ is $(C_1\text{-}C_3)$ alkyl, $(C_1\text{-}C_3)$ alkoxy, $(C_1\text{-}C_3)$ haloalkyl, $(C_1\text{-}C_3)$ haloalkoxy, halogen, or —OH. In another embodiment, $R_{12}$ is $(C_1\text{-}C_3)$ alkyl, $(C_1\text{-}C_3)$ haloalkyl, halogen, or —OH. In yet another embodiment, $R_{12}$ is $(C_1\text{-}C_3)$ alkyl, halogen, or —OH. In another embodiment, $R_{12}$ is $(C_1\text{-}C_3)$ alkyl or —OH. In yet another embodiment, $R_{12}$ is —OH.

In some embodiments of the Formulae above, $R_{13}$ is $(C_1\text{-}C_4)$ alkyl, $(C_1\text{-}C_4)$ alkoxy, $(C_1\text{-}C_4)$ haloalkyl, $(C_1\text{-}C_4)$ haloalkoxy, $(C_1\text{-}C_4)$ hydroxyalkyl, halogen, $(C_3\text{-}C_8)$ cycloalkyl, —C(O)NR$_{18}$R$_{19}$, —S(O)$_2$(C$_1$-C$_6$) alkyl, —OH, or —NR$_{16}$R$_{17}$, wherein the alkyl is optionally substituted with one to three substituents independently selected from $(C_1\text{-}C_6)$ alkoxy, OH, and heterocycloalkyl. In another embodiment, $R_{13}$ is $(C_1\text{-}C_4)$ alkyl, $(C_1\text{-}C_4)$ alkoxy, $(C_1\text{-}C_4)$ hydroxyalkyl, halogen, $(C_3\text{-}C_8)$ cycloalkyl, —C(O)NR$_{18}$R$_{19}$, —S(O)$_2$(C$_1$-C$_6$) alkyl, —OH, or —NR$_{16}$R$_{17}$, wherein the alkyl is optionally substituted with one to three substituents independently selected from $(C_1\text{-}C_6)$ alkoxy, OH, and heterocycloalkyl. In yet another embodiment, $R_{13}$ is $(C_1\text{-}C_4)$ alkyl, $(C_1\text{-}C_4)$ alkoxy, $(C_1\text{-}C_4)$ hydroxyalkyl, halogen, $(C_3\text{-}C_8)$ cycloalkyl, or —NR$_{16}$R$_{17}$, wherein the alkyl is optionally substituted with one to three substituents independently selected from $(C_1\text{-}C_6)$ alkoxy, OH, and heterocycloalkyl. In another embodiment, $R_{13}$ is $(C_1\text{-}C_4)$ alkyl, $(C_3\text{-}C_8)$ cycloalkyl, —C(O)NR$_{18}$R$_{19}$, —S(O)$_2$(C$_1$-C$_6$) alkyl, —OH, or —NR$_{16}$R$_{17}$, wherein the alkyl is optionally substituted with one to three substituents independently selected from $(C_1\text{-}C_6)$ alkoxy, OH, and heterocycloalkyl. In yet another embodiment, $R_{13}$ is $(C_1\text{-}C_4)$ alkyl, $(C_3\text{-}C_8)$ cycloalkyl, or —NR$_{16}$R$_{17}$, wherein the alkyl is optionally substituted with one to three substituents independently selected from $(C_1\text{-}C_6)$ alkoxy, OH, and heterocycloalkyl.

In another embodiment, two $R_{13}$ together when attached to the same carbon can form —C═(O) when $R_5$ is —(C$_0$-C$_3$) alkylene-heterocycloalkyl or —N(R$_7$)—(C$_0$-C$_3$) alkylene-heterocycloalkyl. In yet another embodiment, two $R_{13}$ together when attached to the same atom form a $(C_3\text{-}C_8)$ spirocycloalkyl optionally substituted with one to three $R_{20}$ when $R_5$ is —(C$_0$-C$_3$) alkylene-heterocycloalkyl or —N(R$_7$)—(C$_0$-C$_3$) alkylene-heterocycloalkyl. In another embodiment, two $R_{13}$ together when attached to the same atom form a $(C_3\text{-}C_8)$ spiroheterocycloalkyl optionally substituted with one to three $R_{20}$ when $R_5$ is —(C$_0$-C$_3$) alkylene-heterocycloalkyl or —N(R$_7$)—(C$_0$-C$_3$) alkylene-heterocycloalkyl. In another embodiment, two $R_{13}$ together when on adjacent atoms form a heterocycloalkyl ring optionally substituted with one to three $R_{20}$. In another embodiment, two $R_{13}$ together when on adjacent atoms form a heteroaryl ring optionally substituted with one to three $R_{20}$. In another embodiment, two $R_{13}$ together with the atoms to which they are attached can form a bridged heterocycloalkyl ring optionally substituted with one to three $R_{20}$ when $R_5$ is —(C$_0$-C$_3$) alkylene-heterocycloalkyl or —N(R$_7$)—(C$_0$-C$_3$) alkylene-heterocycloalkyl.

In another embodiment, two $R_{13}$ together when attached to the same carbon can form —C═(O) when $R_5$ is —(C$_0$-C$_3$) alkylene-heterocycloalkyl, —O-heterocycloalkyl, or —N(R$_7$)—(C$_0$-C$_3$) alkylene-heterocycloalkyl. In yet another embodiment, two $R_{13}$ together when attached to the same atom form a $(C_3\text{-}C_8)$ spirocycloalkyl optionally substituted with one or more $R_{20}$ when $R_5$ is —(C$_0$-C$_3$) alkylene-heterocycloalkyl, —O-heterocycloalkyl, or —N(R$_7$)—(C$_0$-C$_3$) alkylene-heterocycloalkyl. In another embodiment, two $R_{13}$ together when attached to the same atom form a $(C_3\text{-}C_8)$ spiroheterocycloalkyl optionally substituted with one or more $R_{20}$ when $R_5$ is —(C$_0$-C$_3$) alkylene-heterocycloalkyl, —O-heterocycloalkyl, or —N(R$_7$)—(C$_0$-C$_3$) alkylene-heterocycloalkyl. In another embodiment, two $R_{13}$ together with the atoms to which they are attached can form a bridged heterocycloalkyl ring optionally substituted with one or more $R_{20}$ when $R_5$ is —(C$_0$-C$_3$) alkylene-heterocycloalkyl, —O-heterocycloalkyl, or —N(R$_7$)—(C$_0$-C$_3$) alkylene-heterocycloalkyl.

In some embodiments of the Formulae above, $R_{14}$ is $(C_1\text{-}C_4)$ alkyl, $(C_1\text{-}C_4)$ alkoxy, $(C_1\text{-}C_4)$ haloalkyl, $(C_1\text{-}C_4)$ haloalkoxy, halogen, cycloalkyl, heterocycloalkyl, or —C(O)-heterocycloalkyl, wherein the alkyl is optionally substituted with one to three substituents independently selected from $(C_1\text{-}C_4)$ alkoxy and —OH. In another embodiment, $R_{14}$ is $(C_1\text{-}C_4)$ alkyl, $(C_1\text{-}C_4)$ haloalkyl, halogen, heterocycloalkyl, or —C(O)-heterocycloalkyl, wherein the alkyl is optionally substituted with one to three substituents independently selected from $(C_1\text{-}C_4)$ alkoxy and —OH.

In some embodiments of the Formulae above, $R_{15}$ is $(C_1\text{-}C_4)$ alkyl, $(C_1\text{-}C_4)$ alkoxy, $(C_1\text{-}C_4)$ haloalkyl, $(C_1\text{-}C_4)$ haloalkoxy, halogen, —OH, —CN, —C(O)OH, or —C(O)O(C$_1$-C$_4$) alkyl. In another embodiment, $R_{15}$ is $(C_1\text{-}C_4)$ alkyl, $(C_1\text{-}C_4)$ haloalkyl, halogen, —OH, —CN, —C(O)OH, or —C(O)O(C$_1$-C$_4$) alkyl. In yet another embodiment, $R_{15}$ is $(C_1\text{-}C_4)$ alkyl, halogen, —OH, —CN, —C(O)OH, or —C(O)O(C$_1$-C$_4$) alkyl. In another embodiment, $R_{15}$ is $(C_1\text{-}C_4)$ alkyl, —OH, —C(O)OH, or —C(O)O(C$_1$-C$_4$) alkyl. In another embodiment, $R_{15}$ is —C(O)OH, or —C(O)O(C$_1$-C$_4$) alkyl.

In some embodiments of the Formulae above, $R_{16}$ is H, $(C_1\text{-}C_4)$ alkyl, $(C_3\text{-}C_8)$ cycloalkyl, —$CH_2C(O)NH_2$, —$S(O)_2$ $(C_1\text{-}C_4)$ alkyl, —$S(O)_2(C_6\text{-}C_{10})$ aryl or —$C(O)(C_1\text{-}C_4)$ alkyl. In another embodiment, $R_{16}$ is H, $(C_1\text{-}C_4)$ alkyl, $(C_3\text{-}C_6)$ cycloalkyl, —$CH_2C(O)NH_2$, —$S(O)_2(C_1\text{-}C_4)$ alkyl, —$S(O)_2(C_6\text{-}C_{10})$ aryl, or —$C(O)(C_1\text{-}C_4)$ alkyl. In yet another embodiment, $R_{16}$ is H, $(C_1\text{-}C_4)$ alkyl or $(C_3\text{-}C_6)$ cycloalkyl. In another embodiment, $R_{16}$ is H, $(C_1\text{-}C_4)$ alkyl —$CH_2C(O)NH_2$, —$S(O)_2(C_1\text{-}C_4)$ alkyl, —$S(O)_2(C_6\text{-}C_{10})$ aryl, or —$C(O)(C_1\text{-}C_4)$ alkyl.

In some embodiments of the Formulae above, $R_{17}$ is H, $(C_1\text{-}C_4)$ alkyl, $(C_3\text{-}C_8)$ cycloalkyl, —$CH_2C(O)NH_2$, —$S(O)_2$ $(C_1\text{-}C_4)$ alkyl, —$S(O)_2(C_6\text{-}C_{10})$ aryl or —$C(O)(C_1\text{-}C_4)$ alkyl. In another embodiment, $R_{17}$ is H, $(C_1\text{-}C_4)$ alkyl, $(C_3\text{-}C_6)$ cycloalkyl, —$CH_2C(O)NH_2$, —$S(O)_2(C_1\text{-}C_4)$ alkyl, —$S(O)_2(C_6\text{-}C_{10})$ aryl, or —$C(O)(C_1\text{-}C_4)$ alkyl. In yet another embodiment, $R_{17}$ is H, $(C_1\text{-}C_4)$ alkyl or $(C_3\text{-}C_6)$ cycloalkyl. In another embodiment, $R_{17}$ is H, $(C_1\text{-}C_4)$ alkyl —$CH_2C(O)NH_2$, —$S(O)_2(C_1\text{-}C_4)$ alkyl, —$S(O)_2(C_6\text{-}C_{10})$ aryl, or —$C(O)(C_1\text{-}C_4)$ alkyl.

In some embodiments of the Formulae above, $R_{18}$ is H or $(C_1\text{-}C_3)$ alkyl. In another embodiment, $R_{18}$ is H, methyl, ethyl, n-propyl, or iso-propyl.

In some embodiments of the Formulae above, $R_{19}$ is H or $(C_1\text{-}C_3)$ alkyl. In another embodiment, $R_{19}$ is H, methyl, ethyl, n-propyl, or iso-propyl.

In some embodiments of the Formulae above, $R_{20}$ is $(C_1\text{-}C_3)$ alkyl, $(C_1\text{-}C_3)$ alkoxy, $(C_1\text{-}C_3)$ haloalkyl, $(C_1\text{-}C_3)$ haloalkoxy, or halogen. In another embodiment, $R_{20}$ is $(C_1\text{-}C_2)$ alkyl, $(C_1\text{-}C_2)$ alkoxy, $(C_1\text{-}C_2)$ haloalkyl, $(C_1\text{-}C_2)$ haloalkoxy, or halogen. In yet another embodiment, $R_{20}$ is $(C_1\text{-}C_2)$ alkyl, $(C_1\text{-}C_2)$ haloalkyl, or halogen. In another embodiment, $R_{20}$ is $(C_1\text{-}C_2)$ alkyl, or $(C_1\text{-}C_2)$ haloalkyl. In another embodiment, $R_{20}$ is $(C_1\text{-}C_3)$ alkyl. In another embodiment, $R_{20}$ is methyl, ethyl, n-propyl, or iso-propyl.

In another embodiment, two $R_{20}$ together when attached to the same carbon form —C=(O).

In some embodiments of the Formulae above, n is 0, 1, or 2. In another embodiment, n is 0 or 1. In yet another embodiment, n is 1, 2, or 3. In another embodiment, n is 1 or 2. In another embodiment, n is 2 or 3. In another embodiment, n is 0. In another embodiment, n is 1. In another embodiment, n is 2. In another embodiment, n is 3.

In some embodiments of the Formulae above,
$R_5$ is —$(C_0\text{-}C_3)$ alkylene-$C(O)OH$, —$(C_0\text{-}C_3)$ alkylene-heterocycloalkyl, —$(C_0\text{-}C_3)$ alkylene-aryl, —$(C_0\text{-}C_3)$ alkylene-heteroaryl or —$N(R_7)$—$(C_0\text{-}C_3)$ alkylene-heterocycloalkyl, wherein the heterocycloalkyl, aryl and heteroaryl are optionally substituted with one or more $R_{13}$; and
each $R_{13}$ is independently at each occurrence $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, $(C_1\text{-}C_6)$ hydroxyalkyl, halogen, $(C_3\text{-}C_8)$ cycloalkyl, —$C(O)NR_{18}R_{19}$, —$S(O)_2(C_1\text{-}C_6)$ alkyl, —OH, or —$NR_{16}R_{17}$, wherein the alkyl is optionally substituted with one or more substituents independently selected from $(C_1\text{-}C_6)$ alkoxy, OH, and heterocycloalkyl; or
two $R_{13}$ together when attached to the same carbon can form —C=(O) when $R_5$ is —$(C_0\text{-}C_3)$ alkylene-heterocycloalkyl or —$N(R_7)$—$(C_0\text{-}C_3)$ alkylene-heterocycloalkyl; or two $R_{13}$ together when attached to the same atom form a $(C_3\text{-}C_8)$ spirocycloalkyl optionally substituted with one or more $R_{20}$ when $R_5$ is —$(C_0\text{-}C_3)$ alkylene-heterocycloalkyl or —$N(R_7)$—$(C_0\text{-}C_3)$ alkylene-heterocycloalkyl; or two $R_{13}$ together when attached to the same atom form a $(C_3\text{-}C_8)$ spiroheterocycloalkyl optionally substituted with one or more $R_{20}$ when $R_5$ is —$(C_0\text{-}C_3)$ alkylene-heterocycloalkyl or —$N(R_7)$—$(C_0\text{-}C_3)$ alkylene-heterocycloalkyl; or two $R_{13}$ together when on adjacent atoms form a heterocycloalkyl ring optionally substituted with one or more $R_{20}$; or two $R_{13}$ together when on adjacent atoms form a heteroaryl ring optionally substituted with one or more $R_{20}$; or two $R_{13}$ together with the atoms to which they are attached can form a bridged heterocycloalkyl ring optionally substituted with one or more $R_{20}$ when $R_5$ is —$(C_0\text{-}C_3)$ alkylene-heterocycloalkyl or —$N(R_7)$—$(C_0\text{-}C_3)$ alkylene-heterocycloalkyl.

In some embodiments of the Formulae above, X is CH.

In some embodiments of the Formulae above, $R_3$ is H or $CH_3$ and $R_4$ is H or $CH_3$.

In some embodiments of the Formulae above, $R_3$ is H or $CH_3$, $R_4$ is H or $CH_3$, and $R_{4'}$ is H, fluoro, or $CH_3$.

In some embodiments of the Formulae above, $R_2$ is H, $(C_1\text{-}C_6)$ alkyl, $(C_1\text{-}C_6)$ haloalkyl, halogen, $(C_3\text{-}C_8)$ cycloalkyl, or —$NH_2$.

In some embodiments of the Formulae above, $R_1$ and $R_2$ together form a $(C_3\text{-}C_8)$ cycloalkyl optionally substituted with one or more $R_{12}$.

In some embodiments of the Formulae above, $R_1$ is H and $R_2$ is $(C_1\text{-}C_6)$ alkyl.

In some embodiments of the Formulae above, $R_1$ is $(C_1\text{-}C_6)$ alkyl and $R_2$ is H.

In some embodiments of the Formulae above, only one of $R_1$ or $R_2$ is H.

In some embodiments of the Formulae above, $R_1$ is $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, $(C_1\text{-}C_6)$ hydroxyalkyl, halogen, $(C_3\text{-}C_8)$ cycloalkyl, —CN, or —$NR_8R_9$ and $R_2$ is H, $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, $(C_1\text{-}C_6)$ hydroxyalkyl, halogen, $(C_3\text{-}C_8)$ cycloalkyl, or —$NR_{10}R_{11}$.

In some embodiments of the Formulae above, $R_1$ is H, $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, $(C_1\text{-}C_6)$ hydroxyalkyl, halogen, $(C_3\text{-}C_8)$ cycloalkyl, —CN, or —$NR_8R_9$ and $R_2$ is $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, $(C_1\text{-}C_6)$ hydroxyalkyl, halogen, $(C_3\text{-}C_8)$ cycloalkyl, or —$NR_{10}R_{11}$.

In some embodiments of the Formulae above, one of $R_1$ or $R_2$ is H and the other is $(C_1\text{-}C_6)$ alkyl.

In another embodiment, $R_1$ is H, $(C_1\text{-}C_4)$ alkyl, $(C_1\text{-}C_4)$ alkoxy, $(C_1\text{-}C_4)$ haloalkyl, $(C_1\text{-}C_4)$ haloalkoxy, $(C_1\text{-}C_4)$ hydroxyalkyl, halogen, $(C_3\text{-}C_6)$ cycloalkyl, or —$NR_8R_9$; and $R_2$ is $(C_1\text{-}C_3)$ alkyl, $(C_1\text{-}C_3)$ alkoxy, $(C_1\text{-}C_3)$ haloalkyl, $(C_1\text{-}C_3)$ haloalkoxy, $(C_1\text{-}C_3)$ hydroxyalkyl, halogen, $(C_3\text{-}C_6)$ cycloalkyl, or —$NR_{10}R_{11}$.

In some embodiments of the Formulae above, X is $CR_6$. In another embodiment, X is $CR_6$ and $R_1$ is H, $(C_1\text{-}C_4)$ alkyl, $(C_1\text{-}C_4)$ alkoxy, $(C_1\text{-}C_4)$ haloalkyl, $(C_1\text{-}C_4)$ haloalkoxy, $(C_1\text{-}C_4)$ hydroxyalkyl, halogen, $(C_3\text{-}C_8)$ cycloalkyl, or —$NR_8R_9$. In yet another embodiment, X is $CR_6$, $R_1$ is H, $(C_1\text{-}C_4)$ alkyl, $(C_1\text{-}C_4)$ alkoxy, $(C_1\text{-}C_4)$ haloalkyl, $(C_1\text{-}C_4)$ haloalkoxy, $(C_1\text{-}C_4)$ hydroxyalkyl, halogen, $(C_3\text{-}C_8)$ cycloalkyl, or —$NR_8R_9$, and $R_2$ is H, $(C_1\text{-}C_4)$ alkyl, $(C_1\text{-}C_4)$ haloalkyl, halogen, $(C_3\text{-}C_8)$ cycloalkyl, or —$NR_{10}R_{11}$. In another embodiment, X is $CR_6$, $R_1$ is H, $(C_1\text{-}C_4)$ alkyl, $(C_1\text{-}C_4)$ alkoxy, $(C_1\text{-}C_4)$ haloalkyl, $(C_1\text{-}C_4)$ haloalkoxy, $(C_1\text{-}C_4)$ hydroxyalkyl, halogen, $(C_3\text{-}C_8)$ cycloalkyl, or —$NR_8R_9$, $R_2$ is H, $(C_1\text{-}C_4)$ alkyl, $(C_1\text{-}C_4)$ haloalkyl, halogen, $(C_3\text{-}C_8)$ cycloalkyl, or —$NR_{10}R_{11}$, and $R_3$ is H or $(C_1\text{-}C_3)$ alkyl. In another embodiment, X is $CR_6$, $R_1$ is H, $(C_1\text{-}C_4)$ alkyl, $(C_1\text{-}C_4)$ alkoxy, $(C_1\text{-}C_4)$ haloalkyl, $(C_1\text{-}C_4)$ haloalkoxy, $(C_1\text{-}C_4)$ hydroxyalkyl, halogen, $(C_3\text{-}C_8)$ cycloalkyl, or —$NR_8R_9$, $R_2$ is H, $(C_1\text{-}C_4)$ alkyl, $(C_1\text{-}C_4)$ haloalkyl, halogen, $(C_3\text{-}C_8)$ cycloalkyl, or —$NR_{10}R_{11}$, $R_3$ is H or $(C_1\text{-}C_3)$ alkyl, and $R_4$ is H or $(C_1\text{-}C_3)$ alkyl. In another embodiment, X is $CR_6$, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, $R_3$ is H or $(C_1-C_3)$ alkyl, $R_4$ is H or $(C_1-C_3)$ alkyl, and $R_{4'}$ is H or $(C_1-C_3)$ alkyl.

In another embodiment, X is $CR_6$, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, $R_3$ is H or $(C_1-C_3)$ alkyl, $R_4$ is H or $(C_1-C_3)$ alkyl, $R_{4'}$ is H or $(C_1-C_3)$ alkyl, and $R_5$ is $-(C_0-C_3)$ alkylene-heterocycloalkyl optionally substituted with one or more $R_{13}$.

In another embodiment, X is $CR_6$, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, $R_3$ is H or $(C_1-C_3)$ alkyl, $R_4$ is H or $(C_1-C_3)$ alkyl, $R_{4'}$ is H or $(C_1-C_3)$ alkyl, and $R_5$ is $-(C_0-C_3)$ alkylene-C(O)OH.

In another embodiment, X is $CR_6$, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen. $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, $R_3$ is H or $(C_1-C_3)$ alkyl, $R_4$ is H or $(C_1-C_4)$ alkyl, $R_{4'}$ is H or $(C_1-C_3)$ alkyl, and $R_5$ is $-(C_0-C_3)$ alkylene-heteroaryl optionally substituted with one or more $R_{13}$.

In another embodiment, X is $CR_6$, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen. $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, $R_3$ is H or $(C_1-C_3)$ alkyl, $R_4$ is H or $(C_1-C_3)$ alkyl, $R_{4'}$ is H or $(C_1-C_3)$ alkyl, and $R_5$ is $-N(R_7)-(C_0-C_3)$ alkylene-heterocycloalkyl optionally substituted with one or more $R_{13}$.

In another embodiment, X is $CR_6$, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen. $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, $R_3$ is H or $(C_1-C_3)$ alkyl, $R_4$ is H or $(C_1-C_3)$ alkyl, $R_{4'}$ is H or $(C_1-C_3)$ alkyl, and $R_5$ is $-(C_0-C_3)$ alkylene-aryl optionally substituted with one or more $R_{13}$.

In another embodiment, X is $CR_6$, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen. $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, $R_3$ is H or $(C_1-C_3)$ alkyl, $R_4$ is H or $(C_1-C_3)$ alkyl, $R_{4'}$ is H or $(C_1-C_3)$ alkyl, and $R_5$ and $R_6$ together when on adjacent atoms form a $(C_4-C_8)$ cycloalkyl ring optionally substituted with one or more $R_{15}$.

In another embodiment, X is $CR_6$, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, $R_3$ is H or $(C_1-C_3)$ alkyl, $R_4$ is H or $(C_1-C_3)$ alkyl, $R_{4'}$ is H or $(C_1-C_3)$ alkyl, and $R_5$ and $R_6$ together when on adjacent atoms form a heterocycloalkyl ring optionally substituted with one or more $R_{15}$.

In some embodiments of the Formulae above, X is N. In another embodiment, X is N and $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_8)$ cycloalkyl, or $-NR_8R_9$. In yet another embodiment, X is N, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_8)$ cycloalkyl, or $-NR_8R_9$, and $R_2$ is H, $(C_1-C_4)$ alkyl, $(C_1-C_4)$ haloalkyl, halogen, $(C_3-C_8)$ cycloalkyl, or $-NR_{10}R_{11}$. In another embodiment, X is N, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, and $R_3$ is H or $(C_1-C_3)$ alkyl. In another embodiment, X is N, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, $R_3$ is H or $(C_1-C_3)$ alkyl, and $R_4$ is H or $(C_1-C_3)$ alkyl. In yet another embodiment, X is N, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, $R_3$ is H or $(C_1-C_3)$ alkyl, $R_4$ is H or $(C_1-C_3)$ alkyl, and $R_{4'}$ is H or $(C_1-C_3)$ alkyl.

In another embodiment, X is N, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, $R_3$ is H or $(C_1-C_3)$ alkyl, $R_4$ is H or $(C_1-C_3)$ alkyl, $R_{4'}$ is H or $(C_1-C_3)$ alkyl, and $R_5$ is $-(C_0-C_3)$ alkylene-heterocycloalkyl optionally substituted with one or more $R_{13}$.

In another embodiment, X is N, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, $R_3$ is H or $(C_1-C_3)$ alkyl, $R_4$ is H or $(C_1-C_3)$ alkyl, $R_{4'}$ is H or $(C_1-C_3)$ alkyl, and $R_5$ is $-(C_0-C_3)$ alkylene-C(O)OH.

In another embodiment, X is N, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, $R_3$ is H or $(C_1-C_3)$ alkyl, $R_4$ is H or $(C_1-C_3)$ alkyl, $R_{4'}$ is H or $(C_1-C_3)$ alkyl, and $R_5$ is $-(C_0-C_3)$ alkylene-heteroaryl optionally substituted with one or more $R_{13}$.

In another embodiment, X is N, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen. $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, $R_3$ is H or $(C_1-C_3)$ alkyl, $R_4$ is H or $(C_1-C_3)$ alkyl, $R_{4'}$ is H or $(C_1-C_3)$ alkyl, and $R_5$ is $-N(R_7)-(C_0-C_3)$ alkylene-heterocycloalkyl optionally substituted with one or more $R_{13}$.

In another embodiment, X is N, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen. $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, $R_3$ is H or $(C_1-C_3)$ alkyl, $R_4$ is H or $(C_1-C_3)$ alkyl, $R_{4'}$ is H or $(C_1-C_3)$ alkyl, and $R_5$ is $-(C_0-C_3)$ alkylene-aryl optionally substituted with one or more $R_{13}$.

In another embodiment, X is N, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen. $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, $R_3$ is H or $(C_1-C_3)$ alkyl, $R_4$ is H or $(C_1-C_3)$ alkyl, $R_{4'}$ is H or $(C_1-C_3)$ alkyl, and $R_5$ and $R_6$ together when on adjacent atoms form a $(C_4-C_8)$ cycloalkyl ring optionally substituted with one or more $R_{15}$.

In another embodiment, X is N, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_8)$ cycloalkyl, or $-NR_8R_9$, $R_2$ is H, $(C_1-C_4)$ alkyl, $(C_1-C_4)$ haloalkyl, halogen, $(C_3-C_8)$ cycloalkyl, or $-NR_{10}R_{11}$, $R_3$ is H or $(C_1-C_3)$ alkyl, $R_4$ is H or $(C_1-C_3)$ alkyl, $R_{4'}$ is H or $(C_1-C_3)$ alkyl, and $R_5$ and $R_6$ together when on adjacent atoms form a heterocycloalkyl ring optionally substituted with one or more $R_{15}$ Non-limiting illustrative compounds of the disclosure include:

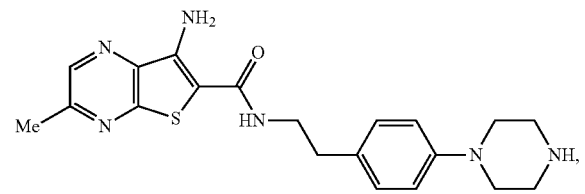

I-1. 7-amino-3-methyl-N-(4-(piperazin-1-yl)phenethyl)thieno[2,3-b]pyrazine-6-carboxamide

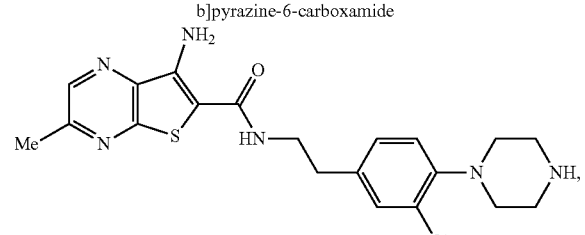

I-2. 7-amino-N-(3-chloro-4-(piperazin-1-yl)phenethyl)-3-methylthieno[2,3-b]pyrazine-6-carboxamide

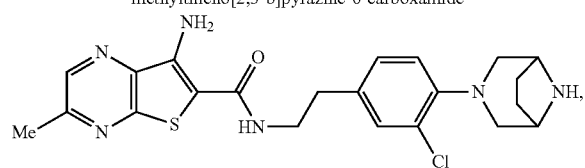

I-3. N-(4-(3,8-diazabicyclo[3.2.1]octan-3-yl)-3-chlorophenethyl-7-amino-3-methylthieno[2,3-b]pyrazine-6-carboxamide

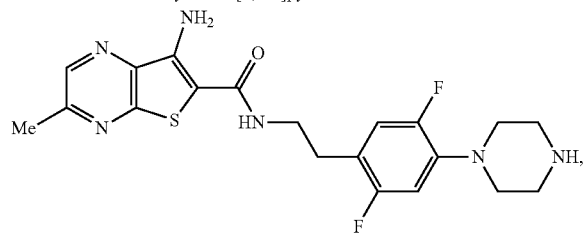

I-4. 7-amino-N-(2,5-difluoro-4-piperazin-1-yl)phenethyl)-3-methylthieno[2,3-b]pyrazine-6-carboxamide

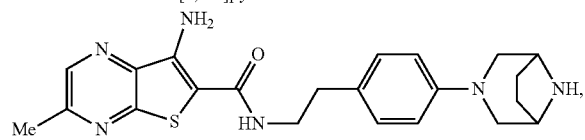

I-5. N-(4-(3,8-diazabicyclo[3.2.1]octan-3-yl)phenethyl)-7-amino-3-methylthieno[2,3-b]pyrazine-6-carboxamide

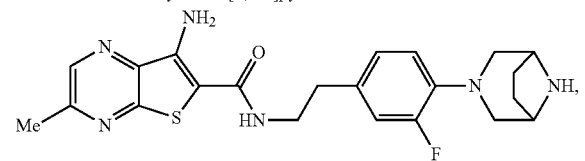

I-6. N-(4-(3,8-diazabicyclo[3.2.1]octan-3-yl)-3-fluorophenethyl)-7-amino-3-methylthieno[2,3-b]pyrazine-6-carboxamide

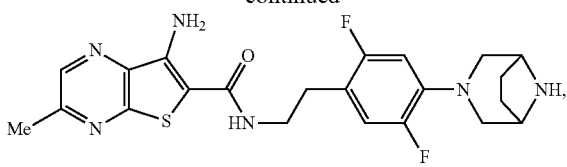

I-7. N-(4-(3,8-diazabicyclo[3.2.1]octan-3-yl)-2,5-difluorophenethyl)-7-amino-3-methylthieno[2,3-b]pyrazine-6-carboxamide

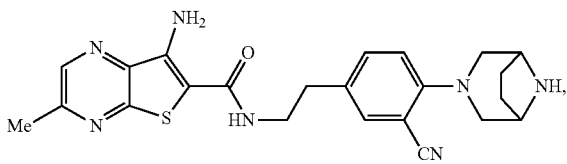

I-9. N-(4-(3,8-diazabicyclo[3.2.1]octan-3-yl)-3-cyanophenethyl)-7-amino-3-methylthieno[2,3-b]pyrazine-6-carboxamide

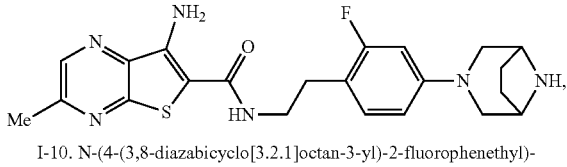

I-10. N-(4-(3,8-diazabicyclo[3.2.1]octan-3-yl)-2-fluorophenethyl)-7-amino-3-methylthieno[2,3-b]pyrazine-6-carboxamide

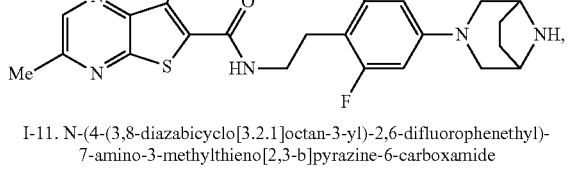

I-11. N-(4-(3,8-diazabicyclo[3.2.1]octan-3-yl)-2,6-difluorophenethyl)-7-amino-3-methylthieno[2,3-b]pyrazine-6-carboxamide

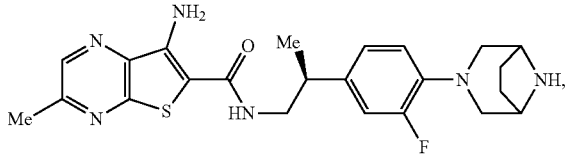

I-12. N-((2S)-2-(4-(3,8-diazabicyclo[3.2.1]octan-3-yl)-3-fluorophenyl)propyl)-7-amino-3-methylthieno[2,3-b]pyrazine-6-carboxamide

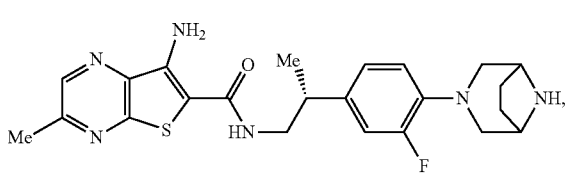

I-13. N-((2R)-2-(4-(3,8-diazabicyclo[3.2.1]octan-3-yl)-3-fluorophenyl)propyl)-7-amino-3-methylthieno[2,3-b]pyrazine-6-carboxamide

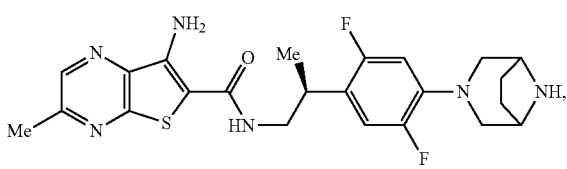

I-14. N-((2S)-2-(4-(3,8-diazabicyclo[3.2.1]octan-3-yl)-2,5-difluorophenyl)propyl)-7-amino-3-methylthieno[2,3-b]pyrazine-6-carboxamide

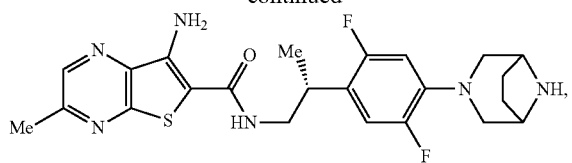

I-15. N-((2R)-2-(4-(3,8-diazabicyclo[3.2.1]octan-3-yl)-2,5-difluorophenyl)propyl)-7-amino-3-methylthieno[2,3-b]pyrazine-6-carboxamide

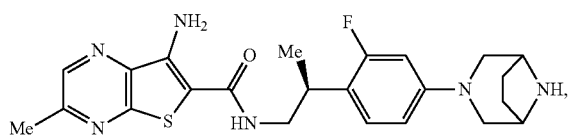

I-16. N-((2S)-2-(4-(3,8-diazabicyclo[3.2.1]octan-3-yl)-2-fluorophenyl)propyl)-7-amino-3-methylthieno[2,3-b]pyrazine-6-carboxamide

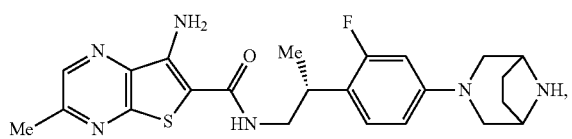

I-17. N-((2R)-2-(4-(3,8-diazabicyclo[3.2.1]octan-3-yl)-2-fluorophenyl)propyl)-7-amino-3-methylthieno[2,3-b]pyrazine-6-carboxamide

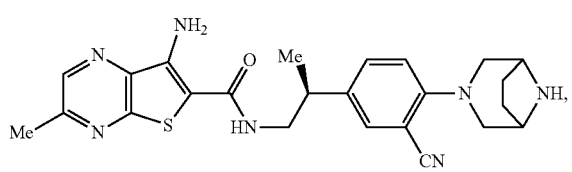

I-18. N-((2S)-2-(4-(3,8-diazabicyclo[3.2.1]octan-3-yl)-3-cyanophenyl)propyl)-7-amino-3-methylthieno[2,3-b]pyrazine-6-carboxamide

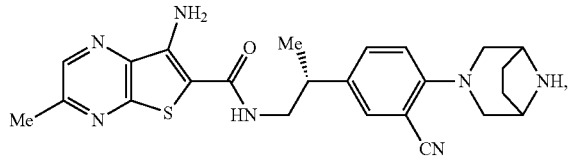

I-19. N-((2R)-2-(4-(3,8-diazabicyclo[3.2.1]octan-3-yl)-3-cyanophenyl)propyl)-7-amino-3-methylthieno[2,3-b]pyrazine-6-carboxamide

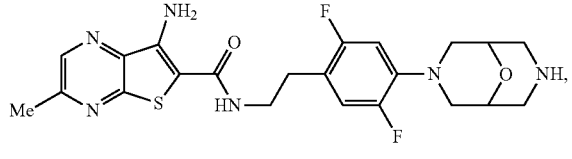

I-20. N-(4-(9-oxa-3,7-diazabicyclo[3.3.1]nonan-3-yl)-2,5-difluorophenethyl)-7-amino-3-methylthieno[2,3-b]pyrazine-6-carboxamide

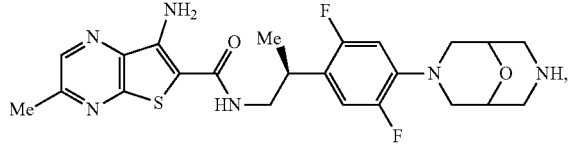

I-21. N-((2R)-2-(4-(9-oxa-3,7-diazabicyclo[3.3.1]nonan-3-yl)-2,5-difluorophenyl)propyl)-7-amino-3-methylthieno[2,3-b]pyrazine-6-carboxamide

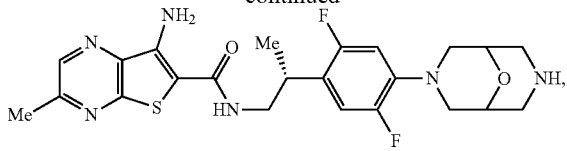

I-22. N-((2S)-2-(4-(9-oxa-3,7-diazabicyclo[3.3.1]nonan-3-yl)-2,5-difluorophenyl)propyl)-7-amino-3-methylthieno[2,3-b]pyrazine-6-carboxamide and

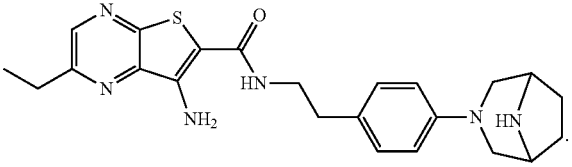

I-23. N-(4-(3,8-diazabicyclo[3.2.1]octan-3-yl)phenethyl)-7-amino-2-ethylthieno[2,3-b]pyrazine-6-carboxamide In another embodiment of the disclosure, the compounds of Formula (I) are enantiomers. In some embodiments the compounds are the (S)-enantiomer. In other embodiments the compounds are the (R)-enantiomer. In yet other embodiments, the compounds of Formula (I) may be (+) or (−) enantiomers.

It should be understood that all isomeric forms are included within the present disclosure, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the disclosure, and pharmaceutically acceptable salts, hydrates, solvates, stereoisomers and prodrugs thereof may exist in their tautomeric form (for example, as an amide or imino ether). All such tautomeric forms are contemplated herein as part of the present disclosure.

The compounds of the disclosure may contain asymmetric or chiral centers, and, therefore, exist in different stereoisomeric forms. It is intended that all stereoisomeric forms of the compounds of the disclosure as well as mixtures thereof, including racemic mixtures, form part of the present disclosure. In addition, the present disclosure embraces all geometric and positional isomers. For example, if a compound of the disclosure incorporates a double bond or a fused ring, both the cis- and trans-forms, as well as mixtures, are embraced within the scope of the disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the disclosure may be atropisomers (e.g., substituted biaryls) and are considered as part of this disclosure. Enantiomers can also be separated by use of a chiral HPLC column.

It is also possible that the compounds of the disclosure may exist in different tautomeric forms, and all such forms are embraced within the scope of the disclosure. Also, for example, all keto-enol and imine-enamine forms of the compounds are included in the disclosure.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the disclosure. Also, for example, all keto-enol and imine-enamine forms of the compounds are included in the disclosure.) Individual stereoisomers of the compounds of the disclosure may, for example, be substantially free of other isomers, or may be admixed, for example, as racemates or with all other, or other selected, stereoisomers. The chiral centers of the present disclosure can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this disclosure. Reference to a compound of the Formula herein is understood to include reference to salts thereof, unless otherwise indicated.

The present disclosure relates to compounds which are modulators of USP28 and/or USP25. In one embodiment, the compounds of the present disclosure are inhibitors of USP28 and/or USP25.

The disclosure is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present disclosure may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art.

The selection processes, as well as the reaction conditions and order of their execution, shall be consistent with the preparation of compounds of Formula (I).

Those skilled in the art will recognize if a stereocenter exists in the compounds of Formula (I). Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereof as appreciated by those skilled in the art. Preferred methods include but are not limited to those methods described below. Compounds of the present invention can be synthesized by following the steps outlined in General Scheme 1 which comprise the assembling of intermediates 2a and 2b. Starting materials are either commercially available or made by known procedures in the reported literature or as illustrated.

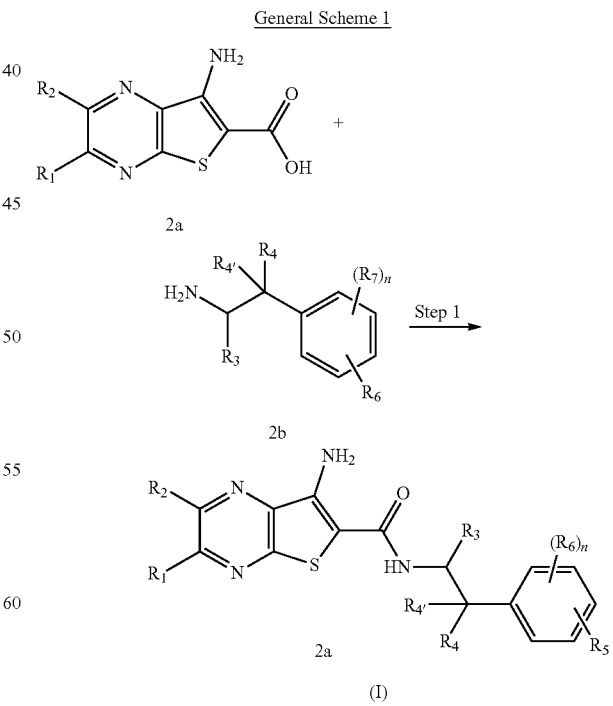

wherein $R_1$-$R_4$, $R_{4'}$, $R_5$, $R_6$ and n are defined as in Formula (I).

The general manner of preparing target compounds of Formula (I) by using intermediates 2a and 2b, is outlined above in General Scheme 1. Coupling of carboxylic acid 2a with amine 2b under standard amide forming conditions using a coupling agent, e.g., 1-Ethyl-3-(3-dimethylamino-propyl)carbodiimide with 1-hydroxybenzotriazole (EDCI/HOBt), (Benzotriazol-1-yloxy)tris(dimethylamino)phosphonium hexafluorophosphate (BOP), O-benzotriazole-N,N,N,N'-tetramethyl-uronium-hexafluoro-phosphate (HBTU) or [bis (dimethylamino)methylene]-1H-1,2,3-triazolo[4,5-b] pyridinium-3-oxide hexafluorophosphate (HATU), and a base, e.g., triethylamine (TEA), N,N-diisopropylethylamine (DIEA), or 4-dimethylaminopyridine (DMAP), in a solvent (e.g. DCM or DMF, etc.) provides the desired product of Formula (I).

Compounds of Formula (I) can exist as enantiomeric or diastereomeric stereoisomers. Enantiomerically pure compounds of Formula (I) can be prepared using enantiomerically pure chiral building blocks. Alternatively, racemic mixtures of the final compounds or a racemic mixture of an advanced intermediate can be subjected to chiral purification as described herein below to deliver the desired enantiomerically pure intermediates or final compounds. In the instances where an advanced intermediate is purified into its individual enantiomers, each individual enantiomer can be carried on separately to deliver the final enantiomerically pure compounds of Formula (I).

It should be understood that in the description and formula shown above, the various groups $R_1$-$R_4$, $R_{4'}$, $R_5$, $R_6$, n, and other variables are as defined above, except where otherwise indicated. Furthermore, for synthetic purposes, the compounds of General Scheme 1 are merely representative with elected radicals to illustrate the general synthetic methodology of the compounds of Formula (I) as defined herein.

Methods of Using the Disclosed Compounds

Another aspect of the disclosure relates to a method of treating, preventing, inhibiting, or eliminating a disease or disorder associated with modulation of USP28. The method comprises administering to a patient in need of a treatment for diseases or disorders associated with modulation of USP28 an effective amount the compositions and compounds of Formula (I). In one embodiment, the disease or disorder is cancer.

In another aspect, the present disclosure is directed to a method of treating, preventing, inhibiting, or eliminating a disease or disorder associated with inhibition of USP28. The method comprises administering to a patient in need of a treatment for diseases or disorders associated with modulation of USP28 an effective amount the compositions and compounds of Formula (I). In one embodiment, the disease or disorder is cancer.

In another aspect, the present disclosure is directed to a method of inhibiting USP28. The method involves administering to a patient in need thereof an effective amount of a compound of Formula (I).

Another aspect of the disclosure relates to a method of treating, preventing, inhibiting, or eliminating a disease or disorder associated with modulation of USP25. The method comprises administering to a patient in need of a treatment for diseases or disorders associated with modulation of USP25 an effective amount the compositions and compounds of Formula (I). In one embodiment, the disease or disorder is cancer. In another embodiment, the disease or disorder is inflammation. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

In another aspect, the present disclosure is directed to a method of treating, preventing, inhibiting, or eliminating a disease or disorder associated with inhibition of USP28. The method comprises administering to a patient in need of a treatment for diseases or disorders associated with modulation of USP25 an effective amount the compositions and compounds of Formula (I). In one embodiment, the disease or disorder is cancer. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

In another aspect, the present disclosure is directed to a method of inhibiting USP25. The method involves administering to a patient in need thereof an effective amount of a compound of Formula (I).

Another aspect of the disclosure relates to a method of treating, preventing, inhibiting, or eliminating a disease or disorder associated with modulation of USP25. The method comprises administering to a patient in need of a treatment for diseases or disorders associated with modulation of USP28 and USP25 an effective amount the compositions and compounds of Formula (I). In one embodiment, the disease or disorder is cancer. In another embodiment, the disease or disorder is inflammation. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

In another aspect, the present disclosure is directed to a method of treating, preventing, inhibiting, or eliminating a disease or disorder associated with inhibition of USP28. The method comprises administering to a patient in need of a treatment for diseases or disorders associated with modulation of USP28 and USP25 an effective amount the compositions and compounds of Formula (I). In one embodiment, the disease or disorder is cancer. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

In another aspect, the present disclosure is directed to a method of inhibiting USP28 and USP25. The method involves administering to a patient in need thereof an effective amount of a compound of Formula (I).

Another aspect of the present disclosure relates to a method of treating, preventing, inhibiting, or eliminating a disease or disorder in a patient associated with the inhibition of USP28, the method comprising administering to a patient in need thereof an effective amount of a compound of Formula (I). In one embodiment, the disease or disorder is cancer.

Another aspect of the present disclosure relates to a method of treating, preventing, inhibiting, or eliminating a disease or disorder in a patient associated with the inhibition of USP25, the method comprising administering to a patient in need thereof an effective amount of a compound of Formula (I). In one embodiment, the disease or disorder is cancer. In another embodiment, the disease or disorder is inflammation. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

Another aspect of the present disclosure relates to a method of treating, preventing, inhibiting, or eliminating a disease or disorder in a patient associated with the inhibition of USP28 and USP25, the method comprising administering to a patient in need thereof an effective amount of a compound of Formula (I). In one embodiment, the disease or disorder is cancer. In another embodiment, the disease or disorder is inflammation. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

In another aspect, the present invention relates to a method of treating, preventing, inhibiting, or eliminating cancer. The method comprises administering to a patient in need of a treatment for cancer an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating inflammation. The method comprises administering to a patient in need of a treatment for cancer an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating an autoimmune disease. The method comprises administering to a patient in need of a treatment for cancer an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating an infectious disease. The method comprises administering to a patient in need of a treatment for cancer an effective amount of a compound of Formula (I), or a pharmaceutically acceptable salt, hydrate, solvate, prodrug, stereoisomer, or tautomer thereof. In one embodiment, the infectious disease is a viral infection. In another embodiment, the infectious disease is a bacterial infection.

In another aspect, the present invention relates to a method of treating, preventing, inhibiting, or eliminating a viral infection. The method comprises administering to a patient in need of a treatment for cancer an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating a bacterial infection. The method comprises administering to a patient in need of a treatment for cancer an effective amount of a compound of Formula (I), or a pharmaceutically acceptable salt, hydrate, solvate, prodrug, stereoisomer, or tautomer thereof.

Another aspect of the present invention relates to a compound of Formula (I), or a pharmaceutically acceptable salt, hydrate, solvate, prodrug, stereoisomer, or tautomer thereof, for use in a method of treating, preventing, inhibiting, or eliminating a disease or disorder associated with inhibiting USP28. In one embodiment, the disease or disorder is cancer.

In another aspect, the present invention relates to a compound of Formula (I), or a pharmaceutically acceptable salt, hydrate, solvate, prodrug, stereoisomer, or tautomer thereof, for use in a method of treating, preventing, inhibiting, or eliminating a disease or disorder associated with inhibiting USP25. In one embodiment, the disease or disorder is cancer. In another embodiment, the disease or disorder is inflammation. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

Another aspect of the present invention relates to a compound of Formula (I), or a pharmaceutically acceptable salt, hydrate, solvate, prodrug, stereoisomer, or tautomer thereof, for use in a method of treating, preventing, inhibiting, or eliminating a disease or disorder associated with inhibiting USP28 and USP25. In one embodiment, the disease or disorder is cancer. In another embodiment, the disease or disorder is inflammation. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

In another aspect, the present invention relates to a compound of Formula (I), or a pharmaceutically acceptable salt, hydrate, solvate, prodrug, stereoisomer, or tautomer thereof, for use in a method for treating, preventing, inhibiting, or eliminating cancer.

In another aspect, the present invention relates to a compound of Formula (I), or a pharmaceutically acceptable salt, hydrate, solvate, prodrug, stereoisomer, or tautomer thereof, for use in a method for treating, preventing, inhibiting, or eliminating inflammation.

In another aspect, the present invention relates to a compound of Formula (I), or a pharmaceutically acceptable salt, hydrate, solvate, prodrug, stereoisomer, or tautomer thereof, for use in a method for treating, preventing, inhibiting, or eliminating an autoimmune disease.

In another aspect, the present invention relates to a compound of Formula (I), or a pharmaceutically acceptable salt, hydrate, solvate, prodrug, stereoisomer, or tautomer thereof, for use in a method for treating, preventing, inhibiting, or eliminating an infectious disease.

In another aspect, the present invention relates to a compound of Formula (I), or a pharmaceutically acceptable salt, hydrate, solvate, prodrug, stereoisomer, or tautomer thereof, for use in a method for treating, preventing, inhibiting, or eliminating a viral infection.

In another aspect, the present invention relates to a compound of Formula (I), or a pharmaceutically acceptable salt, hydrate, solvate, prodrug, stereoisomer, or tautomer thereof, for use in a method for treating, preventing, inhibiting, or eliminating a bacterial infection.

Another aspect of the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a disease or disorder associated with inhibiting USP28. In one embodiment, the disease or disorder is cancer.

Another aspect of the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a disease or disorder associated with inhibiting USP25. In one embodiment, the disease or disorder is cancer. In another embodiment, the disease or disorder is inflammation. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

Another aspect of the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a disease or disorder associated with inhibiting USP28 and USP25. In one embodiment, the disease or disorder is cancer. In another embodiment, the disease or disorder is inflammation. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating cancer.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating inflammation.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating autoimmune disorder.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating an infection disease. In one embodiment, the infectious disease is a viral infection. In another embodiment, the infectious disease is a bacterial infection.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a viral infection.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a bacterial infection.

In other embodiments, the present invention relates to the use of an inhibitor of USP28 for the preparation of a medicament used in the treatment, prevention, inhibition or elimination of a disease or disorder associated with cancer.

In other embodiments, the present invention relates to the use of an inhibitor of USP28 for the preparation of a medicament used in the treatment, prevention, inhibition or elimination of a disease or disorder associated with inflammation.

In other embodiments, the present invention relates to the use of an inhibitor of USP28 for the preparation of a medicament used in the treatment, prevention, inhibition or elimination of a disease or disorder associated with an autoimmune disease.

In other embodiments, the present invention relates to the use of an inhibitor of USP28 for the preparation of a medicament used in the treatment, prevention, inhibition or elimination of a disease or disorder associated with an infectious disease. In one embodiment, the infectious disease is a viral infection. In another embodiment, the infectious disease is a bacterial infection.

In other embodiments, the present invention relates to the use of an inhibitor of USP28 for the preparation of a medicament used in the treatment, prevention, inhibition or elimination of a disease or disorder associated with a viral infection.

In other embodiments, the present invention relates to the use of an inhibitor of USP28 for the preparation of a medicament used in the treatment, prevention, inhibition or elimination of a disease or disorder associated with a bacterial infection.

The present disclosure also relates to the use of an inhibitor of USP28 for the preparation of a medicament used in the treatment, prevention, inhibition, or elimination of a disease or condition mediated by USP28, wherein the medicament comprises a compound of Formula (I).

The present disclosure also relates to the use of an inhibitor of USP25 for the preparation of a medicament used in the treatment, prevention, inhibition, or elimination of a disease or condition mediated by USP25, wherein the medicament comprises a compound of Formula (I).

The present disclosure also relates to the use of an inhibitor of USP28 and USP25 for the preparation of a medicament used in the treatment, prevention, inhibition, or elimination of a disease or condition mediated by USP28 and USP25, wherein the medicament comprises a compound of Formula (I).

In another aspect, the present disclosure relates to a method for the manufacture of a medicament for treating, preventing, inhibiting, or eliminating a disease or condition mediated by USP28, wherein the medicament comprises a compound of Formula (I).

Another aspect of the present disclosure relates to a method for the manufacture of a medicament for treating, preventing, inhibiting, or eliminating a disease or condition mediated by USP25, wherein the medicament comprises a compound of Formula (I).

In another aspect, the present disclosure relates to a method for the manufacture of a medicament for treating, preventing, inhibiting, or eliminating a disease or condition mediated by USP28 and USP25, wherein the medicament comprises a compound of Formula (I).

In some embodiments of the methods described herein, the cancer is selected from bladder cancer, breast cancer (e.g., ductal carcinoma), cervical cancer (e.g., squamous cell carcinoma), colorectal cancer (e.g., adenocarcinoma), colon cancer, esophageal cancer (e.g., squamous cell carcinoma), gastric cancer (e.g., adenocarcinoma, choriocarcinoma, squamous cell carcinoma), head and neck cancer, hematologic cancer (e.g., acute lymphocytic anemia, acute myeloid leukemia, acute lymphoblastic B cell leukemia, anaplastic large cell lymphoma, B-cell lymphoma, Burkitt's lymphoma, chronic lymphocytic leukemia, chronic eosinophillic leukemia/hypereosinophillic syndrome, chronic myeloid leukemia, Hodgkin's lymphoma, mantle cell lymphoma, multiple myeloma, T-cell acute lymphoblastic leukemia), lung cancer (e.g., bronchioloalveolar adenocarcinoma, mesothelioma, mucoepidermoid carcinoma, small-cell lung cancer, non-small cell lung cancer, adenocarcinoma, squamous cell carcinoma), liver cancer (e.g., hepatocellular carcinoma), lymphoma, neurological cancer (e.g., glioblastoma, neuroblastoma, neuroglioma), ovarian cancer (e.g., adenocarcinoma), pancreatic cancer (e.g., ductal carcinoma), prostate cancer (e.g., adenocarcinoma), renal cancer (e.g., renal cell carcinoma, clear cell renal cancer carcinoma), sarcoma (e.g., chondrosarcoma, Ewings sarcoma, fibrosarcoma, multipotential sarcoma, osteosarcoma, rhabdomyosarcoma, synovial sarcoma), skin cancer (e.g., melanoma, epidermoid carcinoma, squamous cell carcinoma), thyroid cancer (e.g., medullary carcinoma), and uterine cancer. In some embodiments, the cancer is a cancer that is sensitive to USP28 inhibition. In other embodiments, the cancer is a cancer that is sensitive to USP25 inhibition. In other embodiments, the cancer is a cancer that is sensitive to USP28 and USP25 inhibition.

In any of the embodiments of the disclosure, the cancer can be any cancer in any organ, for example, a cancer is selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof.

In other embodiments, the cancer is selected from acute myeloid leukemia, gastric, pancreatic, colorectal, glioblastoma, neuroblastoma, small-cell lung, non-small cell lung, and squamous cell carcinoma.

In another embodiment, the present disclosure relates to a compound of Formula (I) or a pharmaceutical composition comprising a compound of the present disclosure and a pharmaceutically acceptable carrier used for the treatment of cancers including, but not limited to, bladder cancer, breast cancer (e.g., ductal carcinoma), cervical cancer (e.g., squamous cell carcinoma), colorectal cancer (e.g., adenocarcinoma), esophageal cancer (e.g., squamous cell carcinoma), gastric cancer (e.g., adenocarcinoma, choriocarcinoma, squamous cell carcinoma), head and neck cancer, hematologic cancer (e.g., acute lymphocytic anemia, acute myeloid leukemia, acute lymphoblastic B cell leukemia, anaplastic large cell lymphoma, B-cell lymphoma, Burkitt's lymphoma, chronic lymphocytic leukemia, chronic eosinophillic leukemia/hypereosinophillic syndrome, chronic myeloid leukemia, Hodgkin's lymphoma, mantle cell lymphoma, multiple myeloma, T-cell acute lymphoblastic leukemia), lung cancer (e.g., bronchioloalveolar adenocarcinoma, mesothelioma, mucoepidermoid carcinoma, small-cell lung cancer, non-small cell lung cancer, adenocarcinoma, squamous cell carcinoma), liver cancer (e.g., hepatocellular carcinoma), lymphoma, neurological cancer (e.g., glioblastoma, neuroblastoma, neuroglioma), ovarian cancer (e.g., adenocarcinoma), pancreatic cancer (e.g., ductal carcinoma), prostate cancer (e.g., adenocarcinoma), renal cancer (e.g., renal cell carcinoma, clear cell renal cancer carcinoma), sarcoma (e.g., chondrosarcoma, Ewings sarcoma, fibrosarcoma, multipotential sarcoma, osteosarcoma, rhabdomyosarcoma, synovial sarcoma), skin cancer (e.g., melanoma, epidermoid carcinoma, squamous cell carcinoma), thyroid cancer (e.g., medullary carcinoma), and uterine cancer. In other embodiments, the cancer is selected from acute myeloid leukemia, gastric cancer, pancreatic cancer, colorectal cancer, glioblastoma, neuroblastoma, small-cell lung cancer, non-small cell lung cancer, and squamous cell carcinoma.

In some embodiments, the patient is selected for treatment based on gene amplification and/or elevated tumor expression of USP28, MYC, LSD1, NICD1, and/or reduced expression of FBXW7 relative to tissue-matched expression.

In some embodiments, the patient is selected for treatment based on gene amplification and/or elevated tumor expression of USP28, USP25, MYC, LSD1, NICD1, and/or reduced expression of FBXW7 relative to tissue-matched expression.

In some embodiments, administration of a compound of Formula (I) or a pharmaceutical composition comprising a compound of the present disclosure and a pharmaceutically acceptable carrier induces a change in the cell cycle, cell viability, cell apoptosis, or differentiation.

For example, the change in the cell cycle or cell viability or differentiation may be indicated by decreased tumor levels of MYC, LSD1, NICD1, PIM1, CDK1, POLA2, HEY1, and/or CCND1, and/or increased levels of CD86, p21, LGALS4, and/or DLL1.

In another embodiment, the present disclosure relates to a compound of Formula (I) or a pharmaceutical composition comprising a compound of the present disclosure and a pharmaceutically acceptable carrier used for the treatment of autoimmune diseases including, but not limited to, multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, cutaneous lupus erythematosus including chilblain lupus erythematosus, lupus nephritis, discoid lupus, subacute cutaneous lupus erythematosus, dermatomyositis, polymyositis, idiopathic myxedema, Hashimoto's disease, Guillain-Barre' syndrome, Grave's disease, myasthenia gravis, Sjogren's syndrome, nodular panarteritis, autoimmune enteropathy, uveitis, autoimmune oophoritis, chronic immune thrombocytopenic purpura, colitis, diabetes, psoriasis, pemphigus vulgaris, proliferative glomerulonephritis, Wiskott-Aldrich syndrome, autoimmune lymphoproliferative syndrome, chronic arthritis, inflammatory chronic rhinosinusitis, colitis, celiac disease, inflammatory bowel disease, Barrett's esophagus, inflammatory gastritis, autoimmune nephritis, autoimmune vasculitis, autoimmune hepatitis, autoimmune carditis, autoimmune encephalitis, and autoimmune mediated hematological disease.

In any of the embodiments of the disclosure, the autoimmune disease can be, for example, an autoimmune disease selected from multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, cutaneous lupus erythematosus including chilblain lupus erythematosus, lupus nephritis, discoid lupus, subacute cutaneous lupus erythematosus, dermatomyositis, polymyositis, idiopathic myxedema, Hashimoto's disease, Guillain-Barre' syndrome, Grave's disease, myasthenia gravis, Sjogren's syndrome, nodular panarteritis, autoimmune enteropathy, uveitis, autoimmune oophoritis, chronic immune thrombocytopenic purpura, colitis, diabetes, psoriasis, pemphigus vulgaris, proliferative glomerulonephritis, Wiskott-Aldrich syndrome, autoimmune lymphoproliferative syndrome, chronic arthritis, inflammatory chronic rhinosinusitis, colitis, celiac disease, inflammatory bowel disease, Barrett's esophagus, inflammatory gastritis, autoimmune nephritis, autoimmune vasculitis, autoimmune hepatitis, autoimmune carditis, autoimmune encephalitis, and autoimmune mediated hematological disease.

Another aspect of the disclosure is directed to pharmaceutical compositions comprising a compound of Formula (I) and a pharmaceutically acceptable carrier. The pharmaceutical acceptable carrier may further include an excipient, diluent, or surfactant.

In one embodiment, are provided methods of treating a disease or disorder associated with modulation of USP28 including cancer comprising administering to a patient suffering from at least one of said diseases or disorder a compound of Formula (I).

In another embodiment, are provided methods of treating a disease or disorder associated with modulation of USP25 including cancer, inflammation, an autoimmune disease, a viral infection and a bacterial infection, comprising administering to a patient suffering from at least one of said diseases or disorder a compound of Formula (I).

In another embodiment, are provided methods of treating a disease or disorder associated with modulation of USP28 and USP25 including cancer, inflammation, an autoimmune disease, a viral infection and a bacterial infection, comprising administering to a patient suffering from at least one of said diseases or disorder a compound of Formula (I).

One therapeutic use of the compounds or compositions of the present disclosure which inhibit USP28 is to provide treatment to patients or subjects suffering from cancer.

Another therapeutic use of the compounds or compositions of the present disclosure which inhibit USP25 is to provide treatment to patients or subjects suffering from cancer.

Another therapeutic use of the compounds or compositions of the present disclosure which inhibit USP28 and USP25 is to provide treatment to patients or subjects suffering from cancer.

Another therapeutic use of the compounds or compositions of the present disclosure which inhibit USP25 is to provide treatment to patients or subjects suffering from inflammation.

Another therapeutic use of the compounds or compositions of the present disclosure which inhibit USP28 and USP25 is to provide treatment to patients or subjects suffering from inflammation.

Another therapeutic use of the compounds or compositions of the present disclosure which inhibit USP25 is to provide treatment to patients or subjects suffering from an autoimmune disease.

Another therapeutic use of the compounds or compositions of the present disclosure which inhibit USP28 and USP25 is to provide treatment to patients or subjects suffering from an autoimmune disease.

Another therapeutic use of the compounds or compositions of the present disclosure which inhibit USP25 is to provide treatment to patients or subjects suffering from an infectious disease.

Another therapeutic use of the compounds or compositions of the present disclosure which inhibit USP28 and USP25 is to provide treatment to patients or subjects suffering from an infectious disease.

Another therapeutic use of the compounds or compositions of the present disclosure which inhibit USP25 is to provide treatment to patients or subjects suffering from a viral infection.

Another therapeutic use of the compounds or compositions of the present disclosure which inhibit USP28 and USP25 is to provide treatment to patients or subjects suffering from a viral infection.

Another therapeutic use of the compounds or compositions of the present disclosure which inhibit USP25 is to provide treatment to patients or subjects suffering from a bacterial infection.

Another therapeutic use of the compounds or compositions of the present disclosure which inhibit USP28 and USP25 is to provide treatment to patients or subjects suffering from a bacterial infection.

The disclosed compounds of the disclosure can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the disclosure is directed to pharmaceutical compositions comprising a compound of Formula (I) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 200% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. Proton nuclear magnetic resonance (NMR) spectra were obtained on either Bruker or Varian spectrometers at 300 or 400 MHz. Spectra are given in ppm ($\delta$) and coupling constants, J, are reported in Hertz. Tetramethylsilane (TMS) was used as an internal standard. Mass spectra were collected using a Waters ZQ Single Quad Mass Spectrometer (ion trap electrospray ionization (ESI)). Purity and low resolution mass spectral data were measured using Waters Acquity i-class ultra-performance liquid chromatography (UPLC) system with Acquity Photo Diode Array Detector, Acquity Evaporative Light Scattering Detector (ELSD) and Waters ZQ Mass Spectrometer. Data was acquired using Waters MassLynx 4.1 software and purity characterized by UV wavelength 220 nm, evaporative light scattering detection (ELSD) and electrospray positive ion (ESI). (Column: Acquity UPLC BEH C18 1.7 µm 2.1×50 mm; Flow rate 0.6 mL/min; Solvent A (95/5/0.1%: 10 mM Ammonium Formate/Acetonitrile/Formic Acid), Solvent B (95/5/0.09%: Acetonitrile/Water/Formic Acid); gradient: 5-100% B from 0 to 2 mins, hold 100% B to 2.2 mins and 5% B at 2.21 mins. Preparatory HPLC purifications were conducted on a Waters SunFire C18 OBD Prep Column, 100 Å, 5 µm, 19 mm×50 mm, Waters XBridge BEH C18 OBD Prep Column, 130 Å, 5 µm, 19 mm×50 mm with UV detection (Waters 2489 UV/998 PDA), Waters SunFire C18 OBD Prep Column, 100 Å, 5 µm, 19 mm×150 mm, Waters XBridge BEH Shield RP18 OBD Prep Column, 130 Å, 5 µm, 19 mm×150 mm, or Waters XSelect CSH C18 OBD Prep Column, 130 Å, 5 µm, 19 mm×150 mm at 254 nm or 220 nm using a standard solvent gradient program (e.g., as designated below). The absolute configuration of the separated enantiomers of the compounds in the examples described herein were not determined. As such, the configuration of the resolved materials were arbitrarily assigned as R or S in each case.

Abbreviations used in the following examples and elsewhere herein are:
atm atmosphere
br broad
BINAP (2,2'-bis(diphenylphosphino)-1,1'-binaphthyl)
BOP ((1H-benzo[d][1,2,3]triazol-1-yl)oxy)tris(dimethylamino)phosphonium hexafluorophosphate(V)
Cbz carboxybenzyl
d doublet
DCM dichloromethane
DEA diethylamine DIEA N,N-diisopropylethylamine
DMA N,N-dimethylacetamide
DMAP 4-dimethylaminopyridine
DMF N,N-dimethylformamide
DMSO dimethyl sulfoxide
dppf 1,1'-bis(diphenylphosphino)ferrocene
EA ethyl acetate
EDCI N-(3-dimethylaminopropyl)-N'-ethylcarbodiimide hydrochloride
ESI electrospray ionization
FCC flash column chromatography
h hour(s)
HATU [bis(dimethylamino)methylene]-1H-1,2,3-triazolo[4,5-b]pyridinium 3-oxide hexafluorophosphate
HBTU 3-[bis(dimethylamino)methyliumyl]-3H-benzotriazol-1-oxide hexafluorophosphate
HMPA hexamethylphosphoramide
HOBt benzotriazol-1-ol
HPLC high-performance liquid chromatography
LCMS liquid chromatography-mass spectrometry
m multiplet
MHz megahertz
min minutes
μW microwave
NCS N-chlorosuccinimide
NMR nuclear magnetic resonance
PE petroleum ether
ppm parts per million
q quartet
RT room temperature
RuPhos 2-dicyclohexylphosphino-2',6'-diisopropoxybiphenyl
s singlet
SPhos 2-Dicyclohexylphosphino-2',6'-dimethoxybiphenyl
t triplet
tBuBrettPhos di-tert-butyl(2',4',6'-triisopropyl-3,6-dimethoxy-[1,1'-biphenyl]-2-yl)phosphine
TEA triethylamine
TFA trifluoroacetic acid
THF tetrahydrofuran
TLC thin layer chromatography
TosMIC 1-(isocyanomethylsulfonyl)-4-methylbenzene
XantPhos 4,5-Bis(diphenylphosphino)-9,9-dimethylxanthene
XPhos 2-Dicyclohexylphosphino-2',4',6'-triisopropylbiphenyl Example 1: Intermediate 1. 7-Amino-3-methylthieno[2,3-b]pyrazine-6-carboxylic acid

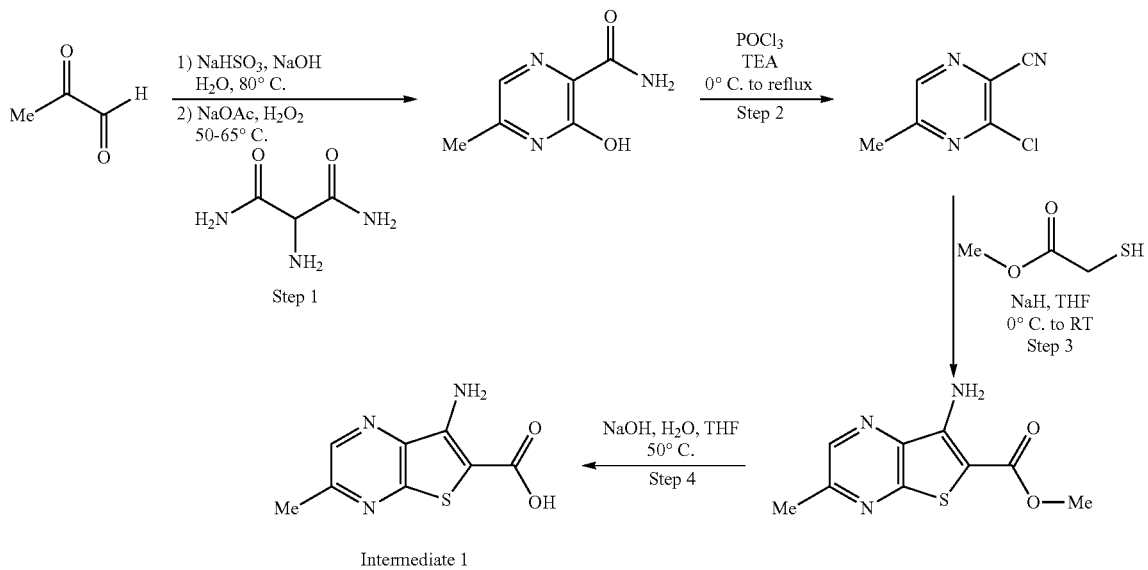

Intermediate 1

Step 1. 3-Hydroxy-5-methylpyrazine-2-carboxamide

A solution of 2-oxopropanal (277 mL, 40% wt, 1.54 mol), NaHSO$_3$ (201 g, 1.93 mol) and sodium hydroxide (6.4 g, 0.16 mol) in water (500 mL) was stirred for 1 h at 80° C. 2-Aminopropanediamide (150 g, 1.28 mol) was then added and the mixture was stirred for another 2 h at 80° C. Sodium acetate (263 g, 3.21 mol) was added, followed by H$_2$O$_2$ (30%; 210 mL) was added dropwise at 50-65° C. The reaction mixture was cooled to RT and stirred for 1 h. The resulting precipitate was collected by filtration and recrystallized from 75% EtOH to afford 3-hydroxy-5-methylpyrazine-2-carboxamide (119 g, 61% yield) as an orange solid. $^1$H-NMR (400 MHz, DMSO-d$_6$): δ 8.75 (br s, 1H), 8.06 (br s, 1H), 7.83 (br s, 1H), 2.37 (s, 3H).

Step 2. 3-Chloro-5-methylpyrazine-2-carbonitrile

To a mixture of 3-hydroxy-5-methylpyrazine-2-carboxamide (155 g, 1.01 mol) and TEA (205 g, 2.03 mol) was added dropwise POCl$_3$ (500 mL) at 0° C. The reaction mixture was refluxed for 4 h and then cooled to room temperature. The mixture was concentrated under vacuum and then ethyl acetate (500 mL) and saturated aqueous NaHCO$_3$ (1000 mL) were added. The organic phase was separated and the aqueous phase was extracted with ethyl acetate (2×500 mL). The combined organic phases were dried over anhydrous sodium sulfate, filtered, and concentrated. The residue was purified by silica gel column chromatography eluting with petroleum ether/EtOAc (95:5) to afford 3-chloro-5-methylpyrazine-2-carbonitrile (55 g, 35% yield) as a light yellow solid. $^1$H NMR (400 MHz, CDCl$_3$): δ 8.51 (s, 1H), 2.69 (s, 3H).

Step 3. Methyl 7-amino-3-methylthieno[2,3-b]pyrazine-6-carboxylate

To a solution of 3-chloro-5-methylpyrazine-2-carbonitrile (19 g, 0.12 mol) and methyl 2-mercaptoacetate (14 g, 0.13 mol) in THF (200 mL) was added NaH (60% dispersion in mineral oil; 7.5 g, 0.19 mol) in small portions at 0° C. The reaction mixture was stirred overnight at RT and then water (200 mL) was carefully added to quench the reaction. The resulting mixture was extracted with ethyl acetate (2×300 mL). The combined organic phases were dried over anhydrous sodium sulfate, filtered, and concentrated. The residue was purified via silica gel column chromatography eluting with petroleum ether/EtOAc (90:10 to 70:30) to afford methyl 7-amino-3-methylthieno[2,3-b]pyrazine-6-carboxylate (20 g, 72% yield) as a light yellow solid. $^1$H NMR (400 MHz, DMSO-d$_6$): δ 8.68 (s, 1H), 7.10 (br s, 2H), 3.83 (s, 3H), 2.65 (s, 3H).

Step 4. 7-Amino-3-methylthieno[2,3-b]pyrazine-6-carboxylic acid

To a solution of methyl 7-amino-3-methylthieno[2,3-b]pyrazine-6-carboxylate (50 g, 0.22 mol) in THF (200 mL) and water (200 mL) was added NaOH (13 g, 0.34 mol) at RT. The reaction mixture was stirred for 4 h at 50° C., cooled to RT, and then washed with ethyl acetate (2×200 mL). The aqueous layer was separated and the pH was adjusted to 4-5 with aqueous HCl (2M). The resulting precipitate was isolated by filtration and dried to afford 7-amino-3-methylthieno[2,3-b]pyrazine-6-carboxylic acid (45 g, 96% yield) as a yellow solid. $^1$H NMR (400 MHz, DMSO-d$_6$): δ 12.97 (br s, 1H), 8.66 (s, 1H), 6.96 (br s, 2H), 2.65 (s, 3H).

Example 2: Intermediate 2. 7-Amino-3-ethylthieno[2,3-b]pyrazine-6-carboxylic acid

Step 1. 3-Chloro-2-cyanopyrazine 1-oxide

Into a 250-mL 3-necked round-bottom flask was added 3-chloropyrazine-2-carbonitrile (10.0 g, 71.7 mmol) and concentrated sulfuric acid (70 mL) followed by the portionwise addition of K$_2$S$_2$O$_8$ (23.3 g, 86.3 mmol) at 0° C. The resulting solution was stirred for 24 h at 25° C. and then extracted with ethyl acetate (3×500 mL). The combined organic layers were dried over anhydrous sodium sulfate, filtered, and concentrated in vacuo. The crude product was triturated with petroleum ether (100 mL) and the resulting solids were collected by filtration and dried under vacuum to afford 3-chloro-2-cyanopyrazine 1-oxide as a yellow solid which was carried on without further purification (3.4 g, 31%). LCMS (ESI, m/z): 156 [M+H]$^+$.

Step 2. 7-Amino-6-(methoxycarbonyl)thieno[2,3-b]pyrazine 1-oxide

Into a 250-mL round-bottom flask, purged and maintained with an inert atmosphere of nitrogen, was added 3-chloro-2-cyanopyrazine 1-oxide (4.40 g, 28.3 mmol), methyl 2-mercaptoacetate (3.01 g, 28.4 mmol), and DMF (40 mL) followed by the portionwise addition of sodium methoxide (6.13 g, 114 mmol) at 0° C. The resulting mixture was stirred for 13 h at 25° C. and then quenched by the addition of water (150 mL). The resulting solution was extracted with ethyl acetate (3×200 mL). The combined organic layers were dried over anhydrous sodium sulfate, filtered, and concentrated in vacuo. The crude product was purified via silica gel chromatography and eluted with ethyl acetate/petroleum ether (1:100 to 10:1) to afford 7-amino-6-(methoxycarbonyl)thieno[2,3-b]pyrazine 1-oxide as a yellow solid (2.3 g, 36%). LCMS (ESI, m/z): 226 [M+H]$^+$.

Step 3. Methyl 7-amino-2-chlorothieno[2,3-b]pyrazine-6-carboxylate

Into a 12-mL microwave tube was added 7-amino-6-(methoxycarbonyl)thieno[2,3-b]pyrazine 1-oxide (0.600 g, 2.66 mmol) and POCl$_3$ (6 mL). The resulting solution was heated under microwave irradiation for 1 h at 90° C. The reaction mixture was cooled to RT and then concentrated in vacuo. The crude product was taken up into water (50 mL)

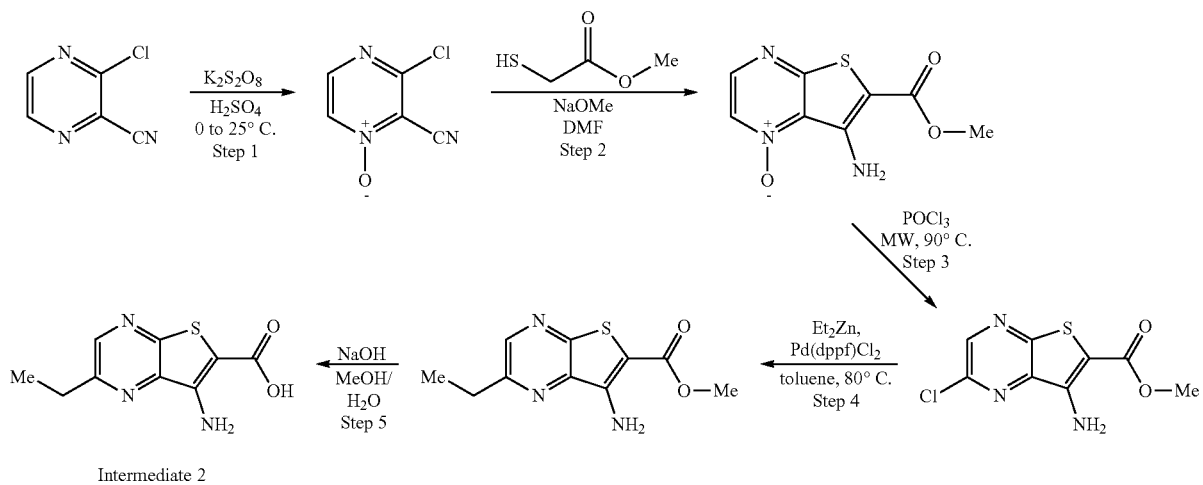

Intermediate 2 and the resulting aqueous mixture was extracted with ethyl acetate (3×100 mL). The organic layers were combined, dried over anhydrous sodium sulfate, filtered, and concentrated in vacuo. The crude product was purified via silica gel chromatography and eluted with ethyl acetate/petroleum ether (1:100 to 10:1) to afford methyl 7-amino-2-chlorothieno[2,3-b]pyrazine-6-carboxylate as a yellow solid (200 mg, 31%). LCMS (ESI, m/z): 244 [M+H]⁺.

Step 4. Methyl 7-amino-2-ethylthieno[2,3-b]pyrazine-6-carboxylate

Into a 25-mL round-bottom flask, purged and maintained with an inert atmosphere of nitrogen, was added methyl 7-amino-2-chlorothieno[2,3-b]pyrazine-6-carboxylate (0.20 g, 0.82 mmol), Pd(dppf)Cl$_2$CH$_2$Cl$_2$ (0.13 g, 0.16 mmol), and toluene (7 mL). A solution of diethylzinc in toluene (1.5 M, 4.11 mL, 6.16 mmol) was then added and the resulting solution was stirred for 18 h at 80° C. The reaction was cooled to RT and concentrated in vacuo. The crude product was purified via silica gel chromatography and eluted with ethyl acetate/petroleum ether (1:3) to afford methyl 7-amino-2-ethylthieno[2,3-b]pyrazine-6-carboxylate as a yellow solid (190 mg, 98%). LCMS (ESI, m/z): 238 [M+H]⁺.

Step 5. 7-Amino-2-ethylthieno[2,3-b]pyrazine-6-carboxylic acid

Into a 25-mL round-bottom flask was added methyl 7-amino-2-ethylthieno[2,3-b]pyrazine-6-carboxylate (0.190 g, 0.80 mmol), methanol (3 mL), water (1 mL), and sodium hydroxide (0.064 g, 1.60 mmol). The resulting solution was stirred for 18 h at 25° C. and then concentrated in vacuo to remove most of the organic solvent. The pH of the solution was adjusted to approximately 7 with aqueous HCl (1M). The resulting solids were collected by filtration and dried in vacuo to afford 7-amino-2-ethylthieno[2,3-b]pyrazine-6-carboxylic acid as a yellow solid (125 mg, 70%). LCMS (ESI, m/z): 224 [M+H]⁺.

Example 3: Intermediate 3. Benzyl 4-(4-(2-aminoethyl)phenyl)piperazine-1-carboxylate (hydrochloride salt)

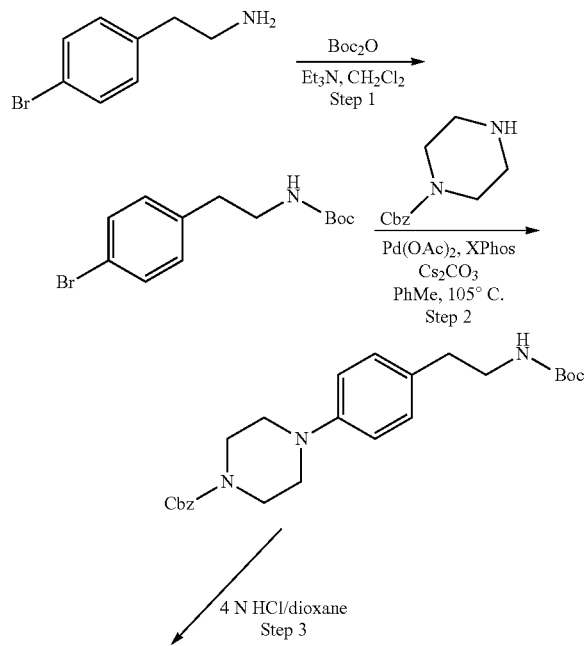

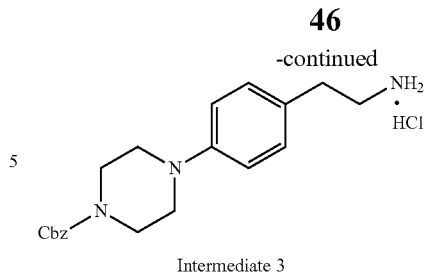

Intermediate 3

Step 1. tert-Butyl (4-bromophenethyl)carbamate

To a solution of 2-(4-bromophenyl)ethan-1-amine (5.00 g, 25.0 mmol) in anhydrous dichloromethane (50 mL) was added Boc$_2$O (6.57 g, 30.1 mmol) followed by Et$_3$N (10.4 mL, 74.9 mmol). The resulting solution was stirred overnight at 25° C. and then concentrated in vacuo. The crude product was purified by FCC eluting with ethyl acetate/petroleum ether (PE/EA=3:1) to afford tert-butyl (4-bromophenethyl)carbamate as a white solid (7.1 g, 95%). LCMS (ESI, m/z): 300 [M+H]⁺.

Step 2. Benzyl 4-(4-(2-((tert-butoxycarbonyl)amino)ethyl)phenyl)piperazine-1-carboxylate Into a 100-mL round-bottom flask, purged and maintained with an inert atmosphere of nitrogen, was added tert-butyl (4-bromophenethyl)carbamate (4.00 g, 13.3 mmol) and anhydrous toluene (50 mL). To the resulting solution was added benzyl piperazine-1-carboxylate (3.53 g, 16.0 mmol), Pd(OAc)$_2$ (300 mg, 1.34 mmol), XPhos (1.28 g, 2.69 mmol), and Cs$_2$CO$_3$ (13.1 g, 40.0 mmol). The reaction mixture was stirred overnight at 105° C. in an oil bath and then cooled to RT and quenched by the addition of H$_2$O (200 mL). The resulting mixture was extracted with ethyl acetate (2×50 mL). The combined organic layers were washed with brine (1×200 mL), dried over anhydrous sodium sulfate, filtered, and concentrated in vacuo. The crude product was purified by FCC eluting with ethyl acetate/petroleum ether (PE/EA=3:1) to afford benzyl 4-(4-(2-((tert-butoxycarbonyl)amino)ethyl)phenyl)piperazine-1-carboxylate as a yellow solid (5 g, 85%). LCMS (ESI, m/z): 440 [M+H]⁺.

Step 3. Benzyl 4-(4-(2-aminoethyl)phenyl)piperazine-1-carboxylate (hydrochloride salt)

Into a 100-mL round-bottom flask was added benzyl 4-(4-(2-((tert-butoxycarbonyl)amino)ethyl)phenyl)piperazine-1-carboxylate (3.0 g, 6.83 mmol), followed by 4 N hydrogen chloride/dioxane (10 mL). The resulting solution was stirred for 1 h at RT then was concentrated in vacuo to afford benzyl 4-(4-(2-aminoethyl)phenyl)piperazine-1-carboxylate (hydrochloride salt) as a yellow solid (2.0 g, 86%). LCMS (ESI, m/z): 340 [M+H]⁺.

Example 4: Intermediate 4. tert-Butyl 4-[4-(2-aminoethyl)-2-chlorophenyl]piperazine-1-carboxylate

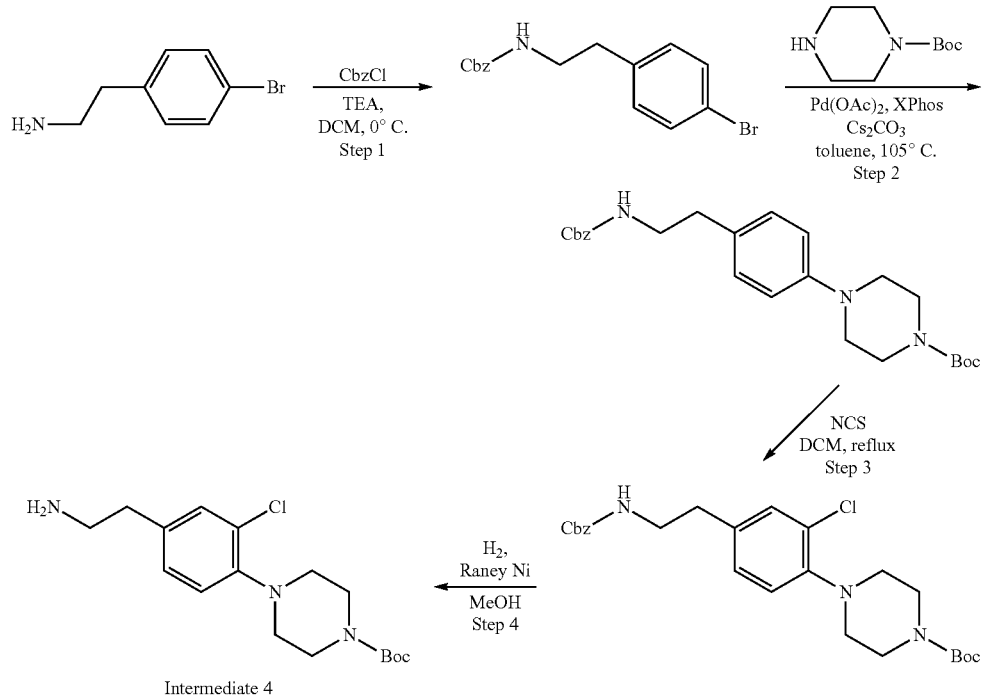

Intermediate 4

Step 1. Benzyl N-[2-(4-bromophenyl)ethyl]carbamate

Into a 1-L 3-necked round-bottom flask was added 2-(4-bromophenyl)ethan-1-amine (80.0 g, 400 mmol), anhydrous DCM (800 mL), and TEA (48.7 g, 67.1 mL, 481 mmol). The resulting mixture was cooled to 0° C. and then a solution of benzyl chloroformate (68.3 g, 56.9 mL, 400 mmol) in anhydrous DCM (20 mL) was added dropwise. The resulting solution was stirred for 2 h at 0° C. and then concentrated in vacuo. The crude product was purified via silica gel chromatography and eluted with ethyl acetate/petroleum ether (1:3) to afford benzyl N-[2-(4-bromophenyl)ethyl]carbamate as a white solid (100 g, 75%). LCMS (ESI, m/z): 334 $[M+H]^+$.

Step 2. tert-Butyl 4-[4-(2-[[(benzyloxy)carbonyl]amino]ethyl)phenyl]piperazine-1-carboxylate Into a 1-L round-bottom flask, purged and maintained with an inert atmosphere of nitrogen, was added benzyl N-[2-(4-bromophenyl)ethyl]carbamate (50.0 g, 150 mmol), toluene (500 mL), tert-butyl piperazine-1-carboxylate (34.0 g, 183 mmol), Pd(OAc)$_2$ (3.40 g, 15.1 mmol), XPhos (14.3 g, 30.3 mmol), and Cs$_2$CO$_3$ (98.0 g, 301 mmol). The resulting mixture was stirred overnight at 105° C. and then cooled to RT and poured into water (300 mL). The resulting mixture was extracted with ethyl acetate (3×300 mL). The combined organic layers were dried over anhydrous sodium sulfate, filtered, and concentrated in vacuo. The crude product was purified via silica gel chromatography and eluted with ethyl acetate/petroleum ether (1:1) to afford tert-butyl 4-[4-(2-[[(benzyloxy)carbonyl]amino]ethyl)phenyl]piperazine-1-carboxylate as a yellow solid (26 g, 40%). LCMS (ESI, m/z): 440 $[M+H]^+$.

Step 3. tert-Butyl 4-[4-(2-[[(benzyloxy)carbonyl]amino]ethyl)-2-chlorophenyl]piperazine-1-carboxylate Into a 250-mL round-bottom flask was added tert-butyl 4-[4-(2-[[(benzyloxy)carbonyl]amino]ethyl)phenyl]piperazine-1-carboxylate (5.40 g, 12.3 mmol), DCM (100 mL), and N-chlorosuccinimide (1.64 g, 12.3 mmol). The resulting solution was stirred overnight at reflux and then cooled to RT and concentrated in vacuo. The crude product was purified via silica gel chromatography and eluted with ethyl acetate/petroleum ether (1:1) to afford tert-butyl 4-[4-(2-[[(benzyloxy)carbonyl]amino]ethyl)-2-chlorophenyl]piperazine-1-carboxylate as an orange oil (5.1 g, 88%). LCMS (ESI, m/z): 474 $[M+H]^+$.

Step 4. tert-Butyl 4-[4-(2-aminoethyl)-2-chlorophenyl]piperazine-1-carboxylate Into a 500-mL round-bottom flask, purged and maintained under an atmosphere of nitrogen, was added Raney Ni (5 g), methanol (250 mL), and tert-butyl 4-[4-(2-[[(benzyloxy)carbonyl]amino]ethyl)-2-chlorophenyl]piperazine-1-carboxylate (10.0 g, 21.1 mmol). The resulting mixture was sparged with hydrogen and then stirred overnight at RT under a hydrogen atmosphere. The solids were removed by filtration over Celite, and the filtrate was concentrated in vacuo to afford tert-butyl 4-[4-(2-aminoethyl)-2-chlorophenyl]piperazine-1-carboxylate as a gray solid (6.8 g, 95%) that was carried on without further purification. LCMS (ESI, m/z): 340 $[M+H]^+$.

Example 5: Intermediate 5. tert-Butyl 3-[4-(2-aminoethyl)-2-chlorophenyl]-3,8-diazabicyclo[3.2.1]octane-8-carboxylate

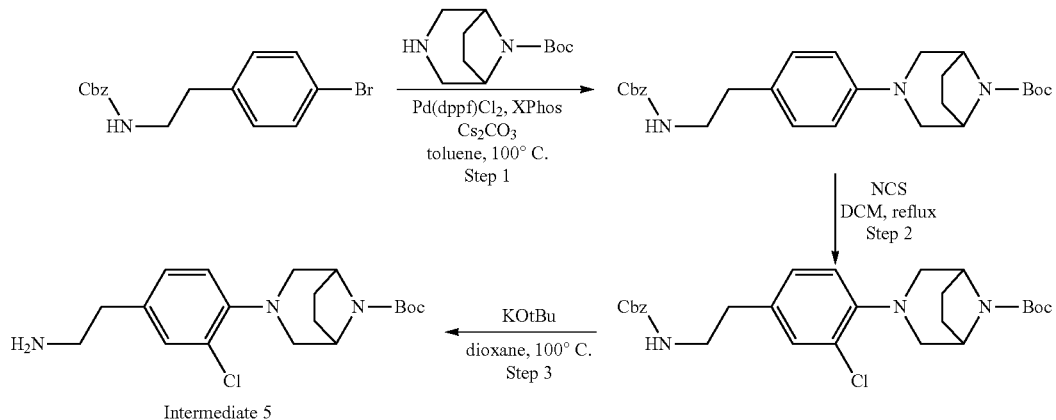

Intermediate 5

Step 1. tert-Butyl 3-[4-(2-[[(benzyloxy)carbonyl]amino]ethyl)phenyl]-3,8-diazabicyclo[3.2.1]octane-8-carboxylate Into a 50-mL 3-necked round-bottom flask, purged and maintained under an atmosphere of nitrogen, was added benzyl N-[2-(4-bromophenyl)ethyl]carbamate (0.692 g, 2.07 mmol), toluene (10 mL), tert-butyl 3,8-diazabicyclo[3.2.1]octane-8-carboxylate (0.400 g, 1.88 mmol), Cs$_2$CO$_3$ (1.85 g, 5.68 mmol), Pd(dppf)Cl$_2$ (0.078 g, 0.10 mmol), and XPhos (0.090 g, 0.20 mmol). The resulting solution was stirred overnight at 100° C. in an oil bath and then cooled to RT and concentrated in vacuo. The crude product was purified via silica gel chromatography and eluted with ethyl acetate/petroleum ether (1:10) to afford tert-butyl 3-[4-(2-[[(benzyloxy)carbonyl]amino]ethyl)phenyl]-3,8-diazabicyclo[3.2.1]octane-8-carboxylate as a yellow oil (440 mg, 50%). LCMS (ESI, m/z): 466 [M+H]$^+$.

Step 2. tert-Butyl 3-[4-(2-[[(benzyloxy)carbonyl]amino]ethyl)-2-chlorophenyl]-3,8-diazabicyclo[3.2.1]octane-8-carboxylate Into a 25-mL round-bottom flask was added tert-butyl 3-[4-(2-[[(benzyloxy)carbonyl]amino]ethyl)phenyl]-3,8-diazabicyclo[3.2.1]octane-8-carboxylate (0.44 g, 0.95 mmol), DCM (5 mL), and NCS (0.13 g 0.94 mmol). The resulting solution was stirred overnight at 40° C. in an oil bath. The reaction mixture was concentrated in vacuo. The crude product was purified via silica gel chromatography and eluted with ethyl acetate/petroleum ether (1:10) to afford tert-butyl 3-[4-(2-[[(benzyloxy)carbonyl]amino]ethyl)-2-chlorophenyl]-3,8-diazabicyclo[3.2.1]octane-8-carboxylate as a yellow oil (200 mg, 42%). LCMS (ESI, m/z): 500 [M+H]$^+$.

Step 3. tert-Butyl 3-[4-(2-aminoethyl)-2-chlorophenyl]-3,8-diazabicyclo[3.2.1]octane-8-carboxylate Into a 50-mL round-bottom flask was added tert-butyl 3-[4-(2-[[(benzyloxy)carbonyl]amino]ethyl)-2-chlorophenyl]-3,8-diazabicyclo[3.2.1]octane-8-carboxylate (0.20 g, 0.40 mmol), 1,4-dioxane (6 mL), and potassium tert-butoxide (0.135 g, 1.20 mmol). The resulting solution was stirred for 2 h at 100° C. in an oil bath and then cooled to RT. The reaction mixture was diluted with water (10 mL) and then extracted with dichloromethane (3×10 mL). The combined organic layers were washed with brine, dried over anhydrous sodium sulfate, filtered, and concentrated in vacuo to afford tert-butyl 3-[4-(2-aminoethyl)-2-chlorophenyl]-3,8-diazabicyclo[3.2.1]octane-8-carboxylate as an off-white solid (140 mg, 96%). LCMS (ESL m/z): 366 [M+H]$^+$.

Example 6: Intermediate 6. tert-Butyl 3-(4-(2-aminoethyl)phenyl)-3,8-diazabicyclo[3.2.1]octane-8-carboxylate

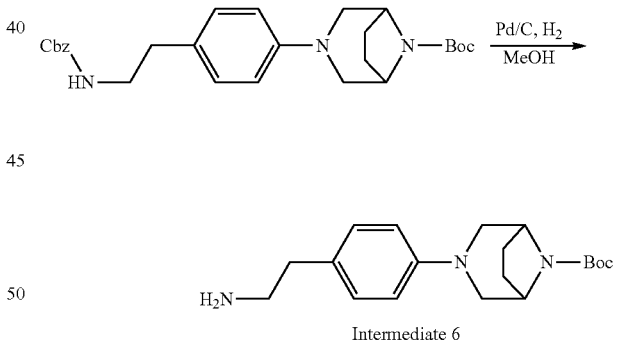

Intermediate 6

Into a 50-mL round-bottom flask, purged and maintained under an atmosphere of nitrogen, was added tert-butyl 3-[4-(2-[[(benzyloxy)carbonyl]amino]ethyl)phenyl]-3,8-diazabicyclo[3.2.1]octane-8-carboxylate (0.25 g, 0.54 mmol), methanol (8 mL), and 10% palladium on carbon (100 mg). The resulting mixture was sparged with hydrogen and then stirred for 2 h at RT under a hydrogen atmosphere. The solids were removed by filtration over Celite and the filtrate was concentrated in vacuo to afford tert-butyl 3-(4-(2-aminoethyl)phenyl)-3,8-diazabicyclo[3.2.1]octane-8-carboxylate as a yellow oil which was carried on without further purification (170 mg, 96%). LCMS (ESI, m/z): 332 [M+H]$^+$.

Example 7-1: Intermediate 7-1. tert-Butyl 3-[4-(2-aminoethyl)-2,5-difluorophenyl]-3,8-diazabicyclo[3.2.1]octane-8-carboxylate

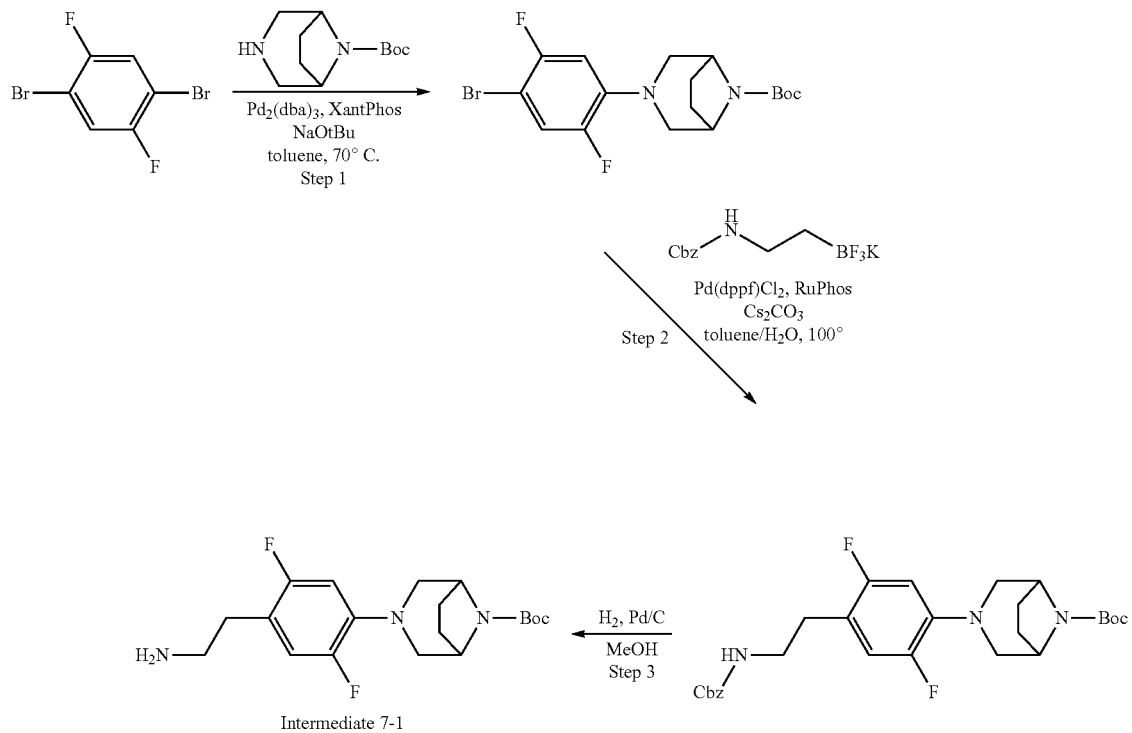

Intermediate 7-1

Step 1. tert-Butyl 3-(4-bromo-2,5-difluorophenyl)-3,8-diazabicyclo[3.2.1]octane-8-carboxylate Into a 1-L round-bottom flask, purged and maintained with an inert atmosphere of nitrogen, was added 1,4-dibromo-2,5-difluorobenzene (15.0 g, 55.0 mmol), tert-butyl 3,8-diazabicyclo[3.2.1]octane-8-carboxylate (10.6 g, 49.9 mmol), $Pd_2(dba)_3CHCl_3$ (2.59 g, 2.50 mmol), XantPhos (2.89 g, 5.00 mmol), sodium tert-butoxide (9.60 g, 99.9 mmol), and toluene (500 mL). The resulting solution was stirred for 45 min at 70° C. and then cooled to RT and quenched by the addition water (100 mL). The resulting solution was extracted with ethyl acetate (3×100 mL) and the combined organic layers were dried over anhydrous sodium sulfate, filtered, and concentrated in vacuo. The crude product was purified by silica gel column and eluted with ethyl acetate/petroleum ether (1:10) to afford tert-butyl 3-(4-bromo-2,5-difluorophenyl)-3,8-diazabicyclo[3.2.1]octane-8-carboxylate as light yellow oil (15 g, 67%). LCMS (ESI, m/z): 403, 405 [M+H]$^+$.

Step 2. tert-Butyl 3-[4-(2-[[(benzyloxy)carbonyl]amino]ethyl)-2,5-difluorophenyl]-3,8-diazabicyclo[3.2.1]octane-8-carboxylate Into a 1-L round-bottom flask, purged and maintained with an inert atmosphere of nitrogen, was added tert-butyl 3-(4-bromo-2,5-difluorophenyl)-3,8-diazabicyclo[3.2.1]octane-8-carboxylate (14.0 g, 34.7 mmol), potassium[2-(benzyloxycarbonylamino)ethyl]trifluoroborate (10.9 g, 38.2 mmol), Pd(dppf)Cl$_2$ (2.55 g, 3.49 mmol), RuPhos (3.25 g, 6.96 mmol), Cs$_2$CO$_3$ (22.7 g, 69.7 mmol), toluene (500 mL), and water (100 mL). The reaction mixture was stirred for 3 h at 100° C. and then cooled to room temperature. The resulting mixture was extracted with ethyl acetate (3×100 mL) and the combined organic layers were dried over anhydrous sodium sulfate, filtered, and concentrated in vacuo. The crude product was purified via silica gel chromatography and eluted with ethyl acetate/petroleum ether (PE/EA=100:1 to 5:1) to afford tert-butyl 3-[4-(2-[[(benzyloxy)carbonyl]amino]ethyl)-2,5-difluorophenyl]-3,8-diazabicyclo[3.2.1]octane-8-carboxylate as a yellow oil (12 g, 62%). LCMS (ESI, m/z): 502 [M+H]$^+$.

Step 3. tert-Butyl 3-[4-(2-aminoethyl)-2,5-difluorophenyl]-3,8-diazabicyclo[3.2.1]octane-8-carboxylate Into a 1-L round-bottom flask, purged and maintained under an atmosphere of nitrogen, was added tert-butyl 3-[4-(2-[[(benzyloxy)carbonyl]amino]ethyl)-2,5-difluorophenyl]-3,8-diazabicyclo[3.2.1]octane-8-carboxylate (12.0 g, 23.9 mmol), 10% palladium on carbon (12 g), and methanol (500 mL). The resulting mixture was sparged with H$_2$ and then stirred for 1 h at 20° C. under a hydrogen atmosphere. The solids were removed by filtration over Celite, and the filtrate was concentrated in vacuo. The crude product was purified via silica gel chromatography and eluted with dichloromethane/methanol (100:1 to 10:1) to afford tert-butyl 3-[4-(2-aminoethyl)-2,5-difluorophenyl]-3,8-diazabicyclo[3.2.1]octane-8-carboxylate as a light yellow oil (8.91 g, 99%). LCMS (ESI, m/z): 368 [M+H]$^+$.

The Intermediate in Table 1 below was synthesized according to the procedures outlined above for Example 7-1, Intermediate 7-1, using the appropriate synthetic precursors.

TABLE 1

| Intermediate No.: | Precursor Used (Notes) | MS (ESI, m/z) [M + H] |
|---|---|---|
| Intermediate 7-2. tert-Butyl 4-(4-(2-aminoethyl)-2,5-difluorophenyl)piperazine-1-carboxylate | tert-Butyl piperazine-1-carboxylate and 1,4-dibromo-2,5-difluorobenzene (Step 1 was conducted at 80° C., Step 2 was conducted at 95° C.) | 342 |
| Intermediate 7-3. tert-Butyl 7-(4-(2-aminoethyl)-2,5-difluorophenyl)-9-oxa-3,7-diazabicyclo[3.3.1]nonane-3-carboxylate | tert-Butyl 9-oxa-3,7-diazabicyclo[3.3.1]nonane-3-carboxylate and 1,4-dibromo-2,5-difluorobenzene Step 2 was conducted in DMF and water.) | 384 |

Example 8: Intermediate 8. tert-Butyl 3-(4-bromo-2-cyanophenyl)-3,8-diazabicyclo[3.2.1]octane-8-carboxylate

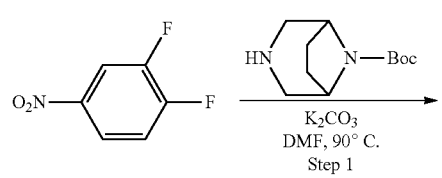

Intermediate 8

Into a 100-mL round-bottom flask was added tert-butyl 3,8-diazabicyclo[3.2.1]octane-8-carboxylate (1.00 g, 4.71 mmol), 5-bromo-2-fluorobenzonitrile (1.88 g, 9.40 mmol), DIEA (1.83 g, 2.47 mL, 14.2 mmol), and DMSO (25 mL). The resulting mixture was stirred for 24 h at 80° C. in an oil bath and then cooled to RT and quenched by the addition of water (20 mL). The resulting solution was extracted with ethyl acetate (2×20 mL), and the combined organic layers were dried over anhydrous sodium sulfate, filtered, and concentrated in vacuo. The crude product was purified via silica gel chromatography and eluted with ethyl acetate/petroleum ether (1:5) to afford tert-butyl 3-(4-bromo-2-cyanophenyl)-3,8-diazabicyclo[3.2.1]octane-8-carboxylate as a yellow oil (550 mg, 30%). LCMS (ESI, m/z): 392, 394 [M+H]$^+$.

Example 9: Intermediate 9. tert-Butyl 3-(4-bromo-2-fluorophenyl)-3,8-diazabicyclo[3.2.1]octane-8-carboxylate

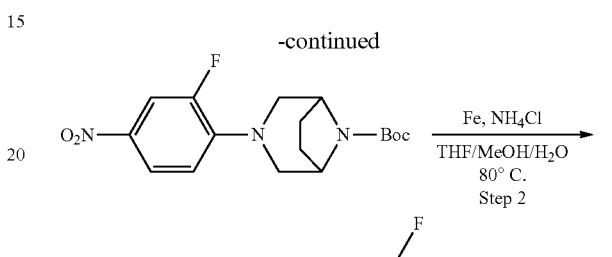

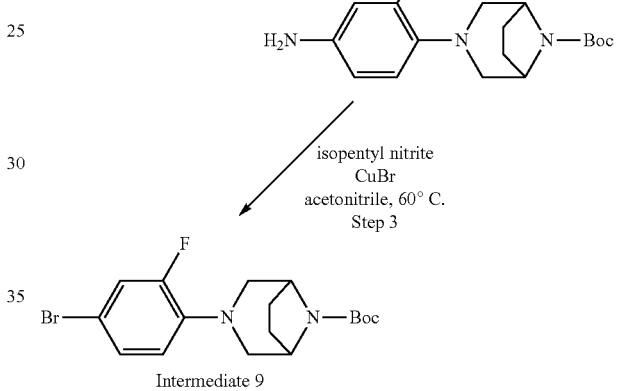

Intermediate 9

Step 1. tert-Butyl 3-(2-fluoro-4-nitrophenyl)-3,8-diazabicyclo[3.2.1]octane-8-carboxylate Into a 100-mL round-bottom flask, purged and maintained with an inert atmosphere of nitrogen, was added 1,2-difluoro-4-nitrobenzene (1.00 g, 6.29 mmol), tert-butyl 3,8-diazabicyclo[3.2.1]octane-8-carboxylate (1.47 g, 6.92 mmol), potassium carbonate (2.60 g, 18.8 mmol), and DMF (10 mL). The resulting mixture was stirred for 4 h at 90° C. and then cooled to RT and quenched by the addition of water (20 mL). The resulting solution was extracted with ethyl acetate (3×10 mL) and the combined organic layers were dried over anhydrous sodium sulfate, filtered, and concentrated in vacuo. The crude product was purified via silica gel chromatography and eluted with ethyl acetate/petroleum ether (1:10) to afford tert-butyl 3-(2-fluoro-4-nitrophenyl)-3,8-diazabicyclo[3.2.1]octane-8-carboxylate as a yellow solid (1.93 g, 87%). LCMS (ESI, m/z): 352 [M+H]$^+$.

Step 2. tert-Butyl 3-(4-amino-2-fluorophenyl)-3,8-diazabicyclo[3.2.1]octane-8-carboxylate Into a 100-mL round-bottom flask was added tert-butyl 3-(2-fluoro-4-nitrophenyl)-3,8-diazabicyclo[3.2.1]octane-8-carboxylate (1.63 g, 4.64 mmol), iron powder (1.30 g), ammonium chloride (1.23 g, 23.0 mmol), tetrahydrofuran (18 mL), methanol (18 mL), and water (3 mL). The resulting mixture was stirred for 4 h at 80° C. and cooled to RT. The solids were removed by filtration, and the filtrate was diluted with ethyl acetate (60 mL) and washed with water (20 mL). The organic layer was dried over anhydrous sodium sulfate, filtered, and concentrated in vacuo to afford tert-butyl 3-(4-amino-2-fluorophenyl)-3,8-diazabicyclo[3.2.1]octane-8-carboxylate as a yellow oil (1.71 g). The material was used without further purification. LCMS (ESI, m/z): 322 [M+H]$^+$.

Step 3. tert-Butyl 3-(4-bromo-2-fluorophenyl)-3,8-diazabicyclo[3.2.1]octane-8-carboxylate Into a 100-mL round-bottom flask, purged and maintained with an inert atmosphere of nitrogen, was added tert-butyl 3-(4-amino-2-fluorophenyl)-3,8-diazabicyclo[3.2.1]octane-8-carboxylate (1.71 g, 5.32 mmol), acetonitrile (30 mL), CuBr (1.53 g, 10.7 mmol), and isopentyl nitrite (0.938 g, 8.02 mmol). The resulting mixture was stirred for 3 h at 60° C. and then cooled to RT and concentrated in vacuo. The crude product was purified via silica gel chromatography and eluted with ethyl acetate/petroleum ether (1:8) to afford tert-butyl 3-(4-bromo-2-fluorophenyl)-3,8-diazabicyclo[3.2.1]octane-8-carboxylate as a yellow oil (448 mg, 22%). LCMS (ESI, m/z): 385, 387 [M+H]$^+$.

The Intermediates in Table 2 below were synthesized according to the procedures outlined above for Example 7-1, Intermediate 7-1 (Steps 2 and 3) using the appropriate synthetic precursors.

TABLE 2

| Intermediate No.: | Precursor Used (Notes) | MS (ESI, m/z) [M + H] |
|---|---|---|
| Intermediate 10-1. tert-Butyl 3-[4-(2-aminoethyl)-2-cyanophenyl]-3,8-diazabicyclo[3.2.1]octane-8-carboxylate | tert-Butyl 3-(4-bromo-2-cyanophenyl)-3,8-diazabicyclo[3.2.1]octane-8-carboxylate (Step 2 was conducted with THF as the solvent) | 357 |
| Intermediate 10-2. tert-Butyl 3-[4-(2 aminoethyl)-2-fluorophenyl]-3,8-diazabicyclo[3.2.1]octane-8-carboxylate | tert-Butyl 3-(4-bromo-2-fluorophenyl)-3,8-diazabicyclo[3.2.1]octane-8-carboxylate | 350 |

Example 11-1: Intermediate 11-1. tert-Butyl 3-[4-(2-aminoethyl)-3-fluorophenyl]-3,8-diazabicyclo[3.2.1]octane-8-carboxylate

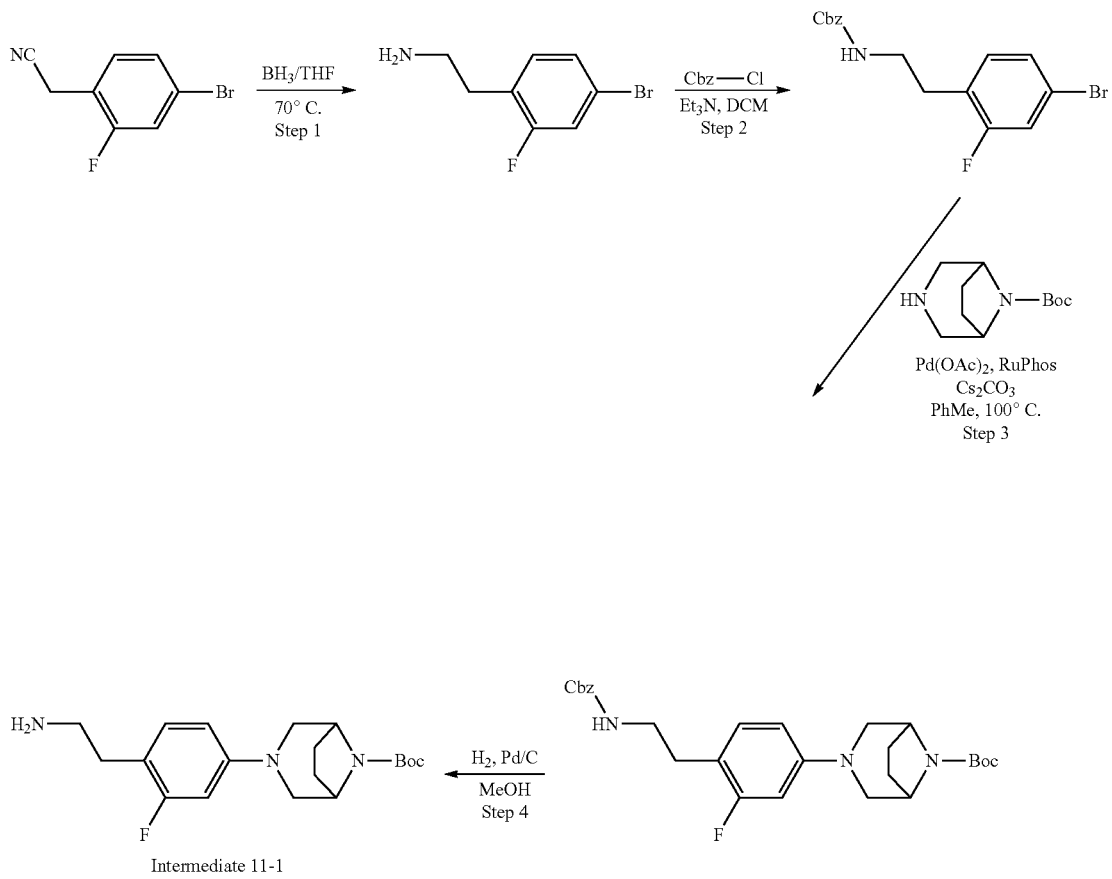

Intermediate 11-1

Step 1. 2-(4-Bromo-2-fluorophenyl)ethan-1-amine

Into a 100-mL round-bottom flask was added 2-(4-bromo-2-fluorophenyl)acetonitrile (1.20 g, 5.61 mmol), borane tetrahydrofuran complex (1M; 16.8 mL, 16.8 mmol), and THF (20 mL). The resulting solution was stirred for 18 h at 70° C. in an oil bath and then cooled to RT and quenched by the addition of methanol (5 mL). The resulting mixture was concentrated in vacuo to afford 2-(4-bromo-2-fluorophenyl)ethan-1-amine as a brown oil that was carried on without further purification (900 mg, 74%). LCMS (ESI, m/z): 218, 220 [M+H]⁺.

Step 2. Benzyl N-[2-(4-bromo-2-fluorophenyl)ethyl]carbamate

Into a 100-mL round-bottom flask was added 2-(4-bromo-2-fluorophenyl)ethan-1-amine (0.900 g, 4.13 mmol), benzyl chloroformate (0.915 g, 0.763 mL, 5.37 mmol), triethylamine (1.25 g, 1.72 mL, 12.38 mmol), and dichloromethane (10 mL). The resulting solution was stirred for 2 h at 20° C. and then quenched by the addition of water (10 mL) and extracted with ethyl acetate (3×20 mL). The organic layers were combined, dried over anhydrous sodium sulfate, filtered, and concentrated in vacuo. The crude product was purified via silica gel chromatography and eluted with ethyl acetate/petroleum ether (PE/EA=100:1 to 10:1) to afford benzyl N-[2-(4-bromo-2-fluorophenyl)ethyl]carbamate as a yellow solid (1.2 g, 83%). LCMS (ESI, m/z): 352, 354 [M+H]⁺.

Step 3. tert-Butyl 8-[4-(2-[[(benzyloxy)carbonyl]amino]ethyl)-3-fluorophenyl]-3,8-diazabicyclo[3.2.1]octane-3-carboxylate Into a 50-mL 3-necked round-bottom flask, purged and maintained with an inert atmosphere of nitrogen, was added benzyl N-[2-(4-bromo-2-fluorophenyl)ethyl]carbamate (0.500 g, 1.42 mmol), tert-butyl 3,8-diazabicyclo[3.2.1]octane-3-carboxylate (0.320 g, 1.51 mmol), Cs₂CO₃ (1.40 g, 4.30 mmol), Pd(OAc)₂ (0.032 g, 0.14 mmol), RuPhos (0.13 g, 0.29 mmol), and toluene (10 mL). The resulting mixture was stirred for 2 h at 100° C. in an oil bath and then cooled to RT and quenched by the addition of water (20 mL). The resulting solution was extracted with ethyl acetate (3×20 mL) and the combined organic layers were dried over anhydrous sodium sulfate, filtered, and concentrated in vacuo. The crude product was purified via silica gel chromatography and eluted with ethyl acetate/petroleum ether (PE/EA=100:1 to 3:1) to afford tert-butyl 8-[4-(2-[[(benzyloxy)carbonyl]amino]ethyl)-3-fluorophenyl]-3,8-diazabicyclo[3.2.1]octane-3-carboxylate as light yellow oil (220 mg, 32%). LCMS (ESI, m/z): 484 [M+H]⁺.

Step 4. tert-Butyl 3-[4-(2-aminoethyl)-3-fluorophenyl]-3,8-diazabicyclo[3.2.1]octane-8-carboxylate Into a 50-mL round-bottom flask, purged and maintained under an atmosphere of nitrogen, was added tert-butyl 8-[4-(2-[[(benzyloxy)carbonyl]amino]ethyl)-3-fluorophenyl]-3,8-diazabicyclo[3.2.1]octane-3-carboxylate (0.22 g, 0.45 mmol), and methanol (10 mL) followed by the addition of 10% palladium on carbon (220 mg). The reaction mixture was sparged with hydrogen and stirred for 2 h at 20° C. under a hydrogen atmosphere (balloon pressure). The solids were removed by filtration over Celite and the filtrate was concentrated in vacuo to afford tert-butyl 3-[4-(2-aminoethyl)-3-fluorophenyl]-3,8-diazabicyclo[3.2.1]octane-8-carboxylate as a light yellow oil which was carried on without further purification (70 mg, 40%). LCMS (ESI, m/z): 350 [M+H]⁺.

The Intermediate in Table 3 below was synthesized according to the procedures outlined above for Example 11-1, Intermediate 11-1, using the appropriate synthetic precursors.

TABLE 3

| Intermediate No.: | Precursors Used (Notes) | MS (ESI, m/z) [M + H] |
|---|---|---|
| Intermediate 11-2. tert-Butyl 3-(4-(2-aminoethyl)-3,5-difluorophenyl)-3,8-diazabicyclo[3.2.1]octane-8-carboxylate | 2-(4-Bromo-2,6-difluorophenyl)acetonitrile (XPhos was used instead of RuPhos in Step 3; EtOH was used as solvent in Step 4) | 368 |

Example 12-1: Intermediate 12-1. tert-butyl 3-[4-(1-aminopropan-2-yl)-2,5-difluorophenyl]-3,8-diazabicyclo[3.2.1]octane-8-carboxylate

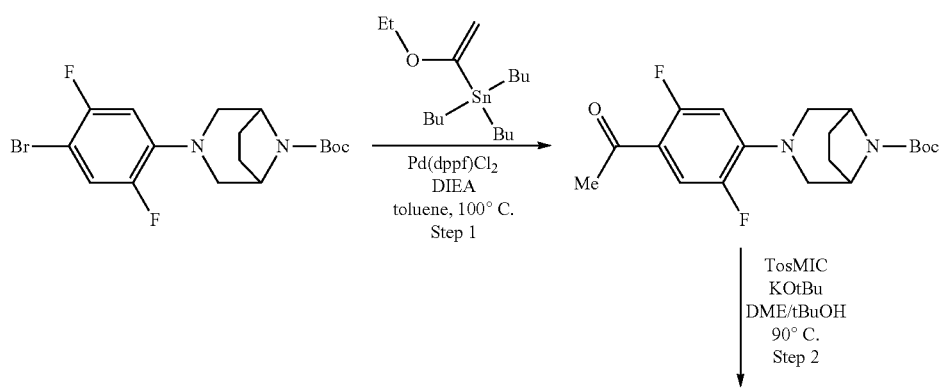

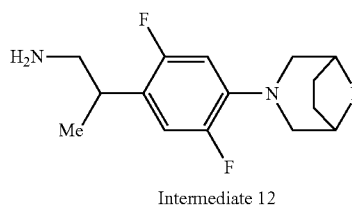 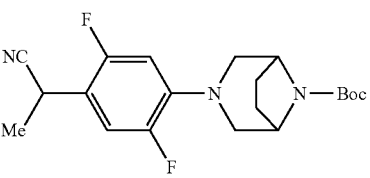

Intermediate 12

Step 1. tert-Butyl 3-(4-acetyl-2,5-difluorophenyl)-3,8-diazabicyclo[3.2.1]octane-8-carboxylate Into a 250-mL round-bottom flask, purged and maintained with an inert atmosphere of nitrogen, was added tert-butyl 3-(4-bromo-2,5-difluorophenyl)-3,8-diazabicyclo[3.2.1]octane-8-carboxylate (1.30 g, 3.22 mmol), tributyl(1-ethoxyvinyl)stannane (1.75 g, 1.64 mL, 4.85 mmol), Pd(dppf)Cl₂CH₂Cl₂ (0.53 g, 0.64 mmol), DIEA (1.25 g, 1.68 mL, 9.67 mmol), and toluene (100 mL). The resulting solution was stirred for 18 h at 100° C. and then cooled to RT and quenched by the addition of saturated aqueous ammonium chloride solution (30 mL). The resulting mixture was extracted with ethyl acetate (3×100 mL) and the combined organic layers were dried over sodium sulfate, filtered, and concentrated in vacuo. The crude product was purified via silica gel chromatography and eluted with ethyl acetate/petroleum ether (1:100 to 1:10) to afford tert-butyl 3-(4-acetyl-2,5-difluorophenyl)-3,8-diazabicyclo[3.2.1]octane-8-carboxylate as a light yellow oil (460 mg, 35%). LCMS (ESI, m/z): 367 [M+H]⁺.

Step 2. tert-Butyl 3-[4-(1-cyanoethyl)-2,5-difluorophenyl]-3,8-diazabicyclo[3.2.1]octane-8-carboxylate Into a 100-mL round-bottom flask was added tert-butyl 3-(4-acetyl-2,5-difluorophenyl)-3,8-diazabicyclo[3.2.1]octane-8-carboxylate (0.420 g, 1.15 mmol), p-toluenesulfonyl isocyanide (0.336 g, 1.71 mmol), potassium t-butoxide (0.321 g, 2.86 mmol), t-butanol (10 mL), and ethylene glycol dimethyl ether (10 mL). The resulting solution was stirred for 18 h at 90° C. and then cooled to RT and quenched by the addition of water (50 mL). The resulting mixture was extracted with ethyl acetate (3×20 mL) and the combined organic layers were dried over sodium sulfate, filtered, and concentrated in vacuo. The crude product was purified via silica gel chromatography and eluted with ethyl acetate/petroleum ether (1:100 to 1:10) to afford tert-butyl 3-[4-(1-cyanoethyl)-2,5-difluorophenyl]-3,8-diazabicyclo[3.2.1]octane-8-carboxylate as a light yellow solid (350 mg, 73%). LCMS (ESI, m/z): 378 [M+H]⁺.

Step 3. tert-Butyl 3-[4-(1-aminopropan-2-yl)-2,5-difluorophenyl]-3,8-diazabicyclo[3.2.1]octane-8-carboxylate Into a 50-mL round-bottom flask, purged and maintained under an atmosphere of nitrogen, was added tert-butyl 3-[4-(1-cyanoethyl)-2,5-difluorophenyl]-3,8-diazabicyclo[3.2.1]octane-8-carboxylate (0.35 g, 0.93 mmol), Raney Ni (0.350 g), and a solution of ammonia in methanol (7 M, 20 mL). The resulting mixture was sparged with H₂ and then stirred for 2 h at 20° C. under a hydrogen atmosphere (balloon pressure). The solids were removed by filtration over Celite and the filtrate was concentrated in vacuo to afford tert-butyl 3-[4-(1-aminopropan-2-yl)-2,5-difluorophenyl]-3,8-diazabicyclo[3.2.1]octane-8-carboxylate as a light yellow solid (200 mg, 51%). LCMS (ESI, m/z): 382 [M+H]⁺.

The Intermediate in Table 4 below was synthesized according to the procedures outlined above for Example 12-1, Intermediate 12-1, using the appropriate synthetic precursors.

TABLE 4

| Intermediate No.: | Precursors Used (Notes) | MS (ESI, m/z) [M + H] |
|---|---|---|
| Intermediate 12-2. tert-Butyl 7-(4-(1-aminopropan-2-yl)-2,5-difluorophenyl)-9-oxa-3,7-diazabicyclo[3.3.1]nonane-3-carboxylate | tert-Butyl 7-(4-bromo-2,5-.difluorophenyl)-9-oxa-3,7-diazabicyclo[3.3.1]nonane-3-carboxylate (Step 1 was conducted at 80° C.) | 398 |

Example 13-1: Intermediate 13-1. tert-Butyl 3-[4-(1-aminopropan-2-yl)-3-fluorophenyl]-3,8-diazabicyclo[3.2.1]octane-8-carboxylate

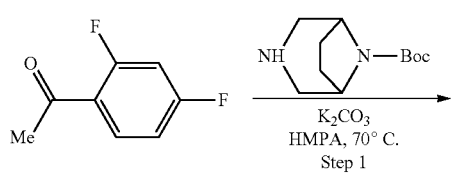

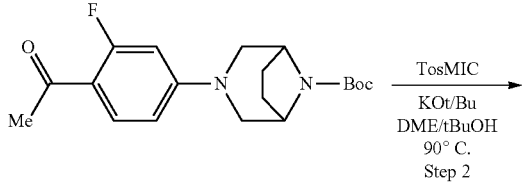

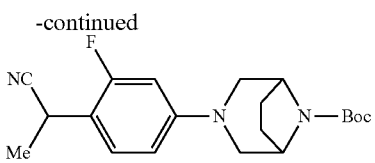

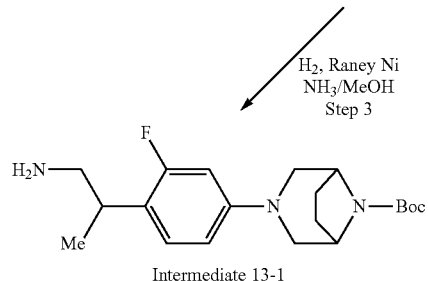

Intermediate 13-1

Step 1. tert-Butyl 3-(4-acetyl-3-fluorophenyl)-3,8-diazabicyclo[3.2.1]octane-8-carboxylate Into a 100-mL round-bottom flask was added 1-(2,4-difluorophenyl)ethan-1-one (2.65 g, 17.0 mmol), tert-butyl 3,8-diazabicyclo[3.2.1]octane-8-carboxylate (3.00 g, 14.1 mmol), potassium carbonate (5.86 g, 42.4 mmol), and HMPA (30 mL). The resulting solution was stirred overnight at 70° C. in an oil bath and then cooled to RT and quenched by the addition of water (30 mL). The resulting solution was extracted with ethyl acetate (3×30 mL) and the combined organic layers were dried over anhydrous sodium sulfate, filtered, and concentrated in vacuo. The crude product was purified via silica gel chromatography and eluted with ethyl acetate/petroleum ether (1:5) to afford tert-butyl 3-(4-acetyl-3-fluorophenyl)-3,8-diazabicyclo[3.2.1]octane-8-carboxylate as a brown oil (1.8 g, 30%). LCMS (ESI, m/z): 349 [M+H]+.

Step 2. tert-Butyl 3-[4-(1-cyanoethyl)-3-fluorophenyl]-3,8-diazabicyclo[3.2.1]octane-8-carboxylate Into a 100-mL round-bottom flask was added tert-butyl 3-(4-acetyl-3-fluorophenyl)-3,8-diazabicyclo[3.2.1]octane-8-carboxylate (1.80 g, 5.17 mmol), KOt-Bu (1.45 g, 13.0 mmol), p-toluenesulfonyl isocyanide (1.51 g, 7.74 mmol), tert-butanol (20 mL), and ethylene glycol dimethyl ether (20 mL). The resulting solution was stirred overnight at 90° C. in an oil bath and then cooled and quenched by the addition water (20 mL). The resulting solution was extracted with ethyl acetate (3×20 mL) and the combined organic layers were dried over anhydrous sodium sulfate, filtered, and concentrated in vacuo. The crude product was purified via silica gel chromatography and eluted with ethyl acetate/petroleum ether (1:5) to afford tert-butyl 3-[4-(1-cyano-ethyl)-3-fluorophenyl]-3,8-diazabicyclo[3.2.1]octane-8-carboxylate as a brown oil (1.2 g, 65%). LCMS (ESI, m/z): 360 [M+H]+.

Step 3. tert-Butyl 3-[4-(1-aminopropan-2-yl)-3-fluorophenyl]-3,8-diazabicyclo[3.2.1]octane-8-carboxylate Into a 100-mL round-bottom flask, purged and maintained under an atmosphere of nitrogen, was added tert-butyl 3-[4-(1-cyanoethyl)-3-fluorophenyl]-3,8-diazabicyclo[3.2.1]octane-8-carboxylate (1.00 g, 2.78 mmol), NH₃ in MeOH (7 M, 20 mL), and Raney Ni (500 mg). The reaction mixture was sparged with hydrogen and stirred for 2 h at RT under a hydrogen atmosphere (balloon pressure). The solids were removed by filtration over Celite and the filtrate was concentrated in vacuo. The crude product was purified via silica gel chromatography and eluted with dichloromethane/methanol (10:1) to afford tert-butyl 3-[4-(1-aminopropan-2-yl)-3-fluorophenyl]-3,8-diazabicyclo[3.2.1]octane-8-carboxylate as a yellow oil (800 mg, 79%). LCMS (ESI, m/z): 364 [M+H]+.

The Intermediate in Table 5 below was synthesized according to the procedures outlined above for Example 13-1, Intermediate 13-1, using the appropriate synthetic precursors.

TABLE 5

| Intermediate No.: | Precursors Used (Notes) | MS (ESI, m/z) [M + H] |
|---|---|---|
| Intermediate 13-2. tert-Butyl 3-[4-(1-aminopropan-2-yl)-2-fluorophenyl]-3,8-diazabicyclo[3.2.1]octane-8-carboxylate | 1-(3,4-Difluorophenyl)ethan-1-one and tert-butyl 3,8-diazabicyclo[3.2.1]octane-8-carboxylate | 364 |

Example 14: Intermediate 14. tert-Butyl 3-(4-(1-aminopropan-2-yl)-2-cyanophenyl)-3,8-diazabicyclo[3.2.1]octane-8-carboxylate

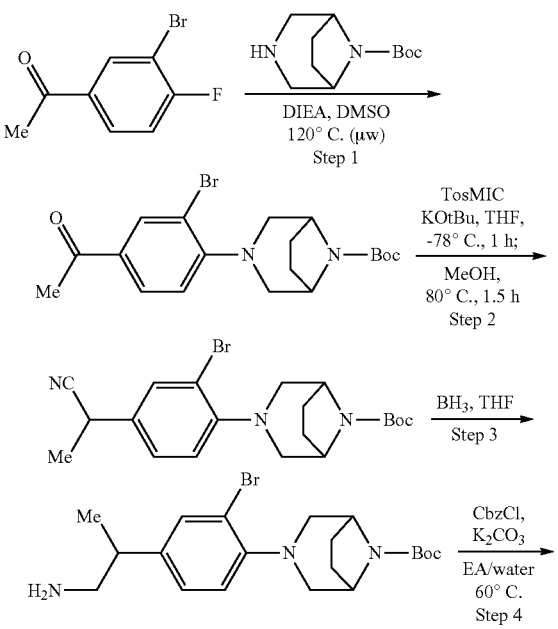

-continued

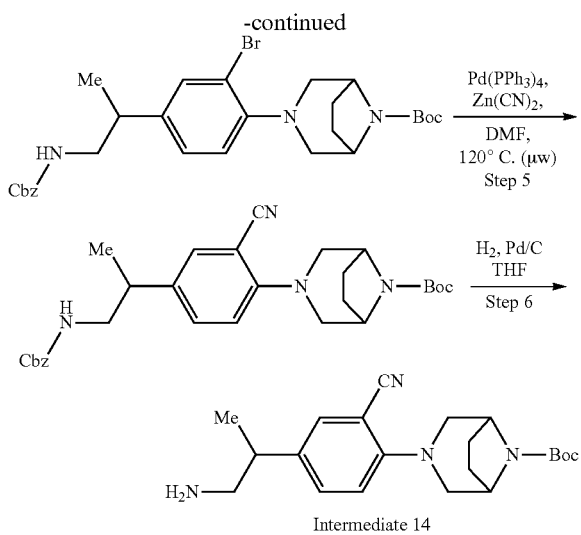

Intermediate 14

Step 1. tert-Butyl 3-(4-acetyl-2-bromophenyl)-3,8-diazabicyclo[3.2.1]octane-8-carboxylate Into a 20-mL microwave tube was added 1-(3-bromo-4-fluorophenyl)ethan-1-one (3.00 g, 13.8 mmol), tert-butyl 3,8-diazabicyclo[3.2.1]octane-8-carboxylate (3.67 g, 17.3 mmol), DIEA (5.48 g, 7.39 mL, 42.4 mmol), and DMSO (8 mL). The resulting solution was heated at 120° C. for 4 h under microwave irradiation. The reaction mixture was cooled to RT and then poured into water (30 mL). The resulting mixture was extracted with ethyl acetate (3×30 mL), and the combined organic layers were dried over anhydrous sodium sulfate, filtered, and concentrated in vacuo. The crude product was purified via silica gel chromatography and eluted with ethyl acetate/petroleum ether (1:5) to afford tert-butyl 3-(4-acetyl-2-bromophenyl)-3,8-diazabicyclo[3.2.1]octane-8-carboxylate as a yellow oil (1.5 g, 27%). LCMS (ESI, m/z): 409, 411[M+H]$^+$.

Step 2. tert-Butyl 3-[2-bromo-4-(1-cyanoethyl)phenyl]-3,8-diazabicyclo[3.2.1]octane-8-carboxylate Into a 100-mL 3-necked round-bottom flask, purged and maintained with an inert atmosphere of nitrogen, was added potassium t-butoxide (0.480 g, 4.28 mmol) and THF (15 mL) followed by the dropwise addition of a solution of p-toluenesulfonyl isocyanide (0.500 g, 2.56 mmol) in tetrahydrofuran (3 mL) with stirring at −78° C. The resulting solution was stirred for 15 minutes at −78° C. and then a solution of tert-butyl 3-(4-acetyl-2-bromophenyl)-3,8-diazabicyclo[3.2.1]octane-8-carboxylate (0.700 g, 1.71 mmol) in tetrahydrofuran (5 mL) was added dropwise with stirring at −78° C. The resulting mixture was then stirred for an additional 1.5 h at this temperature. Methanol (10 mL) was added, and the resulting solution was heated to 80° C. and stirred for another 30 minutes. The reaction was then cooled to RT and was concentrated in vacuo. The crude product was purified via silica gel chromatography and eluted with ethyl acetate/petroleum ether (1:5) to afford tert-butyl 3-[2-bromo-4-(1-cyanoethyl)phenyl]-3,8-diazabicyclo[3.2.1]octane-8-carboxylate as a yellow oil (500 mg, 70%). LCMS (ESI, m/z): 420, 422[M+H]$^+$.

Step 3. tert-Butyl 3-[4-(1-aminopropan-2-yl)-2-bromophenyl]-3,8-diazabicyclo[3.2.1]octane-8-carboxylate Into a 250-mL round-bottom flask was added tert-butyl 3-[2-bromo-4-(1-cyanoethyl)phenyl]-3,8-diazabicyclo[3.2.1]octane-8-carboxylate (1.50 g, 3.57 mmol) and borane tetrahydrofuran complex (1 M, 20 mL, 20 mmol). The resulting solution was stirred for 2 h at 25° C. and then quenched by the addition of methanol (30 mL). The resulting mixture was concentrated in vacuo. The crude product was purified via silica gel chromatography and eluted with dichloromethane/methanol (10:1) to afford tert-butyl 3-[4-(1-aminopropan-2-yl)-2-bromophenyl]-3,8-diazabicyclo[3.2.1]octane-8-carboxylate as a white solid (1.3 g, 86%). LCMS (ESI, m/z): 424, 426[M+H]$^+$.

Step 4. tert-Butyl 3-[4-(1-[[(benzyloxy)carbonyl]amino]propan-2-yl)-2-bromophenyl]-3,8-diazabicyclo[3.2.1]octane-8-carboxylate Into a 100-mL round-bottom flask was added tert-butyl 3-[4-(1-aminopropan-2-yl)-2-bromophenyl]-3,8-diazabicyclo[3.2.1]octane-8-carboxylate (1.40 g, 3.30 mmol), potassium carbonate (1.37 g, 9.91 mmol), ethyl acetate (20 mL), water (20 mL), and CbzCl (0.619 g, 0.516 mL, 3.63 mmol). The resulting mixture was stirred for 3 h at 60° C. in an oil bath and then cooled to RT. The reaction mixture was diluted with water (100 mL) and then extracted with ethyl acetate (3×20 mL). The combined organic layers were dried over anhydrous sodium sulfate, filtered, and concentrated in vacuo. The crude residue was purified via silica gel chromatography and eluted with ethyl acetate/petroleum ether (1:1) to afford tert-butyl 3-[4-(1-[[(benzyloxy)carbonyl]amino]propan-2-yl)-2-bromophenyl]-3,8-diazabicyclo[3.2.1]octane-8-carboxylate as a light yellow oil (1.0 g, 54%). LCMS (ESI, m/z): 558, 560[M+H]$^+$.

Step 5. tert-Butyl 3-[4-(1-[[(benzyloxy)carbonyl]amino]propan-2-yl)-2-cyanophenyl]-3,8-diazabicyclo[3.2.1]octane-8-carboxylate Into a 10-mL microwave tube, purged and maintained with an inert atmosphere of nitrogen, was placed tert-butyl 3-[4-(1-[[(benzyloxy)carbonyl]amino]propan-2-yl)-2-bromophenyl]-3,8-diazabicyclo[3.2.1]octane-8-carboxylate (0.800 mg, 1.43 mmol), Zn(CN)$_2$ (0.167 g, 1.42 mmol), Pd(PPh$_3$)$_4$ (0.166 g, 0.14 mmol), and DMF (3 mL). The resulting mixture was heated at 120° C. for 4 h under microwave irradiation. The reaction mixture was then cooled to RT, poured into water (50 mL), and extracted with ethyl acetate (3×10 mL). The combined organic layers were concentrated in vacuo and the crude product was purified via Prep-TLC plate and eluted with ethyl acetate/petroleum ether (1:3) to afford tert-butyl 3-[4-(1-[[(benzyloxy)carbonyl]amino]propan-2-yl)-2-cyanophenyl]-3,8-diazabicyclo[3.2.1]octane-8-carboxylate as a colorless oil (400 mg, 55%). LCMS (ESI, m/z): 505[M+H]$^+$.

Step 6. tert-Butyl 3-(4-(1-aminopropan-2-yl)-2-cyanophenyl)-3,8-diazabicyclo[3.2.1]octane-8-carboxylate Into a 100-mL round-bottom flask, purged and maintained under an atmosphere of nitrogen, was added tert-butyl 3-[4-(1-[[(benzyloxy)carbonyl]amino]propan-2-yl)-2-cyanophenyl]-3,8-diazabicyclo[3.2.1]octane-8-carboxylate (0.35 g, 0.69 mmol), tetrahydrofuran (15 mL), and 10% palladium on carbon (350 mg). The reaction mixture was sparged with hydrogen and was stirred for 1 h at RT under a hydrogen atmosphere (balloon pressure). The solids were removed by filtration over Celite and the filtrate was concentrated in vacuo. The crude product was purified via prep-TLC plate and eluted with dichloromethane/methanol (10:1) to afford tert-butyl 3-(4-(1-aminopropan-2-yl)-2-cyanophenyl)-3,8-diazabicyclo[3.2.1]octane-8-carboxylate as a brown oil (180 mg, 700%). LCMS (ESI, m/z): 371[M+H]$^+$.

Methods for the Synthesis of Compounds of Formula (I)

Example 15-1 (I-1): 7-Amino-3-methyl-N-(4-(piperazin-1-yl)phenethyl)thieno[2,3-b]pyrazine-6-carboxamide

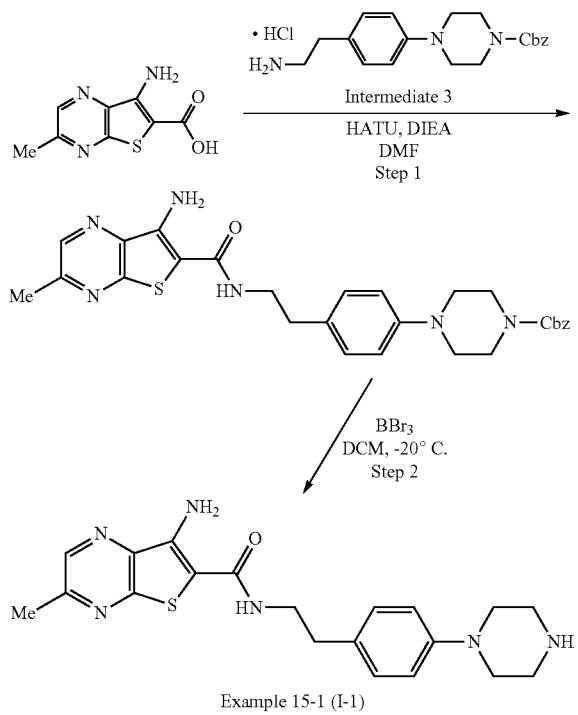

Example 15-1 (I-1)

Step 1. Benzyl 4-(4-(2-(7-amino-3-methylthieno[2,3-b]pyrazine-6-carboxamido)ethyl) phenyl)piperazine-1-carboxylate Into a 8-mL vial was added 7-amino-3-methylthieno[2,3-b]pyrazine-6-carboxylic acid (0.11 g, 0.53 mmol), benzyl 4-[4-(2-aminoethyl)phenyl]piperazine-1-carboxylate hydrochloride salt (0.259 g, 0.58 mmol), HATU (0.240 g, 0.63 mmol), DMF (5 mL), and DIEA (0.2 g, 0.3 mL, 1.72 mmol). The resulting solution was stirred overnight at RT. The solids were removed by filtration and the filtrate was purified by Prep-HPLC using the following conditions: (Waters 1) Column: XBridge C18, 19×150 mm, 5 μm; mobile phase, phase A: water (0.05% NH$_4$OH); phase B:CH$_3$CN (300% up to 85 in 7 min); Flow rate: 20 mL/min; Detector, 254 nm. This provided benzyl 4-(4-(2-(7-amino-3-methylthieno[2,3-b]pyrazine-6-carboxamido)ethyl)phenyl) piperazine-1-carboxylate (120 mg, 43%) as a yellow solid. LCMS (ESI, m/z): 531 [M+H]$^+$. $^1$H NMR (300 MHz, DMSO-d$_6$): δ ppm 8.64 (s, 1H), 7.93 (t, J=5.7 Hz, 1H), 7.41-7.30 (m, 5H), 7.29-7.08 (m, 2H), 6.91-6.88 (m, 4H), 5.10 (s, 2H), 3.53-3.50 (m, 4H), 3.42-3.31 (m, 2H), 3.09-3.06 (m, 4H), 2.76-2.71 (m, 2H), 2.64 (s, 3H).

Step 2. 7-Amino-3-methyl-N-(4-(piperazin-1-yl) phenethyl)thieno[2,3-b]pyrazine-6-carboxamide Into a 50-mL round-bottom flask was added benzyl 4-(4-(2-(7-amino-3-methylthieno[2,3-b]pyrazine-6-carboxamido)ethyl)phenyl)piperazine-1-carboxylate (0.050 g, 0.09 mmol), and dichloromethane (10 mL). The resulting solution was cooled to −20° C. then BBr$_3$ (1 M in DCM; 1 mL, 1 mmol) was added dropwise. The reaction mixture was stirred for 2 h at −20° C. and then quenched by the addition of methanol (10 mL). The resulting mixture was concentrated in vacuo, diluted with DMF (4 mL) and purified by Prep-HPLC using the following conditions: Column: XBridge C18, 19×150 mm, 5 μm; mobile phase; phase A: water (10 mm NH$_4$HCO$_3$+0.05% NH$_4$OH); phase B:CH$_3$CN (20% up to 70% in 8 min); Flow rate: 20 mL/min; Detector wavelength: 254 nm. This provided 7-amino-3-methyl-N-(4-(piperazin-1-yl)phenethyl) thieno[2,3-b]pyrazine-6-carboxamide (28 mg, 74%) as a yellow solid. LCMS (ESI, m/z): 391[M+H]$^+$. $^1$H NMR (300 MHz, DMSO-d$_6$): δ ppm 8.64 (s, 1H), 7.96-7.92 (m, 1H), 7.09-701 (m, 1H), 6.88-6.94 (m, 4H), 3.65-3.37 (m, 2H), 2.99-2.97 (m, 4H), 2.91-2.71 (m, 6H), 2.65 (s, 3H).

The Example in Table 6 below was synthesized according to the procedures outlined above for Example 15-1 (I-1), using the appropriate synthetic precursors. Additional details around the synthetic methods as well as HPLC purification conditions appear below the example.

TABLE 6

| Example (Cmpd No.) | Structure | MS (ESI, m/z) [M + H] | $^1$H NMR |
|---|---|---|---|
| 15-2 (I-2) | (structure shown) | 431 | (DMSO-d$_6$ 300 MHz): δ 8.64 (s, 1H), 7.98-7.95 (m, 1H), 7.28 (s, 1H), 7.17-7.04 (m, 2H), 6.89 (br s, 2H), 3.45-3.39 (m, 2H), 2.97-2.74 (m, 10H), 2.64 (s, 3H) |

Prep HPLC Purification Method: (Waters): Column: X Bridge C18, 19 × 150 mm, 5 μm; mobile phase, Mobile Phase A: Water (10 mM NH$_4$HCO$_3$ + 0.05% ammonia), Mobile Phase B: ACN; Flow rate: 20 mL/min; Gradient: 35% B to 40% B in 8 min; Detector wavelength: 254 nm Example 16-1 (I-3): N-(4-(3,8-diazabicyclo[3.2.1]octan-3-yl)-3-chlorophenethyl)-7-amino-3-methylthieno[2,3-b]pyrazine-6-carboxamide (hydrochloride salt)

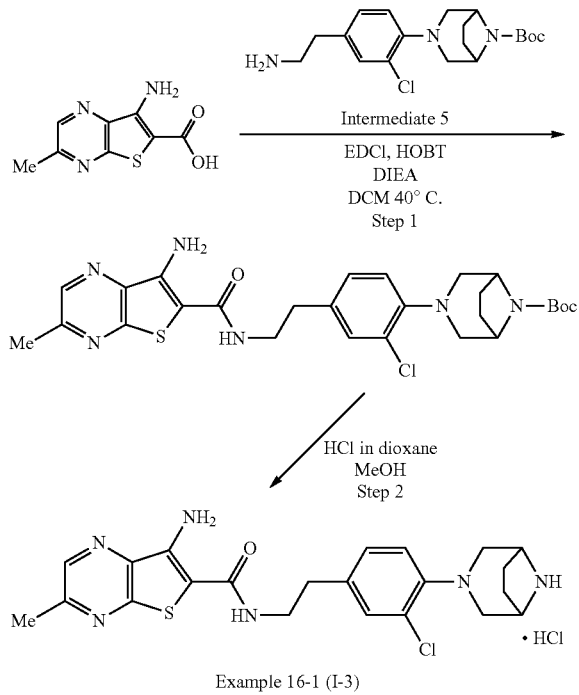

Example 16-1 (I-3)

Step 1. tert-Butyl 3-(4-(2-(7-amino-3-methylthieno[2,3-b]pyrazine-6-carboxamido)ethyl)-2-chlorophenyl)-3,8-diazabicyclo[3.2.1]octane-8-carboxylate Into a 25-mL round-bottom flask was added tert-butyl 3-[4-(2-aminoethyl)-2-chlorophenyl]-3,8-diazabicyclo[3.2.1]octane-8-carboxylate (0.100 g, 0.27 mmol), dichloromethane (5 mL), 7-amino-3-methylthieno[2,3-b]pyrazine-6-carboxylic acid (0.058 g, 0.28 mmol), EDCI (0.063 g, 0.33 mmol), HOBT (0.040 g, 0.30 mmol), and DIEA (0.106 g, 0.143 mL, 0.82 mmol). The resulting solution was stirred for 2 h at 40° C. in an oil bath. The reaction mixture was concentrated in vacuo and the crude product was dissolved in DMF (2 mL) and purified by Prep-HPLC using the following conditions: Column: SunFire Prep C18 5 μm 19×150 mm; mobile phase: water (containing 0.1% formic acid) and $CH_3CN$ ($CH_3CN$ 35% up to 65% in 6 min); Detector wavelength: 254 nm. This provided tert-butyl 3-(4-(2-(7-amino-3-methylthieno[2,3-b]pyrazine-6-carboxamido)ethyl)-2-chlorophenyl)-3,8-diazabicyclo[3.2.1]octane-8-carboxylate (50 mg, 33%) as a yellow solid. LCMS (ESI, m/z): 557[M+H]$^+$.

Step 2. N-(4-(3,8-diazabicyclo[3.2.1]octan-3-yl)-3-chlorophenethyl)-7-amino-3-methylthieno[2,3-b]pyrazine-6-carboxamide (hydrochloride salt)

Into a 25-mL round-bottom flask was added tert-butyl 3-(4-(2-(7-amino-3-methylthieno[2,3-b]pyrazine-6-carboxamido)ethyl)-2-chlorophenyl)-3,8-diazabicyclo[3.2.1]octane-8-carboxylate (0.040 g, 0.07 mmol), methanol (1 mL), and 4 N HCl/dioxane (2 mL). The resulting solution was stirred for 2 h at RT and then concentrated in vacuo. The solids were triturated with ether/MeOH (10:1; 10 mL) and collected by filtration to afford N-(4-(3,8-diazabicyclo[3.2.1]octan-3-yl)-3-chlorophenethyl)-7-amino-3-methylthieno[2,3-b]pyrazine-6-carboxamide (hydrochloride salt; 16.9 mg, 48%) as a yellow solid. LCMS (ESL m/z): 493 [M+H]$^+$. $^1$H NMR (300 MHz, MeOD): δ ppm 8.59 (s, 1H), 7.38 (s, 1H), 7.25-7.21 (m, 1H), 7.16-7.12 (m, 1H), 4.12 (br s, 2H), 3.68-3.52 (m, 2H), 3.33-3.29. (m, 2H), 3.19-3.15 (m 2H), 2.90-2.86 (m, 2H), 2.70 (s, 3H). 2.46-2.41 (m, 2H), 2.11-2.08 (m, 2H).

The Examples in Table 7 below were synthesized according to the procedures outlined above for Example 16-1 (I-3), using the appropriate synthetic precursors.

TABLE 7

| Example (Cmpd No.) | Structure | MS (ESI, m/z) [M + H] | $^1$H NMR |
|---|---|---|---|
| 16-2 (I-4)[1] | 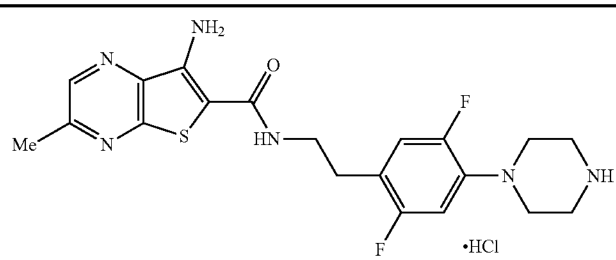 | 433 | (300 MHz, DMSO-$d_6$): δ ppm 9.28 (br s, 2H), 8.66 (s, 1H), 8.01 (t, J = 5.6 Hz, 1H), 7.15 (dd, J = 13.0, 7.0 Hz, 1H), 6.95 (dd, J = 11.4, 7.5 Hz, 1H), 3.54-3.32 (m, 2H), 3.19 (br s, 8H), 2.89-2.72 (m, 2H), 2.64 (s, 3H) |
| 16-3 (I-5)[2] | 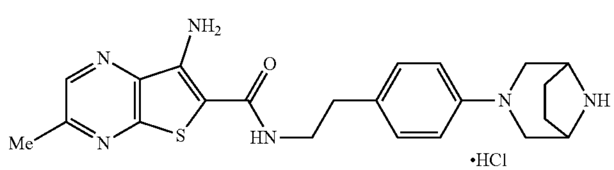 [SMILES: Cc1cnc2c(N)c(C(=O)NCCc3ccc(N4CC5CCC(C4)N5)cc3)sc2n1 ; Cl] | 459 | (300 MHz, DMSO-$d_6$): δ ppm 9.37 (br s, 2H), 8.67(s, 1H), 8.00-7.90 (m, 1H), 7.10 (d, J = 8.4 Hz, 2H), 6.84 (d, J = 8.7 Hz, 2H), 4.09 (br s, 2H), 3.58-3.50 (m, 2H), 3.41-3.30 (m, 2H), 3.10-3.00 (m, 2H), 2.76-2.64 (m, 2H), 2.63 (s, 3H). 1.98-1.90 (m, 4H) |

TABLE 7-continued

| Example (Cmpd No.) | Structure | MS (ESI, m/z) [M + H] | ¹H NMR |
|---|---|---|---|
| 16-4 (I-6)[3] | 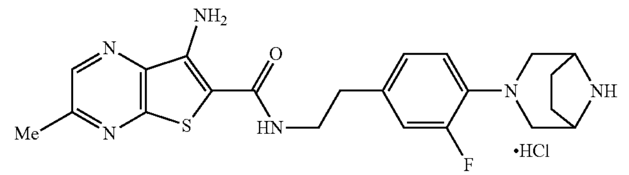 [SMILES: Cc1cnc2c(N)c(C(=O)NCCc3ccc(N4CC5CCC(C4)N5)c(F)c3)sc2n1 ; Cl] | 441 | (300 MHz, MeOD) δ ppm 8.59 (s, 1H), 7.16-6.92 (m, 3H), 4.14 (br s, 2H), 3.60-3.51 (m, 2H), 3.43-3.35 (m, 2H), 3.25-3.16 (m, 2H), 2.92-2.82 (m, 2H), 2.69 (s, 3H), 2.35-2.06 (m, 4H). |

[1]Isolation Conditions: The reaction mixture from Step 2 was concentrated in vacuo to afford a product that was triturated with diethyl ether. Filtration afforded the title compound as the HCl salt.
[2]Isolation Conditions: The reaction mixture from Step 2 was concentrated in vacuo to afford a product that was triturated with diethyl ether: MeOH (10:1). Filtration afforded the title compound as the HCl salt.
[3]Isolation Conditions: The reaction mixture from Step 2 was concentrated in vacuo to afford a product that was triturated with diethyl ether. Filtration afforded the title compound as the HCl salt.

Example 17-1 (I-7): N-(4-(3,8-diazabicyclo[3.2.1]octan-3-yl)-2,5-difluorophenethyl)-7-amino-3-methylthieno[2,3-b]pyrazine-6-carboxamide

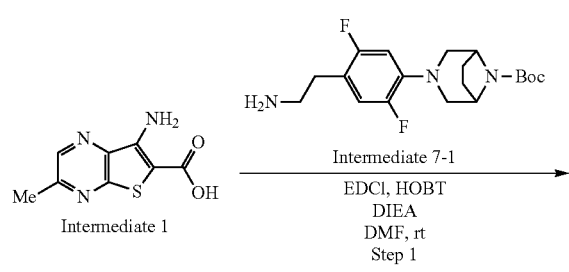

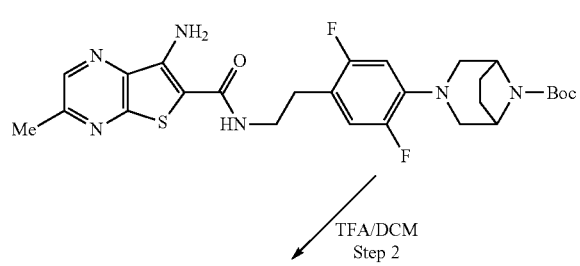

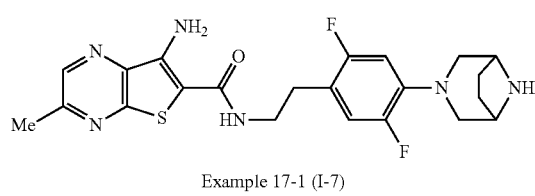

Example 17-1 (I-7)

Step 1. tert-Butyl 3-(4-(2-(7-amino-3-methylthieno[2,3-b]pyrazine-6-carboxamido)ethyl)-2,5-difluorophenyl)-3,8-diazabicyclo[3.2.1]octane-8-carboxylate Into a 500-mL round-bottom flask was added tert-butyl 3-[4-(2-aminoethyl)-2,5-difluorophenyl]-3,8-diazabicyclo[3.2.1]octane-8-carboxylate (3.00 g, 8.16 mmol), 7-amino-3-methylthieno[2,3-b]pyrazine-6-carboxylic acid (2.05 g, 9.80 mmol), EDCI (2.04 g, 10.64 mmol), HOBT (1.32 g, 9.77 mmol), DIEA (3.17 g, 4.27 mL, 24.5 mmol), and DMF (100 mL). The resulting solution was stirred for 1 h at 20° C. and then poured into water (500 mL). The resulting precipitate was collected by filtration and dried in vacuo to afford tert-butyl 3-(4-(2-(7-amino-3-methylthieno[2,3-b]pyrazine-6-carboxamido)ethyl)-2,5-difluorophenyl)-3,8-diazabicyclo[3.2.1]octane-8-carboxylate (2.4 g, 50%) as a yellow solid. LCMS (ESI, m/z): 559 [M+H]⁺.

Step 2. N-(4-(3,8-diazabicyclo[3.2.1]octan-3-yl)-2,5-difluorophenethyl)-7-amino-3-methylthieno[2,3-b]pyrazine-6-carboxamide Into a 100-mL round-bottom flask was added tert-butyl 3-(4-(2-(7-amino-3-methylthieno[2,3-b]pyrazine-6-carboxamido)ethyl)-2,5-difluorophenyl)-3,8-diazabicyclo[3.2.1]octane-8-carboxylate (2.80 g, 5.01 mmol), dichloromethane (50 mL), and trifluoroacetic acid (10 mL). The resulting solution was stirred for 1 h at 20° C. and then concentrated in vacuo. The crude product was slurried with a solution of ammonia in methanol (7 M; 50 mL). The solids were removed by filtration, and the filtrate was concentrated in vacuo to afford a crude product purified via Cis-reversed phase silica gel chromatography and eluted with acetonitrile and aqueous ammonium bicarbonate solution (10 mmol/L concentration of NH₄HCO₃) (from 0-60%). This provided N-(4-(3,8-diazabicyclo[3.2.1]octan-3-yl)-2,5-difluorophenethyl)-7-amino-3-methylthieno[2,3-b]pyrazine-6-carboxamide (1.5 g, 65%) as a yellow solid. LCMS (ESI, m/z): 459 [M+H]⁺. ¹H NMR (300 MHz, DMSO-d₆) δ ppm: 8.64 (s, 1H), 7.96-8.00 (m, 1H), 6.99-7.06 (m, 1H), 6.89 (s, 2H), 6.65-6.72 (m, 1H), 3.55-3.63 (m, 4H), 3.06-3.10 (m, 2H), 2.74-2.79 (m, 4H), 2.64 (s, 3H), 2.24 (br s, 1H), 1.74-1.81 (m, 2H), 1.64-1.71 (m, 2H).

The Examples in Table 8 below were synthesized according to the procedures outlined above for Example 17-1 (I-7), using the appropriate synthetic precursors. Additional details around the synthetic methods as well as HPLC purification conditions appear below the examples.

TABLE 8

| Example (Cmpd No.) | Structure | MS (ESI, m/z) [M + H] | ¹H NMR |
|---|---|---|---|
| 17-2 (I-23)[1] | 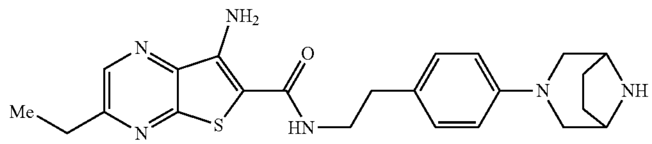 [SMILES: CCc1cnc2c(N)c(C(=O)NCCc3ccc(N4CC5CCC(C4)N5)cc3)sc2n1] | 437 | (400 MHz, CD$_3$OD) δ ppm 8.56 (s, 1H), 7.14-7.23 (m, 2H), 6.85-6.94 (m, 2H), 4.08-4.13 (m, 2H), 3.61-3.65 (m, 2H), 3.47-3.56 (m, 2H), 2.94-3.09 (m, 4H), 2.78-2.83 (m, 2H), 2.03-2.21 (m, 4H), 1.40 (t, J = 7.8 Hz, 3H) |
| 17-3 (I-9)[2] | 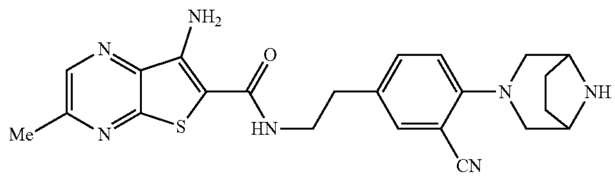 [SMILES: Cc1cnc2c(N)c(C(=O)NCCc3ccc(N4CC5CCC(C4)N5)c(C#N)c3)sc2n1] | 448 | (400 MHz, CD$_3$OD) δ ppm 8.56 (s, 1H), 7.41-7.53 (m, 2H), 7.05 (d, J = 8.5 Hz, 1H), 3.47-3.58 (m, 4H), 3.28-3.31 (m, 2H), 2.99 (d, J = 11.0 Hz, 2H), 2.86 (t, J = 7.3 Hz, 2H), 2.67 (s, 3H), 2.19-2.23 (m, 2H), 1.79-1.92 (m, 2H) |
| 17-4 (I-10)[3] | 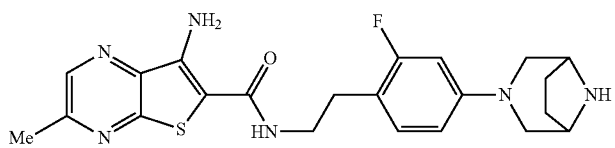 [SMILES: Cc1cnc2c(N)c(C(=O)NCCc3ccc(N4CC5CCC(C4)N5)cc3F)sc2n1] | 441 | (400 MHz, CD$_3$OD) δ ppm 8.54 (s, 1H), 7.08-7.12 (m, 1H), 6.52-6.59 (m, 2H), 3.62 (s, 2H), 3.45-3.52 (m, 2H), 3.41-3.44 (m, 2H), 2.82-2.87 (m, 4H), 2.67 (s, 3H), 1.85-1.94 (m, 4H) |
| 17-5 (I-11)[4] | 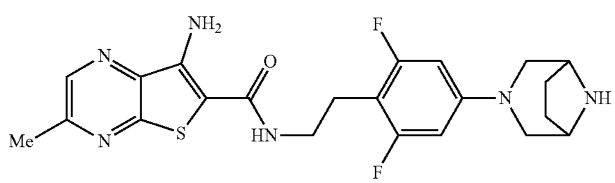 [SMILES: Cc1cnc2c(N)c(C(=O)NCCc3c(F)cc(N4CC5CCC(C4)N5)cc3F)sc2n1] | 459 | (400 MHz, CD$_3$OD): δ ppm 8.55 (s, 1H); 6.38-6.42 (m, 2H); 3.51-3.61 (m, 6H); 2.72-2.88 (m, 4H); 2.67 (s, 3H); 1.75-1.84 (m, 4H) |
| 17-6 (I-20)[5] | 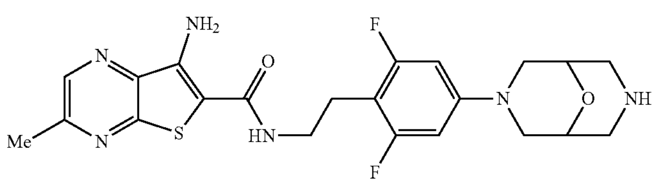 [SMILES: Cc1cnc2c(N)c(C(=O)NCCc3c(F)cc(N4CC5CNCC(C4)O5)cc3F)sc2n1] | 475 | (300 MHz, DMSO-d$_6$): δ ppm 8.65 (s, 1H), 8.00 (t, J = 5.7 Hz, 1H), 7.11-7.18 (m, 1H), 6.82-6.90 (m, 3H), 3.66 (s, 2H), 3.33-3.48 (m, 5H), 3.05-3.22 (m, 4H), 2.92-3.01 (m, 2H), 2.75-2.85 (m, 2H), 2.65 (s, 3H) |

[1]Prep HPLC Purification Conditions: Waters, LC parameters: Pump Mode: Binary gradient, Start Conc. of Pump B: 30.0%, End Conc. of Pump B: 35.0% Total Flow: 20 mL/min, Time: 8 min, Phase A: Water (10 mmol/L NH$_4$HCO$_3$), Phase B: MeCN-HPLC, Column Name: XBridge BEH C18 OBD Prep Column Length: 150 mm, Internal Diameter: 19 mm, Particle Size: 5 um, Aperture Size: 130 Å, Column Temp: 25° C., PDA Model: SPD-M20A, Wavelength: from 190 nm to 500 nm.

[2]Notes: Step 1 was conducted at 40° C. Prep HPLC Purification Conditions: SHIMADZU LC-20AD, LC parameters: Pump Mode: Binary gradient, Start Conc. of Pump B: 18.0%, End Conc. of Pump B: 30.0% Total Flow: 20 mL/min, Time: 8 min, Phase A: Water (10 mmol/L NH$_4$HCO$_3$), Phase B: MeCN-HPLC, Column Name: SunFire Prep C18 OBD Column Length: 150 mm, Internal Diameter: 19 mm, Particle Size: 5 um, Aperture Size: 130 Å, Column Temp: 25° C., PDA Model: SPD-M20A, Wavelength: from 190 nm to 500 nm

[3]Prep HPLC Purification Conditions: SHIMADZU LC-20AD, LC parameters: Pump Mode: Binary gradient, Start Conc. of Pump B: 30.0%, End Conc. of Pump B: 42.0% Total Flow: 20 mL/min, Time: 8 min, Phase A: Water (10 mmol/L NH$_4$HCO$_3$), Phase B: MeCN-HPLC, Column Name: XBridge Prep C18 OBD Column Length: 150 mm, Internal Diameter: 19 mm, Particle Size: 5 um, Aperture Size: 130 Å, Column Temp: 25° C., PDA Model: SPD-M20A, Wavelength: from 190 nm to 500 nm.

[4]Prep HLPLC Purification Conditions: SHIMADZU LC-20AD, LC parameters: Pump Mode: Binary gradient, Start Conc. of Pump B: 10.0%, End Conc. of Pump B: 55.0% Total Flow: 20 mL/min, Time: 8 min, Phase A: Water (10 mmol/L NH$_4$HCO$_3$), Phase B: MeCN-HPLC, Column Name: XBridge BEH C18 OBD Prep Column Length: 150 mm, Internal Diameter: 19 mm, Particle Size: 5 um, Aperture Size: 130 Å, Column Temp: 25° C., PDA Model: SPD-M20A, Wavelength: from 190 nm to 500 nm.

[5]Notes: Steps 1 and 2 were conducted at 30° C. Prep HPLC Purification Conditions: SHIMADZU LC-20AD, LC parameters: Pump Mode: Binary gradient, Start Conc. of Pump B: 25.0%, End Conc. of Pump B: 55.0% Total Flow: 20 mL/min, Time: 7 min, Phase A: Water (0.05% NH$_4$OH), Phase B: MeCN-HPLC, Column Name: SunFire Prep C18 OBD Prep Column, Length: 150 mm, Internal Diameter: 19 mm, Particle Size: 5 um, Aperture Size: 130 Å, Column Temp: 25° C., PDA Model: SPD-M20A, Wavelength: from 190 nm to 500 nm.

Examples 18-1A (I-12) and 18-1B (I-13): N-((2S)-2-(4-(3,8-diazabicyclo[3.2.1]octan-3-yl)-3-fluorophenyl)propyl)-7-amino-3-methylthieno[2,3-b]pyrazine-6-carboxamide (stereochemical configuration assumed) and N-((2R)-2-(4-(3,8-diazabicyclo[3.2.1]octan-3-yl)-3-fluorophenyl)propyl)-7-amino-3-methylthieno[2,3-b]pyrazine-6-carboxamide (stereochemical configuration assumed)

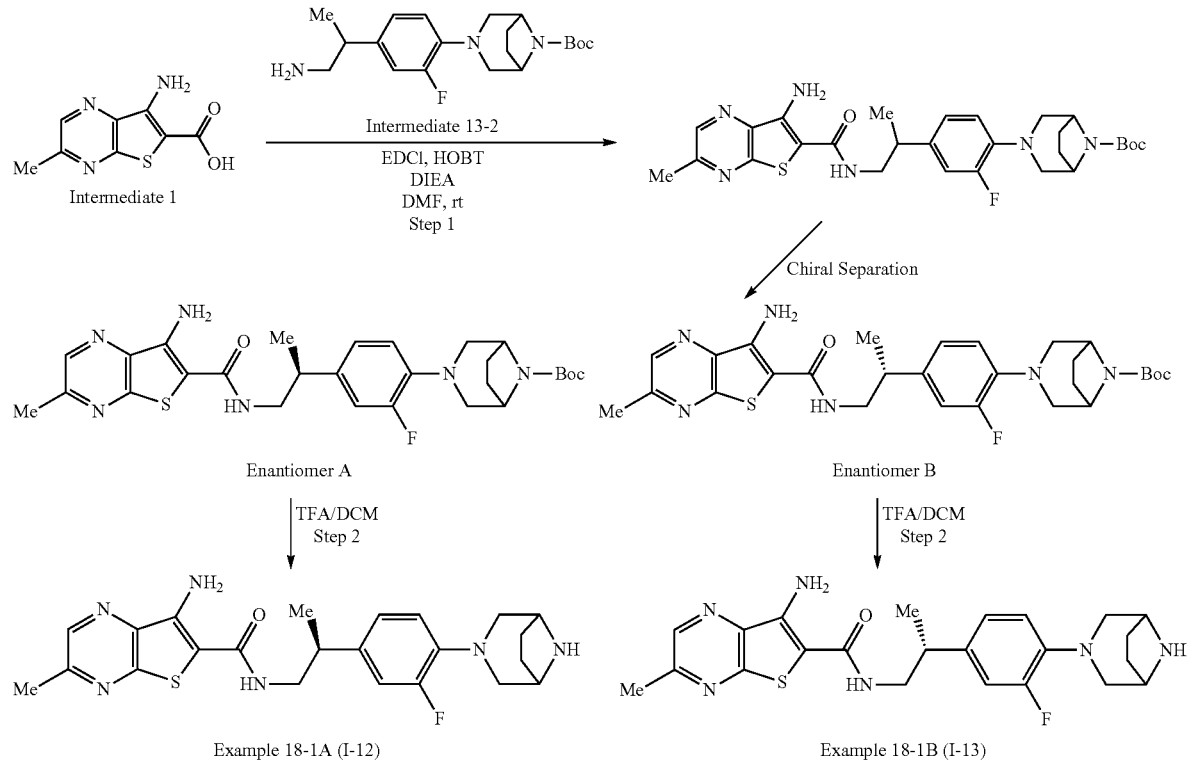

Step 1. tert-Butyl 3-(4-((S)-1-(7-amino-3-methylthieno[2,3-b]pyrazine-6-carboxamido)propan-2-yl)-2-fluorophenyl)-3,8-diazabicyclo[3.2.1]octane-8-carboxylate (stereochemical configuration assumed) and tert-butyl 3-(4-((R)-1-(7-amino-3-methylthieno[2,3-b]pyrazine-6-carboxamido)propan-2-yl)-2-fluorophenyl)-3,8-diazabicyclo[3.2.1]octane-8-carboxylate (stereochemical configuration assumed)

Into a 100-mL round-bottom flask was added tert-butyl 3-[4-(1-aminopropan-2-yl)-2-fluorophenyl]-3,8-diazabicyclo[3.2.1]octane-8-carboxylate (0.120 g, 0.33 mmol), 7-amino-3-methylthieno[2,3-b]pyrazine-6-carboxylic acid (0.069 g, 0.33 mmol), EDCI (0.082 g, 0.43 mmol), HOBt (0.053 g, 0.39 mmol), DIEA (0.085 g, 0.66 mmol), and DMF (5 mL). The resulting solution was stirred overnight at 20° C. and then quenched by the addition of water (10 mL). The resulting mixture was extracted with ethyl acetate (3×20 mL) and the combined organic layers were dried over anhydrous sodium sulfate, filtered, and concentrated in vacuo. The crude product was purified via silica gel column chromatography and eluted with ethyl acetate/petroleum ether (PE/EA=1:3). Chiral separation of the racemate was achieved by Chiral-Prep-HPLC using the following conditions: Instrument Name: SHIMADZU LC-20AD, LC parameters: Pump Mode: Binary gradient, Start Conc. of Pump B: 30.0%, Total Flow: 20 mL/min, Phase A: Hexane (0.1% DEA); Phase B: IPA-HPLC; Column Name: DAICEL CHIRALPAK IA, Length: 25 mm, Internal Diameter: 2 mm, Particle Size: 5 μm, Column Temp: 20° C., PDA Model: SPD-M20A, Wavelength: from 190 nm to 500 nm. This provided: Step 1, Enantiomer A: $1^{st}$ eluting peak (retention time=22.9 min, 27 mg (15%)) as a yellow solid. LCMS (ESI, m/z): 555 [M+H]$^+$; and Step 1, Enantiomer B: $2^{nd}$ eluting peak (retention time=24.9 min, 50 mg (27%)) as a yellow solid. LCMS (ESL m/z): 555 [M+H]$^+$.

Step 2. Example 18-1A (I-12): N-((2S)-2-(4-(3,8-diazabicyclo[3.2.1]octan-3-yl)-3-fluorophenyl)propyl)-7-amino-3-methylthieno[2,3-b]pyrazine-6-carboxamide (stereochemical configuration assumed)

Into a 25-mL round-bottom flask was added tert-butyl 3-(4-((S)-1-(7-amino-3-methylthieno[2,3-b]pyrazine-6-carboxamido)propan-2-yl)-2-fluorophenyl)-3,8-diazabicyclo[3.2.1]octane-8-carboxylate (Enantiomer A, stereochemical configuration assumed; 0.027 g, 0.05 mmol, 1.00 equiv), dichloromethane (2 mL), and trifluoroacetic acid (0.5 mL). The resulting solution was stirred for 30 min at 20° C. and was then concentrated in vacuo. The resulting crude product was dissolved in DCM (5 mL) and the pH of the solution was adjusted to approximately 8 with NH$_3$MeOH (7 M). The resulting mixture was concentrated in vacuo and the crude product was purified by Prep-HPLC using the following conditions: Instrument Name: SHIMADZU LC-20AD, LC parameters: Pump Mode: Binary gradient, Start Conc. of Pump B: 25.0%, End Conc. of Pump B: 42.0% Total Flow: 20 mL/min, Time: 8 min, Phase A: Water (10 mmol/L NH$_4$HCO$_3$), Phase B: MeCN-HPLC, Column Name: XBridge Prep C18 OBD Column Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm. This provided N-((2S)-2-(4-(3,8-diazabicyclo[3.2.1]octan-3-yl)-3-fluorophenyl)propyl)-7-amino-3-methylthieno[2,3-b]pyrazine-6-carboxamide (stereochemical configuration assumed, 12 mg, 53%) as a yellow solid. LCMS (ESI, m/z): 455 [M+H]$^+$. $^1$H NMR (400 MHz, CD$_3$OD): δ ppm 8.56 (s, 1H), 6.85-7.02 (m, 3H), 3.65 (s, 2H), 3.37-3.48 (m, 2H), 3.22 (d, J=11.2 Hz, 2H), 2.93-3.10 (m, 3H), 2.67 (s, 3H), 2.02-2.07 (m, 2H), 1.80-1.90 (m, 2H), 1.26 (d, J=6.8 Hz, 3H).

Step 2. Example 18-1B (I-13): N-((2R)-2-(4-(3,8-diazabicyclo[3.2.1]octan-3-yl)-3-fluorophenyl)propyl)-7-amino-3-methylthieno[2,3-b]pyrazine-6-carboxamide (stereochemical configuration assumed)

Example 18-1B (I-13) was prepared from Step 1, Enantiomer B according to the procedure outlined above for Example 18-1A (I-12). This afforded the title compound (10 mg, 25%) as a yellow solid. LCMS (ESI, m/z): 455 [M+H]$^+$. $^1$H NMR (400 MHz, CD$_3$OD) δ 8.56 (s, 1H), 6.85-7.02 (m, 3H), 3.63 (s, 2H), 3.37-3.48 (m, 2H), 3.17-3.25 (m, 2H), 3.01-3.05 (m, 1H), 2.96 (d, J=11.3 Hz, 2H), 2.67 (s, 3H), 1.98-2.06 (m, 2H), 1.82-1.88 (m, 2H), 1.26 (d, J=7.2 Hz, 3H).

The Examples in Table 9 below were synthesized according to the procedures outlined above for Examples 18-1A (I-12) and 18-1B (I-13), using the appropriate synthetic precursors. Additional detail around the synthetic methods as well as Chiral HPLC (after Step 1) and Prep HPLC purification conditions appear below each enantiomer pair.

TABLE 9

| Example (Cmpd No.) | Structure | MS (ESI, m/z) [M + H] | $^1$H NMR |
|---|---|---|---|
| 18-2A (I-14) | [structure] | 473 | (400 MHz, CD$_3$OD) δ ppm 8.57 (s, 1H), 7.06-7.10 (m, 1H), 6.71- 6.76 (m, 1H), 4.03 (br s, 2H), 3.45-3.54 (m, 2H), 3.36-3.40 (m, 3H), 3.09-3.12 (m, 2H), 2.66 (s, 3H), 2.18-2.23 (m, 2H), 2.03-2.14 (m, 2H), 1.28-1.31 (m, 3H) |
| 18-2B (I-15) | [structure] | 473 | (400 MHz, CD$_3$OD) δ ppm 8.55 (s, 1H), 7.06-7.10 (m, 1H), 6.67-6.71 (m, 1H), 4.03 (br s, 2H), 3.45-3.54 (m, 2H), 3.36-3.40 (m, 3H), 3.09-3.12 (m, 2H), 2.66 (s, 3H), 2.18-2.23 (m, 2H), 2.03-2.10 (m, 2H), 1.27 (d, J = 6.8 Hz, 3H) |

Chiral HPLC conditions for Step 1: SHIMADZU LC-20AD, LC parameters: Pump Mode: Binary gradient, Start Conc. of Pump B: 50.0%, Total Flow: 20 mL/min, Phase A: Hexane (0.1% DEA), Phase B: Ethanol, Column Name: (R,R)-WHELK-O1-Kromasil, Length: 250 mm, Internal Diameter: 5 cm. Particle Size: 5 μm, Column Temp: 20° C., PDA Model SPD-M20A, Wavelength: from 190 nm to 500 nm Step 1, Enantiomer A: 1$^{st}$ eluting peak (retention time = 10.3 min, 40 mg, 14%) as a white solid. LCMS (ES, m/z): 573 [M + H]$^+$.

Step 1, Enantiomer B: 2$^{nd}$ eluting peak (retention time = 14.5 min, 40 mg, 14%) as a white solid. LCMS (ESI, m/z): 573 [M + H]$^+$.

Prep HPLC Purification Method for Step 2: SHIMADZU LC-20AD, LC parameters: Pump Mode: Binary gradient, Start Conc. of Pump B: 25.0%, End Conc. of Pump B: 48.0% Total Flow: 20 mL/min, Time: 8 min, Phase A: Water (10 mmol/L NH$_4$HCO$_3$), Phase B: MeCN-HPLC, Column Name: XBridge Prep C18 OBD Column Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm.

TABLE 9-continued

| Example (Cmpd No.) | Structure | MS (ESI, m/z) [M + H] | ¹H NMR |
|---|---|---|---|
| 18-3A (I-16) | 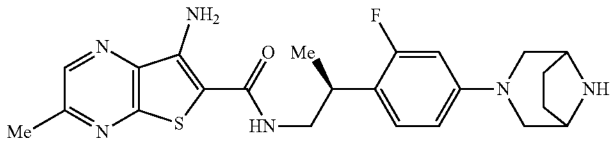 [SMILES: Cc1cnc2c(N)c(C(=O)NC[C@@H](C)c3ccc(N4CC5CCC(C4)N5)cc3F)sc2n1] | 455 | (300 MHz, CD₃OD) δ ppm 8.57 (s, 1H), 7.15-7.18 (m, 1H), 6.50-6.69 (m, 2H), 3.68-3.71 (m, 2H), 3.39-3.57 (m, 5H), 2.89 (d, J = 11.4 Hz, 2H), 2.68 (s, 3H), 1.78-1.90 (m, 4H), 1.23-1.35 (m, 3H) |
| 18-3B (I-17) | 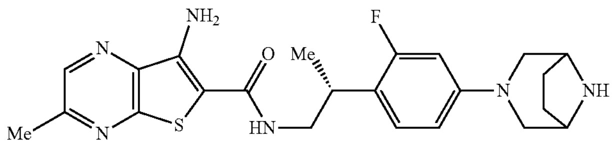 [SMILES: Cc1cnc2c(N)c(C(=O)NC[C@H](C)c3ccc(N4CC5CCC(C4)N5)cc3F)sc2n1] | 455 | (300 MHz, CD₃OD) δ ppm 8.56 (s, 1H), 7.12-7.18 (m, 1H), 6.50-6.69 (m, 2H), 3.68-3.71 (m, 2H), 3.39-3.57 (m, 5H), 2.87 (d, J = 11.4 Hz, 2H), 2.67 (s, 3H), 1.78-1.90 (m, 4H), 1.28 (t, J = 7.2 Hz, 3H) |

Chiral HPLC conditions for Step 1: SHIMADZU LC-20AD, LC parameters: Pump Mode: Binary gradient, Start Conc. of Pump B: 50.0%, Total Flow: 16 mL/min, Phase A: Hexane (0.1% DEA), Phase B: EtOH-HLCP, Column Name: DAICEL CHIRALPAK IA, Length: 250 mm, Internal Diameter: 20 mm, Particle Size: 5 um, Column Temp: 20° C., PDA Model SPD-M20A, Wavelength: from 190 nm to 500 nm.
Step 1, Enantiomer A: 1ˢᵗ eluting peak (retention time = 12.5 min, 30 mg, 33%) as a white solid. LCMS (ES, m/z): 555 [M + H]⁺.
Step 1, Enantiomer B: 2ⁿᵈ eluting peak (retention time = 15.5 min, 50 mg, 56%) as a white solid. LCMS (ES, m/z): 555 [M + H]⁺.
Prep HPLC Purification Method for Step 2: SHIMADZU LC-20AD, LC parameters: Pump Mode: Binary gradient, Start Conc. of Pump B: 25.0%, End Conc. of Pump B: 75.0% Total Flow: 30 mL/min, Time: 7 min, Phase A: Water (10 mmol/L NH₄HCO₃), Phase B: MeCN-HPLC, Column Name: XBridge Prep C18 OBD Column Length: 150 mm, Internal Diameter: 19 mm, Particle Size: 5 um, Aperture Size: 130 Å, Column Temp: 25° C., PDA Model: SPD-M20A, Wavelength: from 190 nm to 500 nm.

| Example (Cmpd No.) | Structure | MS (ESI, m/z) [M + H] | ¹H NMR |
|---|---|---|---|
| 18-4A (I-18) | 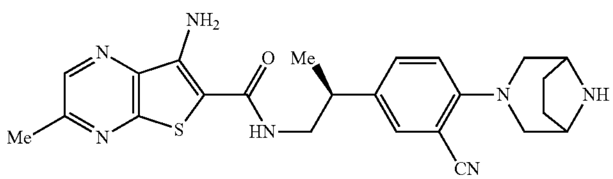 [SMILES: Cc1cnc2c(N)c(C(=O)NC[C@@H](C)c3ccc(N4CC5CCC(C4)N5)c(C#N)c3)sc2n1] | 462 | (400 MHz, CD₃OD) δ ppm 8.56 (s, 1H), 7.42-7.54 (m, 2H), 6.97-7.05 (m, 1H), 3.50-3.54 (m, 2H), 3.38-3.49 (m, 2H), 3.29-3.32 (m, 2H), 3.05-3.13 (m, 1H), 2.99 (d, J = 11.2 Hz, 2H), 2.67 (s, 3H), 2.09-2.28 (m, 2H), 1.78-1.86 (m, 2H), 1.28 (t, J = 6.8 Hz, 3H) |
| 18-4B (I-18) | 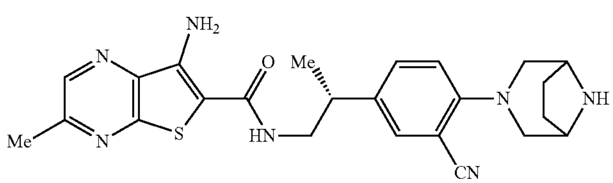 [SMILES: Cc1cnc2c(N)c(C(=O)NC[C@H](C)c3ccc(N4CC5CCC(C4)N5)c(C#N)c3)sc2n1] | 462 | (400 MHz, CD3OD) δ ppm 8.55 (s, 1H), 7.42-7.54 (m, 2H), 7.05 (d, J = 8.4 Hz, 1H), 3.50-3.54 (m, 2H), 3.38-3.49 (m, 2H), 3.29-3.32 (m, 2H), 3.05-3.13 (m, 1H), 2.95-2.99 (m, 2H), 2.66 (s, 3H), 2.09-2.28 (m, 2H). 1.78-1.86 (m, 2H), 1.28 (t, J = 7.2 Hz, 3H) |

Notes: Step 1 was conducted at 40° C. Chiral HPLC conditions for Step 1: SHIMADZU LC-20AD, LC parameters: Pump Mode: Binary gradient, Start Conc. of Pump B: 50.0%, Total Flow: 20 mL/min, Phase A: Hexane-HPLC, Phase B: IPA-HPLC, Column Name: Column: Repaired DAICEL CHIRAL IA, Length: 250 mm, Internal Diameter: 21.2 mm, Particle Size: 5 um, Column Temp: 20° C., PDA Model SPD-M20A, Wavelength: from 190 nm to 500 nm.
Step 1, Enantiomer A: 1ˢᵗ eluting peak (retention time = 15.4 min, 30 mg, 25%) as a white solid. LCMS (ES, m/z): 562 [M + H]⁺. Step 1, Enantiomer B: 2ⁿᵈ eluting peak (retention time = 18.3 min, 30 mg, 25%) as a white solid. LCMS (ES, m/z): 562 [M + H]⁺.
Prep HPLC Purification Method for Step 2: SHIMADZU LC-20AD, LC parameters: Pump Mode: Binary gradient, Start Conc. of Pump B: 22.0%, End Conc. of Pump B: 37.0% Total Flow: 20 mL/min, Time: 7 min, Phase A: Water (10 mmol/L NH₄HCO₃), Phase B: MeCN-HPLC, Column Name: XBridge Prep C18 OBD Column Length: 150 mm, Internal Diameter: 19 mm, Particle Size: 5 um, Aperture Size: 130 Å, Column Temp: 25° C., PDA Model: SPD-M20A, Wavelength: from 190 nm to 500 nm.

TABLE 9-continued

| Example (Cmpd No.) | Structure | MS (ESI, m/z) [M + H] | $^1$H NMR |
|---|---|---|---|
| 18-5A (I-21) | (structure) | 489 | (400 MHz, DMSO-$d_6$) δ ppm 8.63 (s, 1H), 7.95 (t, J = 7.6 Hz, 1H), 7.17-7.22 (m, 1H), 6.87 (s, 2H), 6.79-6.84 (m, 1H), 3.66 (s, 2H), 3.33-3.48 (m, 6H), 3.05-3.22 (m, 4H), 2.92-3.01 (m, 2H), 2.75-2.85 (m, 2H), 2.65 (s, 3H), 1.18 (d, J = 6.0 Hz, 3H) |
| 18-5B (I-22) | (structure) | 489 | (400 MHz, DMSO-$d_6$): δ ppm 8.65 (s, 1H), 7.95 (t, J = 5.6 Hz, 1H), 7.17-7.22 (m, 1H), 6.88 (s, 2H), 6.79-6.84 (m, 1H), 3.66 (s, 2H), 3.33-3.48 (m, 6H), 3.05-3.22 (m, 4H), 2.92-3.01 (m, 2H), 2.65 (s, 3H), 1.18 (d, J = 6.4 Hz, 3H) |

Chiral HPLC conditions for Step 1: SHIMADZU LC-20AD, LC parameters: Pump Mode: Binary gradient, Start Conc. of Pump B: 35.0%, Total Flow: 20 mL/min, Phase A: Hexane:DCM = 3:1, Phase B: IPA-HPLC, Column Name: Chiralpak ID-2, Length: 25 mm, Internal Diameter: 2 mm, Particle Size: 5 um, Column Temp: 20° C., PDA Model SPD-M20A, Wavelength: from 190 nm to 500 nm.
Step 1, Enantiomer A: $1^{st}$ eluting peak (retention time = 13.1 min, 20 mg, 24%) as a light yellow solid. LCMS (ES, m/z): 589 [M + H]$^+$.
Step 1, Enantiomer B: $2^{nd}$ eluting peak (retention time = 16.7 min, 21 mg, 25%) as a light yellow solid. LCMS (ES, m/z): 589 [M + H]$^+$.
Prep HPLC Purification Method for Step 2: Instrument Name: SHIMADZU LC-20AD, LC parameters: Pump Mode: Binary gradient, Start Conc. of Pump B: 20.0%, End Conc. of Pump B: 55.0% Total Flow: 20 mL/min, Time: 8 min, Phase A: Water (0.05% NH$_4$OH), Phase B: MeCN-HPLC, Column Name: Sunfire Prep C18 OBD Column Length: 150 mm, Internal Diameter: 19 mm, Particle Size: 5 um, Aperture Size: 130 Å, Column Temp: 25 °C., PDA Model: SPD-M20A, Wavelength: from 190 nm to 500 nm.

Example 19: Biochemical Assay: Ubiquitin-Rhodamine 110 Assay for USP28 Activity Each assay was performed in a final volume of 20 μL in assay buffer containing 20 mM Tris-HCl (pH 8.0, (1M Tris-HCl, pH 8.0 solution; Corning 46-031-CM)), 2 mM CaCl$_2$) (1M Calcium Chloride solution; Sigma #21114) 2 mM BME (2-Mercaptoethanol; Sigma 63689-25ML-F), 0.01% Prionex (0.22 μM filtered, Sigma # G-0411), and 0.01% Triton X-100. Stock compound solutions were stored at −20° C. as 10 mM in DMSO. Up to 1 month prior to the assay, 2 mM test compounds were pre-dispensed into assay plates (Black, low volume; Corning #3820) and frozen at −20° C. Prestamped assay plates were allowed to come to room temperature on the day of the assay. For the screen, 100 nL of 2 mM was pre-dispensed for a final screening concentration of 10 μM (DMSO$_{(fc)}$=0.5%). Enzyme (USP28, construct USP28 (USP28-5(1-1077)-TEV-6*His; LifeSensors) concentration and incubation times were optimized for the maximal signal-to-background while maintaining initial velocity conditions at a fixed substrate concentration. The final concentration of the enzyme in the assay was 400 pM. Final substrate (Ub-Rh110; Ubiquitin-Rhodamine 110, R&D Systems # U-555) concentration was 25 nM with [Ub-Rh110]<<Km. 10 μL of 2× enzyme was added to assay plates (pre-stamped with compound) either simultaneously with 2×Ub-Rh110 or preincubated with USP28 40 minutes prior to the addition of 10 μL of 2×Ub-Rh110 to compound plates. Plates were incubated stacked for 90 minutes at room temperature before fluorescence was read on the Envision (Excitation at 485 nm and Emission at 535 nm; Perkin Elmer) or on the PheraSTAR (Excitation at 485 nm and Emission at 535 nm; BMG Labtech).

For follow-up studies, Each assay was performed in a final volume of 15 μL in assay buffer containing 20 mM Tris-HCl (pH 8.0, (1M Tris-HCl, pH 8.0 solution; Corning 46-031-CM)), 3 mM BME (2-Mercaptoethanol; Sigma 63689-25ML-F), 0.03% BGG (0.22 μM filtered, Sigma, G7516-25G), and 0.01% Triton X-100 (Sigma, T9284-10L). Nanoliter quantities of either an 8-point or 10-point, 3-fold serial dilution in DMSO was pre-dispensed into assay plates (Perkin Elmer, ProxiPlate-384 F Plus, #) for a final test concentration of either 25 μM to 11 nM or 25 μM to 1.3 nM, respectively. Enzyme USP28, construct USP28 (USP28-5 (1-1077)-TEV-6*His; LifeSensors) concentration and incubation times were optimized for the maximal signal-to-background while maintaining initial velocity conditions at a fixed substrate concentration. The final concentration of the enzyme in the assay was 75 pM. Final substrate (Ub-Rh110; Ubiquitin Rhodamine 110, R&D Systems # U-555) concentration was 25 nM with [Ub-Rh110]<<Km. 5 μL of 2× enzyme was added to assay plates (pre-stamped with compound) preincubated with USP28 for 30 minutes and then 5 μL of 2×Ub-Rh110 was added to assay plates. Plates were incubated stacked for 20 minutes at room temperature before 5 μL of stop solution was added (final concentration of 10 mM citric acid (Sigma, 251275-500G)). Fluorescence was read on the Envision (Excitation at 485 nm and Emission at 535 nm; Perkin Elmer) or on the PheraSTAR (Excitation at 485 nm and Emission at 535 nm; BMG Labtech).

Example 20: Biochemical Assay: Ubiquitin-Rhodamine 110 Assay for USP25 Activity The assay was performed in a final volume of 9 μL in assay buffer containing 20 mM Tris-HCl (pH 8.0, (1M Tris-HCl, pH 8.0 solution; Corning 46-031-CM)), 3 mM BME (2-Mercaptoethanol; Sigma 63689-25ML-F), 0.03% BGG (0.22 μM filtered, Sigma, G7516-25G), and 0.01%

Triton X-100 (Sigma, T9284-10L). Nanoliter quantities of 10-point, 3-fold serial dilution in DMSO was pre-dispensed into 1536 assay plates (Corning, #3724BC) for a final test concentration of 25 μM to 1.3 nM, top to lowest dose, respectively. Enzyme USP25, construct USP25-His6, (Boston Biochem E-546). Concentration and incubation times were optimized for the maximal signal-to-background while maintaining initial velocity conditions at a fixed substrate concentration. The final concentration of the enzyme in the assay was 75 pM. Final substrate (Ub-Rh110 Ubiquitin-Rhodamine 110, R&D Systems # U-555) concentration was 25 nM with [Ub-Rh110]<<Km. 3 μL of 2× enzyme was added to assay plates (pre-stamped with compound) preincubated with USP25 for 30 minutes and then 3 μL of 2×Ub-Rh110 was added to assay plates. Plates were incubated for 45 minutes at room temperature before addition of 3 μL of stop solution (final concentration of 10 mM citric acid (Sigma, 251275-500G)). Fluorescence was read on the Envision (Excitation at 485 nm and Emission at 535 nm; Perkin Elmer) or on the PheraSTAR (Excitation at 485 nm and Emission at 535 nm; BMG Labtech).

For both the USP28 and USP25 assay formats Data were reported as percent inhibition compared with control wells based on the following equation: % inh=1−((FLU−Ave$_{Low}$)/(Ave$_{High}$−Ave$_{Low}$)) where FLU=measured Fluorescence, Ave$_{Low}$=average Fluorescence of no enzyme control (n=16), and Ave$_{High}$=average Fluorescence of DMSO control (n=16). IC$_{50}$ values were determined by curve fitting of the standard 4 parameter logistic fitting algorithm included in the Activity Base software package: IDBS XE Designer Model205. Data is fitted using the Levenburg Marquardt algorithm.

Table 10: USP28 and USP25 activities of compounds of the disclosure in USP28 and USP25 assays. ++++ indicates an IC$_{50}$ of less than about 0.2 μM, +++ indicates an IC$_{50}$ between about 0.2 μM and about 2 μM, ++ indicates an IC$_{50}$ between about 2 μM and about 10 μM, and + indicates an IC$_{50}$ between about 10 μM and about 25 μM. ND indicates that the data has not been determined.

TABLE 10

USP28 and USP25 Assays

| Compound No. | USP28 IC$_{50}$ | USP25 IC$_{50}$ |
|---|---|---|
| I-1 | +++ | ND |
| I-2 | +++ | ND |
| I-3 | ++++ | ND |
| I-4 | +++ | ++ |
| I-5 | ++++ | ND |
| I-6 | ++++ | ++++ |
| I-7 | ++++ | +++ |
| I-9 | +++ | +++ |
| I-10 | ++++ | +++ |
| I-11 | +++ | +++ |
| I-12 | +++ | ++ |
| I-13 | +++ | ++ |
| I-14 | ++ | ND |
| I-15 | ++++ | ++ |
| I-16 | +++ | +++ |
| I-17 | +++ | ++ |
| I-18 | ++ | ++ |
| I-19 | ++ | ++ |
| I-20 | ++++ | ++++ |
| I-21 | +++ | +++ |
| I-22 | +++ | +++ |
| I-23 | ++ | +++ |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound of Formula (I):

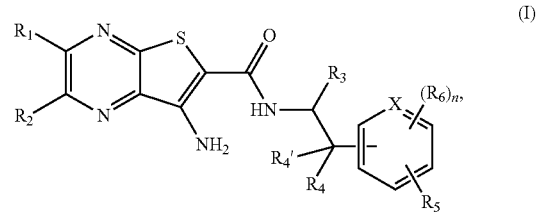

or a pharmaceutically acceptable salt, stereoisomer, or tautomer thereof,
wherein:
X is N or CR$_6$;
R$_1$ is H, (C$_1$-C$_6$) alkyl, (C$_1$-C$_6$) alkoxy, (C$_1$-C$_6$) haloalkyl, (C$_1$-C$_6$) haloalkoxy, (C$_1$-C$_6$) hydroxyalkyl, halogen, (C$_3$-C$_8$) cycloalkyl, —CN, or —NR$_8$R$_9$;
R$_2$ is H, (C$_1$-C$_6$) alkyl, (C$_1$-C$_6$) alkoxy, (C$_1$-C$_6$) haloalkyl, (C$_1$-C$_6$) haloalkoxy, (C$_1$-C$_6$) hydroxyalkyl, halogen, (C$_3$-C$_8$) cycloalkyl, or —NR$_{10}$R$_{11}$;
or R$_1$ and R$_2$ together form a (C$_4$-C$_8$) cycloalkyl optionally substituted with one or more R$_{12}$;
R$_3$ is H, (C$_1$-C$_6$) alkyl, or (C$_1$-C$_6$) haloalkyl;
R$_4$ is H, (C$_1$-C$_6$) alkyl, halogen, or (C$_1$-C$_6$) haloalkyl;
R$_4$' is H, (C$_1$-C$_6$) alkyl, halogen, or (C$_1$-C$_6$) haloalkyl;
R$_5$ is —(C$_0$-C$_3$) alkylene-C(O)OH, —(C$_0$-C$_3$) alkylene-(3-9 member heterocyclyl), —O-(3-9 member heterocyclyl), —(C$_0$-C$_3$) alkylene-aryl, —(C$_0$-C$_3$) alkylene-(5-24 member heteroaryl) or —N(R$_7$)-(C$_0$-C$_3$) alkylene-(3-9 member heterocyclyl), wherein the heterocyclyl, aryl and heteroaryl are optionally substituted with one or more R$_{13}$;
each R$_6$ is independently at each occurrence H, (C$_1$-C$_6$) alkyl, (C$_1$-C$_6$) alkoxy, (C$_1$-C$_6$) haloalkyl, (C$_1$-C$_6$) haloalkoxy, halogen, —OH, —CN, (C$_3$-C$_8$) cycloalkyl, 3-9 member heterocyclyl, aryl, or 5-24 member heteroaryl, wherein the alkyl is optionally substituted with one or more (C$_1$-C$_6$) alkoxy or —OH, and wherein the cycloalkyl, 3-9 member heterocyclyl, aryl, and heteroaryl are optionally substituted with one or more R$_{14}$; or
R$_5$ and R$_6$ together when on adjacent atoms form a (C$_4$-C$_8$) cycloalkyl ring optionally substituted with one or more R$_{15}$; or R$_5$ and R$_6$ together when on adjacent atoms form a heterocyclyl ring optionally substituted with one or more R$_{15}$; R$_5$ and R$_6$ together when on adjacent atoms form an aryl ring optionally substituted with one or more R$_{15}$; or R$_5$ and R$_6$ together when on adjacent atoms form a heteroaryl ring optionally substituted with one or more R$_{15}$; or
two R$_6$ together when on adjacent atoms form a (C$_4$-C$_8$) cycloalkyl ring; or two R$_6$ together when on adjacent atoms form a heterocyclyl ring; two R$_6$ together when on adjacent atoms form an aryl ring; or two R$_6$ together when on adjacent atoms form a heteroaryl ring;

$R_7$ is H or $(C_1-C_6)$ alkyl;

each $R_8$, $R_9$, $R_{10}$, and $R_{11}$ is independently H, $(C_1-C_6)$ alkyl, or —C(O)($C_1-C_6$) alkyl;

each $R_{12}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, or —OH;

each $R_{13}$ is independently at each occurrence $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, —C(O)$NR_{18}R_{19}$, —S(O)$_2$($C_1-C_6$) alkyl, —OH, or —$NR_{16}R_{17}$, wherein the alkyl is optionally substituted with one or more substituents independently selected from $(C_1-C_6)$ alkoxy, OH, and 3-9 member heterocyclyl; or two $R_{13}$ together when attached to the same carbon can form —C=(O) when $R_5$ is —$(C_0-C_3)$ alkylene-(3-9 member heterocyclyl), —O-(3-9 member heterocyclyl), or —N($R_7$)-($C_0-C_3$) alkylene-(3-9 member heterocyclyl); or two $R_{13}$ together when attached to the same atom form a $(C_3-C_8)$ spirocycloalkyl optionally substituted with one or more $R_{20}$ when $R_5$ is —$(C_0-C_3)$ alkylene-(3-9 member heterocyclyl), —O-(3-9 member heterocyclyl), or —N($R_7$)-($C_0-C_3$) alkylene-(3-9 member heterocyclyl); or two $R_{13}$ together when attached to the same atom form a $(C_3-C_8)$ spiroheterocyclyl optionally substituted with one or more $R_{20}$ when $R_5$ is —$(C_0-C_3)$ alkylene-(3-9 member heterocyclyl), —O-(3-9 member heterocyclyl), or —N($R_7$)-($C_0-C_3$) alkylene-(3-9 member heterocyclyl); or two $R_{13}$ together when on adjacent atoms form a heterocyclyl ring optionally substituted with one or more $R_{20}$; or two $R_{13}$ together when on adjacent atoms form a heteroaryl ring optionally substituted with one or more $R_{20}$; or two $R_{13}$ together with the atoms to which they are attached can form a bridged heterocyclyl ring optionally substituted with one or more $R_{20}$ when $R_5$ is —$(C_0-C_3)$ alkylene-(3-9 member heterocyclyl), —O-(3-9 member heterocyclyl), or —N($R_7$)—($C_0$—$C_3$) alkylene-(3-9 member heterocyclyl);

each $R_{14}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, cycloalkyl, 3-9 member heterocyclyl, or —C(O)-(3-9 member heterocyclyl), wherein the alkyl is optionally substituted with one or more substituents independently selected from $(C_1-C_6)$ alkoxy and —OH;

each $R_{15}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —OH, —CN, —C(O)OH, or —C(O)O($C_1-C_6$) alkyl;

each $R_{16}$ and $R_{17}$ is independently H, $(C_1-C_6)$ alkyl, $(C_3-C_8)$ cycloalkyl, —$CH_2C(O)NH_2$, —S(O)$_2$($C_1-C_6$) alkyl, —S(O)$_2$($C_6-C_{10}$) aryl or —C(O)($C_1-C_6$) alkyl;

each $R_{18}$ and $R_{19}$ is independently H or $(C_1-C_6)$ alkyl;

each $R_{20}$ is independently at each occurrence $(C_1-C_6)$ alkyl, $(C_1-C_6)$ alkoxy, $(C_1-C_6)$ haloalkyl, $(C_1-C_6)$ haloalkoxy, or halogen; or two $R_{20}$ together when attached to the same carbon form —C=(O); and n is 0, 1, 2, or 3.

2. The compound of claim 1, wherein $R_1$ is $(C_1-C_6)$ alkyl and $R_2$ is H.

3. The compound of claim 1, having the structure of Formula (Ig):

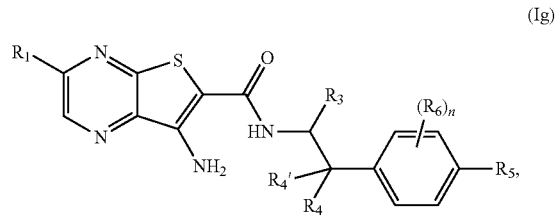

or a pharmaceutically acceptable salt, stereoisomer, or tautomer thereof.

4. The compound of claim 1, wherein $R_3$, $R_4$, and $R_4'$ are each independently chosen from H or $(C_1-C_6)$ alkyl.

5. The compound of claim 1, wherein $R_5$ is —$(C_0-C_3)$ alkylene-(3-9 member heterocyclyl) wherein the heterocyclyl is optionally substituted with one or more $R_{13}$.

6. The compound of claim 1, wherein $R_6$ is halogen or H.

7. The compound of claim 6, wherein $R_6$ is halogen and n=2.

8. The compound of claim 3, wherein $R_1$ is $(C_1-C_6)$ alkyl; $R_2$ is H; $R_3$ and $R_4$ are each independently chosen from H or $(C_1-C_6)$ alkyl; $R_5$ is —$(C_0)$ alkylene-(3-9 member heterocyclyl); $R_6$ is halogen and n=2.

9. The compound of claim 1, wherein X is CH.

10. The compound of claim 1, wherein $R_3$ is H or CH3.

11. The compound of claim 8, wherein $R_4$ is H or CH3 and $R_4'$ is H.

12. The compound of claim 1, wherein X is CH; $R_3$ is H or $CH_3$; $R_4$ is H or $CH_3$; and $R_4'$ is H.

13. The compound of claim 3, wherein $R_1$ is $(C_1-C_6)$ alkyl; $R_2$ is H; $R_3$ and $R_4$ are each independently chosen from H or $(C_1-C_6)$ alkyl; $R_5$ is —$(C_0)$ alkylene-(3-9 member heterocyclyl) with the heterocyclyl being substituted with two $R_{13}$, wherein the two $R_{13}$ together with the atoms to which they are attached form a bridged heterocyclyl ring; $R_6$ is halogen; and n=2.

14. The compound of claim 1, selected from:

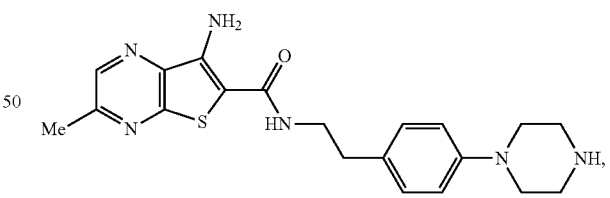

7-amino-3-methyl-N-(4-(piperazin-1-yl)phenethyl)thieno[2,3-b]pyrazine-6-carboxamide

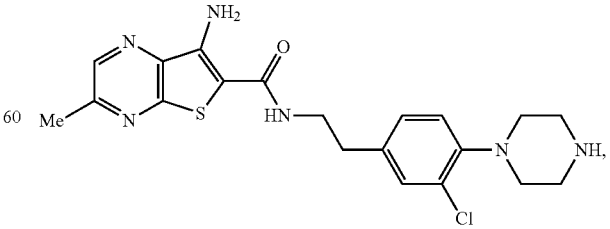

7-amino-N-(3-chloro-4-(piperazin-1-yl)phenethyl)-3-methylthieno[2,3-b]pyrazine-6-carboxamide -continued

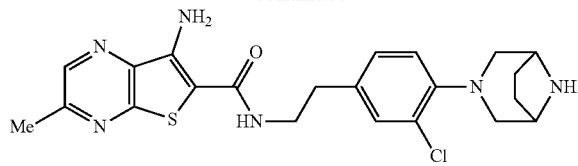

N-(4-(3,8-diazabicyclo[3.2.1]octan-3-yl-3-chlorophenethyl-7-amino-
3-methylthieno[2,3-b]pyrazine-6-carboxamide

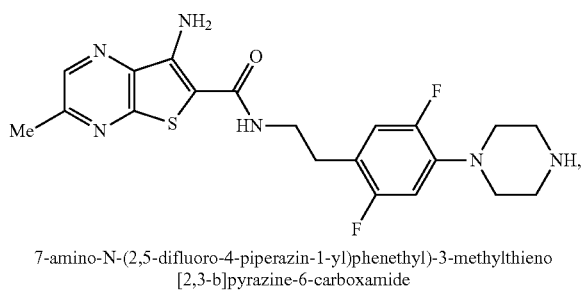

7-amino-N-(2,5-difluoro-4-piperazin-1-yl)phenethyl)-3-methylthieno
[2,3-b]pyrazine-6-carboxamide

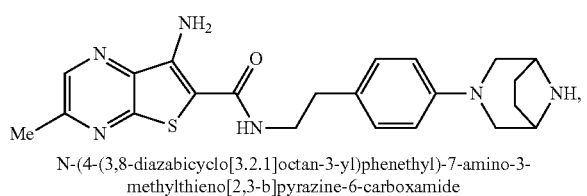

N-(4-(3,8-diazabicyclo[3.2.1]octan-3-yl)phenethyl)-7-amino-3-
methylthieno[2,3-b]pyrazine-6-carboxamide

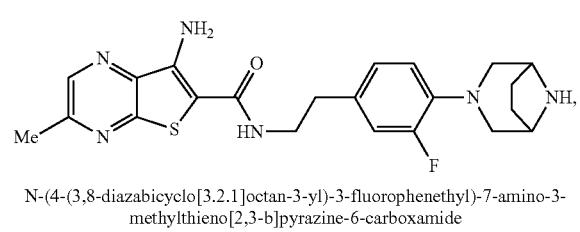

N-(4-(3,8-diazabicyclo[3.2.1]octan-3-yl)-3-fluorophenethyl)-7-amino-3-
methylthieno[2,3-b]pyrazine-6-carboxamide

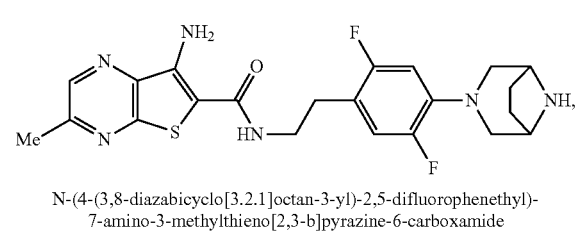

N-(4-(3,8-diazabicyclo[3.2.1]octan-3-yl)-2,5-difluorophenethyl)-
7-amino-3-methylthieno[2,3-b]pyrazine-6-carboxamide

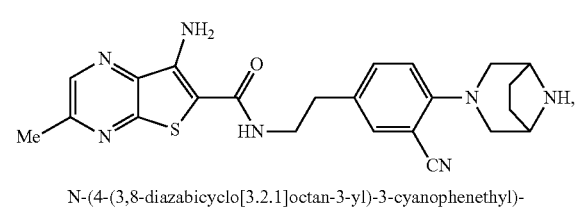

N-(4-(3,8-diazabicyclo[3.2.1]octan-3-yl)-3-cyanophenethyl)-
7-amino-3-methylthieno[2,3-b]pyrazine-6-carboxamide

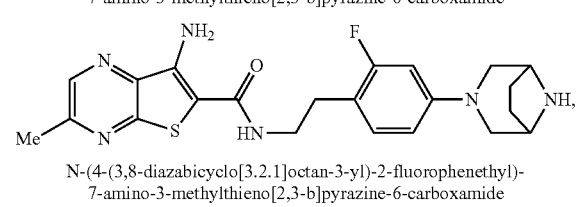

N-(4-(3,8-diazabicyclo[3.2.1]octan-3-yl)-2-fluorophenethyl)-
7-amino-3-methylthieno[2,3-b]pyrazine-6-carboxamide -continued

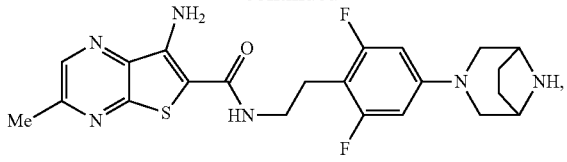

N-(4-(3,8-diazabicyclo[3.2.1]octan-3-yl)-2,6-difluorophenethyl)-
7-amino-3-methylthieno[2,3-b]pyrazine-6-carboxamide

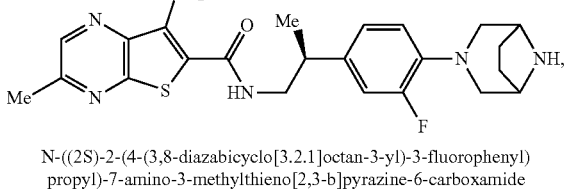

N-((2S)-2-(4-(3,8-diazabicyclo[3.2.1]octan-3-yl)-3-fluorophenyl)
propyl)-7-amino-3-methylthieno[2,3-b]pyrazine-6-carboxamide

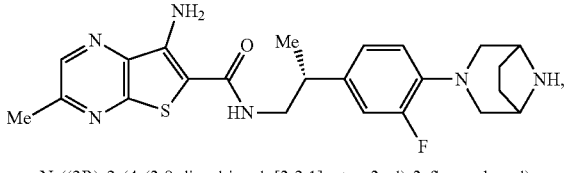

N-((2R)-2-(4-(3,8-diazabicyclo[3.2.1]octan-3-yl)-3-fluorophenyl)
propyl)-7-amino-3-methylthieno[2,3-b]pyrazine-6-carboxamide

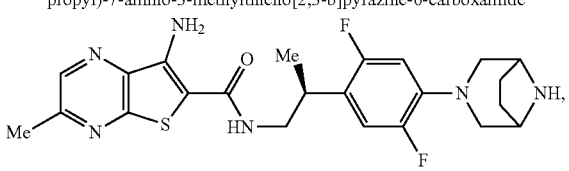

N-((2S)-2-(4-(3,8-diazabicyclo[3.2.1]octan-3-yl)-2,5-
difluorophenyl)propyl)-7-amino-3-methylthieno[2,3-b]pyrazine-6-
carboxamide

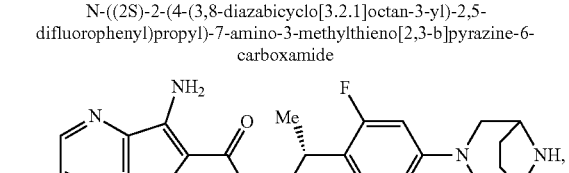

N-((2R)-2-(4-(3,8-diazabicyclo[3.2.1]octan-3-yl)-2,5-
difluorophenyl)propyl)-7-amino-3-methylthieno[2,3-b]pyrazine-6-
carboxamide

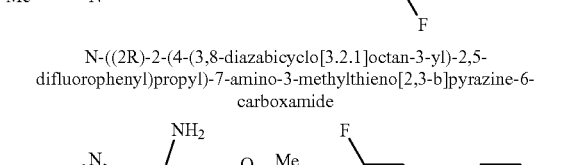

N-((2S)-2-(4-(3,8-diazabicyclo[3.2.1]octan-3-yl)-2-fluorophenyl)propyl)-
7-amino-3-methylthieno[2,3-b]pyrazine-6-carboxamide

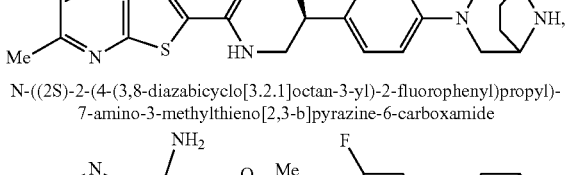

N-((2R)-2-(4-(3,8-diazabicyclo[3.2.1]octan-3-yl)-2-fluorophenyl)propyl)-
7-amino-3-methylthieno[2,3-b]pyrazine-6-carboxamide

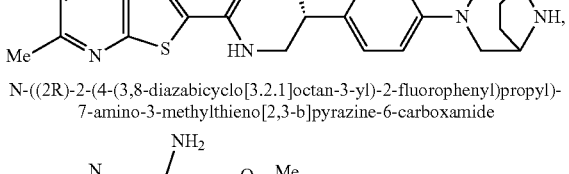

N-((2S)-2-(4-(3,8-diazabicyclo[3.2.1]octan-3-yl)-3-cyanophenyl)propyl)-
7-amino-3-methylthieno[2,3-b]pyrazine-6-carboxamide -continued

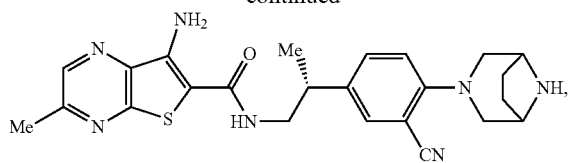

N-((2R)-2-(4-(3,8-diazabicyclo[3.2.1]octan-3-yl)-3-cyanophenyl)propyl)-7-amino-3-methylthieno[2,3-b]pyrazine-6-carboxamide

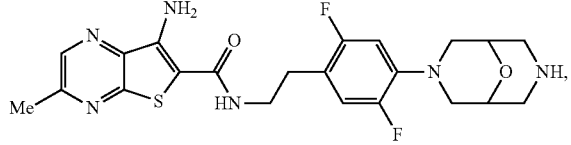

N-(4-(9-oxa-3,7-diazabicyclo[3.3.1]nonan-3-yl)-2,5-difluorophenethyl)-7-amino-3-methylthieno[2,3-b]pyrazine-6-carboxamide

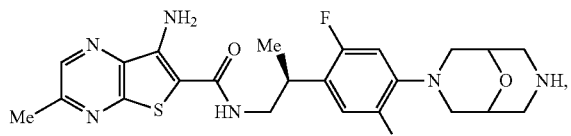

N-((2R)-2-(4-(9-oxa-3,7-diazabicyclo[3.3.1]nonan-3-yl)-2,5-difluorophenyl)propyl)-7-amino-3-methylthieno[2,3-b]pyrazine-6-carboxamide or

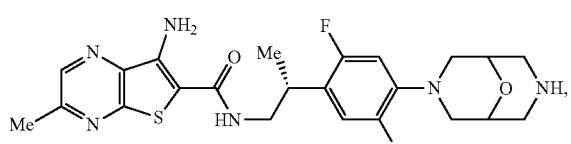

N-((2S)-2-(4-(9-oxa-3,7-diazabicyclo[3.3.1]nonan-3-yl)-2,5-difluorophenyl)propyl)-7-amino-3-methylthieno[2,3-b]pyrazine-6-carboxamide or a pharmaceutically acceptable salt, stereoisomer, or tautomer thereof.

15. The compound of claim 1, selected from:

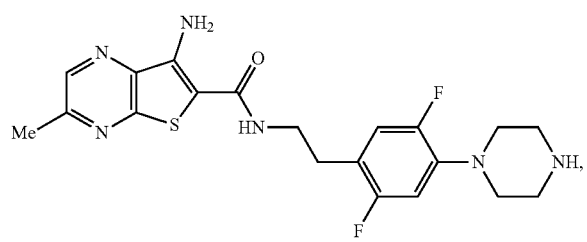

7-amino-N-(2,5-difluoro-4-(piperazin-1-yl)phenethyl)-3-methylthieno[2,3-b]pyrazine-6-carboxamide

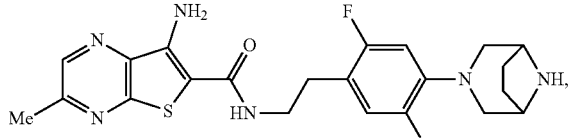

N-(4-(3,8-diazabicyclo[3.2.1]octan-3-yl)-2,5-difluorophenethyl)-7-amino-3-methylthieno[2,3-b]pyrazine-6-carboxamide or a pharmaceutically acceptable salt, stereoisomer, or tautomer thereof.

16. A compound of Formula (I'):

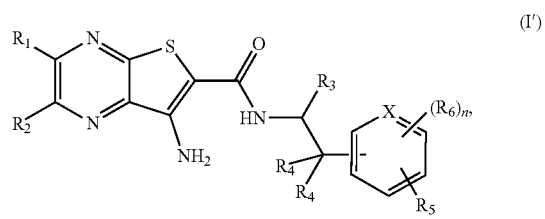

or a pharmaceutically acceptable salt, stereoisomer, or tautomer thereof, wherein:

X is $CR_6$; $R_1$ is $(C_1\text{-}C_6)$ alkyl;

$R_2$, $R_3$, $R_4$, and $R_4'$ are each H;

$R_5$ is —$(C_0\text{-}C_3)$ alkylene-(3-9 member heterocyclyl), wherein the heterocyclyl is optionally substituted with one or more $R_{13}$;

each $R_6$ is independently at each occurrence H or halogen each $R_{13}$ is independently at each occurrence $(C_1\text{-}C_6)$ alkyl; or two $R_{13}$ together with the atoms to which they are attached can form a bridged heterocyclyl ring optionally substituted with one or more $R_{20}$;

each $R_{20}$ is independently at each occurrence $(C_1\text{-}C_6)$ alkyl or halogen; and n is 0, 1, 2, or 3.

17. The compound of claim 16, wherein $R_5$ is a —$(C_0)$ alkylene-(3-9 member heterocyclyl), optionally substituted with one or more $R_{13}$.

18. The compound of claim 17, wherein the heterocyclyl is substituted by two $R_{13}$ together with the atoms to which they are attached forming a bridged heterocyclyl ring.

19. A pharmaceutical composition comprising an effective amount of the compound of claim 13, and a pharmaceutically acceptable carrier.

20. A pharmaceutical composition comprising a pharmaceutically acceptable carrier and an effective amount of a compound selected from

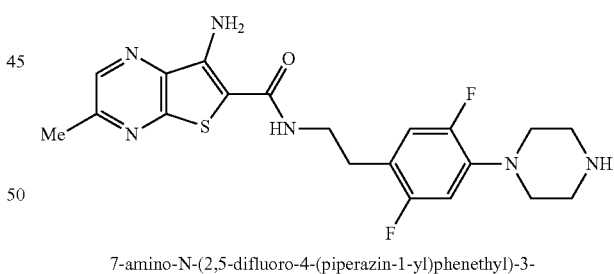

7-amino-N-(2,5-difluoro-4-(piperazin-1-yl)phenethyl)-3-methylthienno[2,3-b]pyrazine-6-carboxamide,

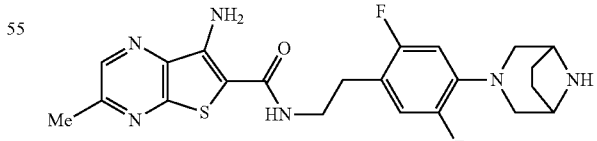

N-(4-(3,8-diazabicyclo[3.2.1]octan-3-yl)-2,5-difluorophenethyl)-7-mino-3-methylthieno[2,3-b]pyrzine-6-carboxamide, or a pharmaceutically acceptable salt, stereoisomer, or tautomer thereof.

21. The compound of claim 1, wherein the 3-8 member heterocyclyl is selected from the group consisting of: oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl.

22. The compound of claim 1, wherein the 5-24 member heteroaryl is selected from the group consisting of: furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuranyl, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1λ²-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c] [1,2,5]thiadiazolyl, benzo[c] [1,2,5]oxadiazole, 1,3-dihydro-2H-benzo[d]imidazol-2-one, 3,4-dihydro-2H-pyrazolo[1,5-b] [1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, and 3H-indolyl.

23. The compound of claim 1, which is:

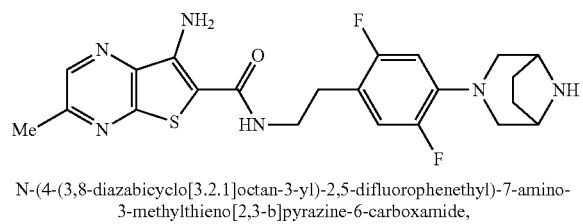 [SMILES: Cc1cnc2c(N)c(C(=O)NCCc3cc(F)c(N4CC5CCC(C4)N5)cc3F)sc2n1]

N-(4-(3,8-diazabicyclo[3.2.1]octan-3-yl)-2,5-difluorophenethyl)-7-amino-3-methylthieno[2,3-b]pyrazine-6-carboxamide, or a pharmaceutically acceptable salt, stereoisomer, or tautomer thereof.

24. The compound of claim 1, wherein $R_5$ is 8-membered heterocyclyl.

25. The compound of claim 1, or a pharmaceutically acceptable salt, stereoisomer, or tautomer thereof, wherein:

X is $CR_6$;

$R_1$ is H or $(C_1-C_6)$ alkyl;

$R_2$ is H or $(C_1-C_6)$ alkyl;

$R_3$ is H;

$R_4$, and $R_4'$ are each H or $(C_1-C_6)$ alkyl;

$R_5$ is 3-9 member heterocyclyl, wherein the heterocyclyl includes 2-3 heteroatoms independently selected from N and O;

each $R_6$ is independently at each occurrence H, halogen, or —CN; and n is 0, 1, 2, or 3.

26. A pharmaceutical composition comprising a pharmaceutically acceptable carrier and an effective amount of the compound of claim 14, or pharmaceutically acceptable salt, stereoisomer, or tautomer thereof.

27. The compound of claim 1, which is:

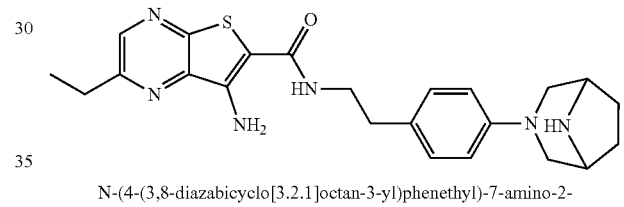

N-(4-(3,8-diazabicyclo[3.2.1]octan-3-yl)phenethyl)-7-amino-2-ethylthieno[2,3-b]pyrazine-6-carboxamide.

28. The compound of claim 1, which is:

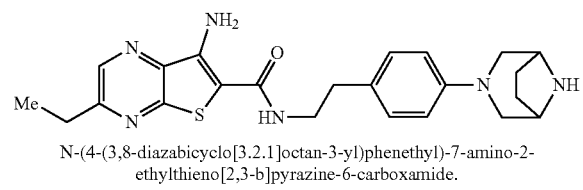 [SMILES: CCc1cnc2c(N)c(C(=O)NCCc3ccc(N4CC5CCC(C4)N5)cc3)sc2n1]

N-(4-(3,8-diazabicyclo[3.2.1]octan-3-yl)phenethyl)-7-amino-2-ethylthieno[2,3-b]pyrazine-6-carboxamide.

* * * * *

UNITED STATES PATENT AND TRADEMARK OFFICE
CERTIFICATE OF CORRECTION

PATENT NO. : 10,889,592 B2
APPLICATION NO. : 16/077406
DATED : January 12, 2021
INVENTOR(S) : David Joseph Guerin et al.

It is certified that error appears in the above-identified patent and that said Letters Patent is hereby corrected as shown below:

In the Claims

Column 83, Line 41, Claim 1, delete "($C_0$---$C_3$)" and insert --($C_0$-$C_3$)--.

Column 90, Lines 46-47, Claim 28, delete "N-(4-(3,8-diazabicyclo[3.2.1]octan-3-yl)phenethyl)-7-amino-2-ethylthieno[2,3-b]pyrazine-6-carboxamide" and insert --N-(4-(3,8-diazabicyclo[3.2.1]octan-3-yl)phenethyl)-7-amino-3-ethylthieno[2,3-b]pyrazine-6-carboxamide--.

Signed and Sealed this
Fourth Day of May, 2021

Drew Hirshfeld
*Performing the Functions and Duties of the
Under Secretary of Commerce for Intellectual Property and
Director of the United States Patent and Trademark Office*